United States Patent
Olavesen et al.

(10) Patent No.: US 7,329,540 B2
(45) Date of Patent: Feb. 12, 2008

(54) CORNEODESMOSIN BASED TEST AND MODEL FOR INFLAMMATORY DISEASE

(75) Inventors: Mark Olavesen, Oxfordshire (GB); Nick Lench, Oxfordshire (GB); Maxine Allen, Oxfordshire (GB); Rachind Tazi-Ahnini, Sheffield (GB)

(73) Assignee: York Pharma (R & D) Limited, London (GB)

( * ) Notice: Subject to any disclaimer, the term of this patent is extended or adjusted under 35 U.S.C. 154(b) by 587 days.

(21) Appl. No.: 10/204,884

(22) PCT Filed: Feb. 23, 2001

(86) PCT No.: PCT/GB01/00795

§ 371 (c)(1),
(2), (4) Date: Jan. 29, 2003

(87) PCT Pub. No.: WO01/62788

PCT Pub. Date: Aug. 30, 2001

(65) Prior Publication Data

US 2003/0186371 A1    Oct. 2, 2003

(51) Int. Cl.
*C12N 15/63* (2006.01)

(52) U.S. Cl. .................. 435/320.1; 435/325; 536/23.1

(58) Field of Classification Search ............... None
See application file for complete search history.

(56) References Cited

OTHER PUBLICATIONS

*Homo sapien* clone UWGC: y24c203 from 6p21, Accession No. AC006163. Janer et al. Large scale sequence analysis of the human MHC class I region, 1998.*
*Homo sapien* genomic DNA, HLA class 1 region. Shiina et al. Accession No. AB023060, 1999.*
Allen, M.H., et al., "A Non-HLA Gene Within the MHC in Psoriasis," *Lancet* 353:1589-1590, 1999.
Guerrin, M., et al., "Expression Cloning of Human Corneodesmosin Proves Its Identity With the Product of the *S* Gene and Allows Improved Characterization of Its Processing During Keratinocyte Differentiation," *J. Biol. Chem.* 273(35):22640-22647, 1998.
Tazi-Ahnini, R., et al., "Novel Genetic Association Between the Corneodesmosin (*MHC S*) Gene and Susceptibility to Psoriasis," *Hum. Mol. Genet.* 8(6):1135-1140, 1999.

* cited by examiner

*Primary Examiner*—Celine Qian
(74) *Attorney, Agent, or Firm*—Christensen O'Connor Johnson Kindness PLLC

(57) ABSTRACT

The present invention relates to a polynucleotide encoding the corneodesmosin protein having one or more nucleotide insertions, deletions or substitutions at one or novel positions. The invention also relates to the corneodesmosin protein having one or more amino acid insertions, deletions and substitutions. These nucleotide and amino acid polymorphisms are useful in diagnosing or determining susceptibility to corneodesmosin-mediated disease, for example inflammatory diseases including psoriasis, and in treating such disease. Host cells and transgenic non-human animals comprising polynucleotides or proteins of the invention are provided. Methods of screening for agents for use in treating corneodesmosin-mediated disease are also provided.

4 Claims, 11 Drawing Sheets

FIG. 1

Genomic Sequence of Corneodesmosin Gene

```
6701  TGGAGGGCAG ATGGAGAGAC AGGCCAAGCC ACGGTAGGCA GGAGAGTTAA
6751  GGAGCCAGGC AGCTGGGTCC CGTGGCAAGA GTGGCCGCCC CAGAGTGGGT
6801  GGCCGTGGGG CAGAGCGCCT GGTTCCGGGT TAGGCAATGA GGAGCCGGGG
6851  CCAGGCCTGT CAGGTGGCAG GATCGTTAGA GCCCCGTGGC CATGGGTACC
6901  CCACACTGCA GCCACTGCTG CTGCTGAGTA GGCAGATGCA CCGGGCTGAT
6951  TACCACGGTG CTGCCGGCCA CACGAAGTTC CCCCGGGGCA CGCACGCCCT
7001  CCACCTCTCC TGGTCTCCCG ACAGTGACTG CTGCCCAGGG AATGTCCAGG
7051  TCTGGATAAA AGGAGCCAGG TTGTCCTCCAG GTGCCATCAG TCAGGACGCC
7101  GTGCAGCCCG AGATGGGCTC GTCTCGGGCA CCCTGGATGG GGCGTGTGGG
7151  TGGGCACGGG ATGATGGCAC TGCTGCTGGC TGGTCTCCTC CTGCCAGGTA
7201  GGAGGCTGGG GGCCCTGGGA ACAGGAGGGA GGCGGGAGGG AGACTCCGGG
7251  AGAGGACCCA GCGAAGGGGA CGGGCAGGGG CTCTGGAATC TGCCTTTTGA
7301  GTCTGGGGGT TGCTCCTCAC TGTATGGTCG CCTCAGGTAA GTTTCTTAAA
7351  CTTCCTGAGC CCCAGTTTCT GAAATTCTGA AGTGGGGTTA ATGACACCTA
7401  CCTCTAGTCT GTGTGTCTCA AATTAAATAA TGTATGTGAT ATGTACTTTG
7451  GAAATTCTAG AGGTTTATAT AAATGGTGGT GGTGATTTTT ATTATGGGAG
7501  CACTACAAGA TAATGATTGG ACATTTAATA GTAATAATAT CATTTTTAGA
7551  GCCTTTTTAT ATGCTAGACT CTGTTTTAAG CACATTTGGA TTATATATTA
7601  GAACTTTTAT TTTTATTTTT TTTGTGAGAT GGAGTCCCAC TCTGTCTCCA
7651  AGGCTGGAGT GCAGTGGCGT AATCTCGGCT CACTGCAACT TCCACCTCTC
7701  AGGTTCAAGC GACTCTCATG CCTCAGCCTC TAGAGTAGCT GGGACAACAG
7751  GTGCCCATCA CCACACCTGG CTAATTTTCT TTTTTTTGTA TTTTTAGTAG
7801  AAACAGGGTT TTACCATTTT GGTCAAGCTG GTCTTGAACT CCTGACTCAA
7851  GTGATCCGCT CGCCTCGGCC TCCCAAGGTG CTGGGATTAC AGGCATGAGC
7901  CACCACACCC GGCCTATATT AGCACTTTTG ATCATTACAA GAACGGTATG
```

```
7951  AAAAGAGATT TGCTATTTCC ACTCTACAGA TGAGGACACT GAGGCTCGGA
8001  GAGGTTAGGA AACTAGCTCA AAATCATGCA TTAGAAGGCA GCAAAGCCAA
8051  GATTTCAACC CCAGGCCAGG CAACCCCTGG ACCTGTGTTG TTGACCACCG
8101  GGTACTTATA GCCCTTGAGG AATTTCTGCG ACCTTCCCAT GGTCTAGTGG
8151  GTGGTTGGTG TCTGAGGGAA TAGCGAAAGA GAGAGGCAAT GCATGGTGGA
8201  TTCGTGCAGA GGACTGAAGG GAATTGGCAC AGCTGGGGTT CGGCGTGGAG
8251  GTGCATGCAG AGAATTTCTT TCTGAGGAGA GAACAGGGAC ATCACAGAGG
8301  ATGGCAGTCT GGTTGTTGGT GGAGGGATCA GGATGAGTGG CAGTAATAAT
8351  TCATAATATA TAATGCTTTA CACTTTCTAA AACATCTGGC CGCACATGAT
8401  AGCTTGTGCC TGTAATCCCA ACACTTCAGG AGGCCAAGGC AGGTGAATCG
8451  CCTGAGGTCA GGAGTTCAAG ACCAGCCTGG CCAAGATGGT GAAACCCCCT
8501  CTCTACTAAA AATACAAAAA ATTAGCTGGG TGTGGTGGCG GGCACCTGTG
8551  GTCCCAGCTA CTTGGGAGGC TGAGGCAGGA GAATCGCTTG CACCAAGGAG
8601  GCAGAGGTTA CAGTGAGCTG AGACCGTGTT ATTGCACTTT AGCCTGGGCA
8651  ACAAGAAACT CCATCTCACA AAAAAAAAAA AAAAAAAAAA AAAGAAGAAA
8701  AAACTTCCAG GTGGATGATC TCATTTAGTT TTCTTCATAG TAATGCTGTG
8751  GGAAGGCAGG GAAAATTTGG CCCCTCTGAA TGTATAAACT AAAGCTCAGA
8801  GAGGTTCAGT AACTTGCTAG TATGTGGCTC TGTTTGTAAC ACGTGGGACC
8851  TGGAGGGGCT AGGGAAGGCA GAAGGAACGC AGGTGAAAGA GTCATGGAGG
8901  AACCATGGGG TAAGTTGGGC CTGGGGTTTT GAGCAAAGGA AAGGAAAGAT
8951  AAGGAAAGAT GTGGCTCCAC ATCCCTGAGG GAAGTCAAGG CAGCAGAAGT
9001  CAGATGAGGG GCTGGACAGA GGCAGGTGTG CTCAGAGAGG GAAGCTGATT
9051  GTGGCCAGGA GCCTCGGAGG TTCGTGGGGT TTCGTCCTGG TTCCCTGGGC
9101  TGGCCAGCG AGAGCAGGGC TGGCTCAGGG TGCGGTGTCC TGACACACTG
9151  GTACCAGCAG GTTCTGAAGC AACAGGTAGT GACCCCACAT CCTGGCCCCC
9201  ACCCAGCTTT ACTGGCATGG CCAGTGCTGA GATAGGAAAT AGGGTTTCCA
```

FIG. 1 CONT'D

```
9251   TTCCTGACCC CAGCCTGGGC TCTCACGAAG AAGCTGGTGA CCAAATCTTA
9301   GTCCTCGAGT GCCCTTTCCT TTATTTCAGC CCCTCTGCCC CCAGCTTTGT
9351   CTTTTTCCAG TGTCTCCTTC TATATGTGTC TCCACTTCTC AGCCCTCCAT
9401   TGTTTTGCCT TTTGTCTTCT TCCCTCTGGT CCCACTGTCT GGCCCAGGAT
9451   TTTTCCCCTA AGAATTTACG CCTGGACTCC TCAGAGCCTC AGTTTCCCCA
9501   ATTCTCTGTC TCTTCAGGGT CCTTTCTTTT AGACCTATTT GTTCCTGCCC
9551   CTTCTCCATT CCCTCTTCTT TTTAAAAAAA ATTTTAATTA AAAAACAAAA
9601   TACAGATGGG GTCTATGTTG CCCAGGCTGG TCTTGAACTC TGGGGCGCAT
9651   GCAATCCTCC CACCTCAGCC TCCCAAAGTG CTGGGATTAC CGGCGTGAGC
9701   CACTGTGCCC AGCCCCCTCT TATATTCAAT GTATTCCTTT GAGGTCACTC
9751   ACTTTGGCAC GTAATTTTCT ATTTTTCTGG TTGGTGTTTG CCCACCCTTC
9801   CCAAACAAAG AAATGCCTTT ATTCGGCCAC CTCAATATCC TTTAGAGACA
9851   ATAGCCAGTT CTTCCTCCTT TCTCCATCCC TAAACTCTCC CTGCGCTCTG
9901   CTTGGGAGAA ACCCGAGAGG CCGATTACTG AGATAAGGCA GAAAGGTGAG
9951   GGAGGAAGCC AAGCCTCCTT GGCCCTTACT AACCACTGCT TTCCTCCACA
10001  GGGACCTTGG CTAAGAGCAT TGGCACCTTC TCAGACCCCT GTAAGGACCC
10051  CACGCGTATC ACCTCCCCTA ACGACCCCTG CCTCACTGGG AAGGGTGACT
10101  CCAGCGGCTT CAGTAGCTAC AGTGGCTCCA GCAGTTCTGG CAGCTCCATT
10151  TCCAGTGCCA GAAGCTCTGG TGGTGGCTCC AGTGGTAGCT CCAGCGGATC
10201  CAGCATTGCC CAGGGTGGTT CTGCAGGATC TTTTAAGCCA GGAACGGGGT
10251  ATTCCCAGGT CAGCTACTCC TCCGGATCTG GCTCTAGTCT ACAAGGTGCA
10301  TCCGGTTCCT CCCAGCTGGG GAGCAGCAGC TCTCACTCGG AAGCAGCGG
10351  CTCTCACTCG GAAGCAGCA GCTCTCATTC GAGCAGCAGC AGCAGCTTTC
10401  AGTTCAGCAG CAGCAGCTTC CAAGTAGGGA ATGGCTCTGC TCTGCCAACC
10451  AATGACAACT CTTACCGCGG AATACTAAAC CCTTCCCAGC CTGGACAAAG
10501  CTCTTCCTCT TCCCAAACCT CTGGGGTATC CAGCAGTGGC CAAAGCGTCA
```

```
10551  GCTCCAACCA GCGTCCCTGT AGTTCGGACA TCCCCGACTC TCCCTGCAGT

10601  GGAGGGCCCA TCGTCTCGCA CTCTGGCCCC TACATCCCCA GCTCCCACTC

10651  TGTGTCAGGG GGTCAGAGGC CTGTGGTGGT GGTGGTGGAC CAGCACGGTT

10701  CTGGTGCCCC TGGAGTGGTT CAAGGTCCCC CCTGTAGCAA TGGTGGCCTT

10751  CCAGGCAAGC CCTGTCCCCC AATCACCTCT GTAGACAAAT CCTATGGTGG

10801  CTACGAGGTG GTGGGTGGCT CCTCTGACAG TTATCTGGTT CCAGGCATGA

10851  CCTACAGTAA GGGTAAAATC TATCCTGTGG GCTACTTCAC CAAAGAGAAC

10901  CCTGTGAAAG GCTCTCCAGG GGTCCCTTCC TTTGCAGCTG GGCCCCCCAT

10951  CTCTGAGGGC AAATACTTCT CCAGCAACCC CATCATCCCC AGCCAGTCGG

11001  CAGCTTCCTC GGCCATTGCG TTCCAGCCAG TGGGGACTGG TGGGGTCCAG

11051  CTCTGTGGAG GCGGCTCCAC GGGCTCCAAG GGACCCTGCT CTCCCTCCAG

11101  TTCTCGAGTC CCCAGCAGTT CTAGCATTTC CAGCAGCTCC GGTTCACCCT

11151  ACCATCCCTG CGGCAGTGCT TCCCAGAGCC CCTGCTCCCC ACCAGGCACC

11201  GGCTCCTTCA GCAGCAGCTC CAGTTCCCAA TCGAGTGGCA AAATCATCCT

11251  TCAGCCTTGT GGCAGCAAGT CCAGCTCTTC TGGTCACCCT TGCATGTCTG

11301  TCTCCTCCTT GACACTGACT GGGGGCCCCG ATGGCTCTCC CCATCCTGAT

11351  CCCTCCGCTG GTGCCAAGCC CTGTGGCTCC AGCAGTGCTG GAAAGATCCC

11401  CTGCCGCTCC ATCCGGGATA TCCTAGCCCA AGTGAAGCCT CTGGGGCCCC

11451  AGCTAGCTGA CCCTGAAGTT TTCCTACCCC AAGGAGAGTT ACTCGACAGT

11501  CCATAAGTGA ACTGTTGTGT GTGTGCATGC CTTGGGCACA AACAAGCACA

11551  TACACTATAT CCCATATGGG AGAAGGCCAG TGCCCAGGCA TAGGGTTAGG

11601  TCAGTTTCCC TCCTTCCCAA AAGAGTGGTT CTGGTTTGTC TAGTACCCTA

11651  AGGTTGCAGA CTCTCTCTTA TCACCCGTTC CTCCTTCCTC TTCTCAAAAT

11701  GGTAGATTCA AAGCTCCTCT CTTGATTGTG TCCTACTGTT TAAATTCCCA

11751  TTCCACGACA GTGCCCCTCA GCCAGATCAC GACCCCTTAC AATTGCCTCT

11801  ACTGTGTTGA AATGGTCCAT TGAGTAACAC CCCCATCACC TTCTCAACTG
```

11851 GGAAACCCCT GAAATGCTCT CAGAGCAGCT CTGACGCCTG AAGAAGTTA
11901 ACCTTCCTCT TCCCCTTTAC CAAATAAAGG AAAGTCAAAG CATGATCTGG
11951 AAACAGTGGC CACTTTTCAC TGAGCTCTCT TCGACATCTA GTGAACGGAG
12001 CCAATATGCC ACTGGGCTTT CGGTCCCAAT TCCACCCGAG CCTCCATTAC
12051 AGAGCTCAGG ACGCCGTCCT AGATCACCGT CCCCAACACA CCCATTGCGT
12101 CTCAAGGCCG TTATCTCAGC GCCTTCCTGT GGCCATTTCC CTCAGTGCCC
12151 AGATGATTCC CTGGGTGAGG GAGACACTGG GGCACCCTCA GAGGTTCGAG
12201 CAGGGTCCGT CCTCTCCCTG GATCCTGGAG AGATGGCTCA GTAAACTGTG
12251 GGGACTAGGT GCAGACTTTT TGCCTTCTTG GAGTCCTGGG TCTCCTCTGA
12301 GACTCTGGCT CCTGCTCTTC CTACGCCTCT AGAGCTCTCT GTGTCCCTGA
12351 TTTTCCTTCA AAAGCGGCGT GTGTTTCTCT TGTACCTTCC AGCTCCTGCC
12401 ACAGAGCAGG AAGACAATAA ATATTTGTTG AACTCAAAGC AGAGATTGCC
12451 TGGCCTCGCA GATCGTTCCG CCATTTCCCT CCTCTCTCAT TGGTCCAGGA
12501 AATCCATTCT CTTCCCATTC CTCATTCACC GTGGGGTCCC CCTTCCGCTT
12551 ATTTAGGGCC CTCAGTGTTT TCTCTCCGTC CGCTCCCCTG CCCTCCCCAG
12601 GGAAACTCCT TTTGTTCCAG CATTAGCATT CCTGACCTTC TAGATGCGAT
12651 CCTCTCTGGG AGTCATGAGT CTCGATTTCC TGGGTTTCTG GGACACCTGG
12701 AAGCTTGGGA AGGCTGGGAG AGAACAACTC CAACCAGATT CCTGTCAGCT
12751 TGAGTAGGAGG CCAGTTGGGC GTTGTTCCTG GAGCTGGGGG TGGAGAGAGT
12801 AAAGGACTGA GAGGATGGGA GCCGGGCAGG GAGTGCAGCC AACCAGCGTG
12851 ACTCACTGGC CTAGATCAAG AGGCCCAGCC TGTGGCAGAA CAGAGCTGCC
12901 AGTGGTCTCT CCATCTTCAC ACTCCCTGCT CTGCTGGGGT CCACAGTGAG
12951 AGTGTGAGCA ACATGGCTCT CAGGTGAGGG CTGAGAAGGC AGAGTGCCCC
13001 AGTGGGAAAG AGGAGTCGCT TCCACTGGAG AAGAGAGAGA AAGTGGAGTG
13051 TGTGGTGGGG TCCATGCGAC TTAAGTCCTG AGACAGGCAG GGAGAGGCTG
13101 AGGCGGACGA AGTTCCCCCA TCCCAAGGAG GGCAGAGTGG ATTGTGCTTG

FIG. 1 CONT'D

```
13151 TCCCTCTACC AGCGGCAGCG CCCACCCCAG GCCACCTCTC AGAGCCTCTG
13201 CTTCGCTGCA AAGGAATTCA CCCCTACTGT AGCACTAAC CCATTCCCTC
13251 CTATAGCCT GGTGCTGTT GCTGCTGAAT TTAGAACTGT TGAAAGTGCA
13301 AGTCTGGAAT CAGCAAATAT GTATTACATT GACCAGATAC GGATTCAATC
13351 ACCCTTGCTC CAGCATGTCG CCTCTGATCT GGAGCCAATG GCAGGAATCC
13401 AGGTCTCTCAC ATGCTTCATC AATGGGAATT GCAGCGAGAG AAGCCTGTGT
13451 GATGTGGTGT TTCCTCGACT CTCCTGCTGT GCTCCAAATT AAAAGCTTGT
13501 GTAAAAGTGA TCCATGTCAT CCAAAATGGC CTCTGGCTG CATCGACTGC
13551 CACTTCTGGA GACGAGCTCT TCAGTCGTCC AGTCGTTAAG CCACCACGGG
13601 CACCTGGCGA GGACACAGCA CTAGAATCAC CCAACAGCTC ATGTTTAGAC
13651 CTTGGCCAGC CAGGGAAGCC TAGTCGTGGG GCGTGCCGGA AGCCATGGAG
13701 AGAACAAACG CATTCCATTT TATAATAAAA ATTCGATACT ATATTTAAAA
13751 GCCAACAAAC TGTTAATGAA TCTCTACATT CTCATCGCCC AGGTTCAACA
13801 AGGATCCCAG CTTCAACAAG GATCAAGTCC TGGCCATTTG ACACCAGCAT
13851 TTAAAGCTC TCCTCTACTC TTACTTGGAA ATAGCCACTT TGTCGCAAGC
13901 TTTCTTATAC TCTGTGGCAC ATCTGACCAC CAGTAGCAGG CAGAATGATG
13951 TGTTGAACCC CAACACCATG AAACATCTCC ACATGCTAAT CCGTGGAACG
14001 TAGGAATTAG GTTACATGCC AAAGCCAAAT TAAGGTTCCA GATGGGATTA
14051 ACGTTGCTAT TCGGCTGACT TCACAGAGAT TATCATGGAT TATTCACGTG
14101 GGTCCAGTGT AGTCACCAGG TCCCTTAATC TGGACATGGC AGCCAGAACA
14151 GGAAGTCTGA CTGATACAGT GTAAGAAATG GCTGATTTTG GCTTTGGAGA
14201 TGGAGCAAGG GGACCATGAG CCAAAGAACA CAGGATGCCT CTAGAAGGTG
14251 AAAAAGCAGG GAAAGGGATT TTCCCCTGAC GCCCCCAGAA AGAATCACAG
14301 CCCTGCTGAC ACCTTTATTT TAATCGACTG AGACCTGTTT TAGACTTCTG
14351 ATCTCCAAAA CTGTAAAGTA ATAAATCCAT GTTGTTGTAA GCCATTCCGT
```

UTR Sequence    Exon Sequence    SNP

CORNEODESMOSIN (af030130.em_hum1)

```
                                                       T
     ATGGGCTCGTCTCGGGCACCCTGGATGGGGCGTGTGGGTGGGCACGGGATGATGGCACTG
 15  -----+---------+---------+---------+---------+---------+----  74
     TACCCGAGCAGAGCCCGTGGGACCTACCCCGCACACCCACCCGTGCCCTACTACCGTGAC

M  G  S  S  R  A  P  W  M  G  R  V  G  G  H  G  M  M  A  L   -
                                                         L

CTGCTGGCTGGTCTCCTCCTGCCAGGGACCTTGGCTAAGAGCATTGGCACCTTCTCAGAC
 75  -----+---------+---------+---------+---------+---------+----  134
     GACGACCGACCAGAGGAGGACGGTCCCTGGAACCGATTCTCGTAACCGTGGAAGAGTCTG

L  L  A  G  L  L  L  P  G  T  L  A  K  S  I  G  T  F  S  D   -

T                                    T
     CCCTGTAAGGACCCCACGCGTATCACCTCCCCTAACGACCCCTGCCTCACTGGGAAGGGT
135  -----+---------+---------+---------+---------+---------+----  194
     GGGACATTCCTGGGGTGCGCATAGTGGAGGGGATTGCTGGGGACGGAGTGACCCTTCCCA

P  C  K  D  P  T  R  I  T  S  P  N  D  P  C  L  T  G  K  G   -
                                                    S
                 T
     GACTCCAGCGGCTTCAGTAGCTACAGTGGCTCCAGCAGTTCTGGCAGCTCCATTTCCAGT
195  -----+---------+---------+---------+---------+---------+----  254
     CTGAGGTCGCCGAAGTCATCGATGTCACCGAGGTCGTCAAGACCGTCGAGGTAAAGGTCA

D  S  S  G  F  S  S  Y  S  G  S  S  S  S  G  S  S  I  S  S   -

GCCAGAAGCTCTGGTGGTGGCTCCAGTGGTAGCTCCAGCGGATCCAGCATTGCCCAGGGT
255  -----+---------+---------+---------+---------+---------+----  314
     CGGTCTTCGAGACCACCACCGAGGTCACCATCGAGGTCGCCTAGGTCGTAACGGGTCCCA

A  R  S  S  G  G  G  S  S  G  S  S  S  G  S  S  I  A  Q  G   —

GGTTCTGCAGGATCTTTTAAGCCAGGAACGGGGTATTCCCAGGTCAGCTACTCCTCCGGA
315  -----+---------+---------+---------+---------+---------+----  374
     CCAAGACGTCCTAGAAAATTCGGTCCTTGCCCCATAAGGGTCCAGTCGATGAGGAGGCCT

G  S  A  G  S  F  K  P  G  T  G  Y  S  Q  V  S  Y  S  S  G   —

TCTGGCTCTAGTCTACAAGGTGCATCCGGTTCCTCCCAGCTGGGGAGCAGCAGCTCTCAC
375  -----+---------+---------+---------+---------+---------+----  434
     AGACCGAGATCAGATGTTCCACGTAGGCCAAGGAGGGTCGACCCCTCGTCGTCGAGAGTG

S  G  S  S  L  Q  G  A  S  G  S  S  Q  L  G  S  S  S  H   -
```

```
                    A                    del
       TCGGGAAGCAGCGGCTCTCACTCGGGAAGCAGCAGCTCTCATTCGAGCAGCAGCAGCAGC
435    -----+---------+---------+---------+---------+---------+----  494
       AGCCCTTCGTCGCCGAGAGTGAGCCCTTCGTCGTCGAGAGTAAGCTCGTCGTCGTCGTCG S  G  S  S  G  S  H  S  G  S  S  S  S  H  S  S  S  S  S  S  -
              N                    del TTTCAGTTCAGCAGCAGCAGCTTCCAAGTAGGGAATGGCTCTGCTCTGCCAACCAATGAC
495    -----+---------+---------+---------+---------+---------+----  554
       AAAGTCAAGTCGTCGTCGTCGAAGGTTCATCCCTTACCGAGACGAGACGGTTGGTTACTG

F  Q  F  S  S  S  S  F  Q  V  G  N  G  S  A  L  P  T  N  D  -

G
       AACTCTTACCGCGGAATACTAAACCCTTCCCAGCCTGGACAAAGCTCTTCCTCTTCCCAA
555    -----+---------+---------+---------+---------+---------+----  614
       TTGAGAATGGCGCCTTATGATTTGGGAAGGGTCGGACCTGTTTCGAGAAGGAGAAGGGTT

N  S  Y  R  G  I  L  N  P  S  Q  P  G  Q  S  S  S  S  S  Q  -

T
       ACCTCTGGGGTATCCAGCAGTGGCCAAAGCGTCAGCTCCAACCAGCGTCCCTGTAGTTCG
615    -----+---------+---------+---------+---------+---------+----  674
       TGGAGACCCCATAGGTCGTCACCGGTTTCGCAGTCGAGGTTGGTCGCAGGGACATCAAGC

T  S  G  V  S  S  S  G  Q  S  V  S  S  N  Q  R  P  C  S  S  -
           F

C
       GACATCCCCGACTCTCCCTGCAGTGGAGGGCCCATCGTCTCGCACTCTGGCCCCTACATC
675    -----+---------+---------+---------+---------+---------+----  734
       CTGTAGGGGCTGAGAGGGACGTCACCTCCCGGGTAGCAGAGCGTGAGACCGGGGATGTAG

D  I  P  D  S  P  C  S  G  G  P  I  V  S  H  S  G  P  Y  I  -
                                                      S

A
       CCCAGCTCCCACTCTGTGTCAGGGGGTCAGAGGCCTGTGGTGGTGGTGGTGGACCAGCAC
735    -----+---------+---------+---------+---------+---------+----  794
       GGGTCGAGGGTGAGACACAGTCCCCCAGTCTCCGGACACCACCACCACCACCTGGTCGTG

P  S  S  H  S  V  S  G  G  Q  R  P  V  V  V  V  V  D  Q  H  -

GGTTCTGGTGCCCCTGGAGTGGTTCAAGGTCCCCCCTGTAGCAATGGTGGCCTTCCAGGC
795    -----+---------+---------+---------+---------+---------+----  854
       CCAAGACCACGGGGACCTCACCAAGTTCCAGGGGGGACATCGTTACCACCGGAAGGTCCG

```
                      AAGCCCTGTCCCCCAATCACCTCTGTAGACAAATCCTATGGTGGCTACGAGGTGGTGGGT
855   -----+---------+---------+---------+---------+---------+----  914
                      TTCGGGACAGGGGGTTAGTGGAGACATCTGTTTAGGATACCACCGATGCTCCACCACCCA

K   P   C   P   P   I   T   S   V   D   K   S   Y   G   G   Y   E   V   V   G   -

C
                      GGCTCCTCTGACAGTTATCTGGTTCCAGGCATGACCTACAGTAAGGGTAAAATCTATCCT
915   -----+---------+---------+---------+---------+---------+----  974
                      CCGAGGAGACTGTCAATAGACCAAGGTCCGTACTGGATGTCATTCCCATTTTAGATAGGA

G   S   S   D   S   Y   L   V   P   G   M   T   Y   S   K   G   K   I   Y   P   -

GTGGGCTACTTCACCAAAGAGAACCCTGTGAAAGGCTCTCCAGGGGTCCCTTCCTTTGCA
975   -----+---------+---------+---------+---------+---------+----  1034
                      CACCCGATGAAGTGGTTTCTCTTGGGACACTTTCCGAGAGGTCCCCAGGGAAGGAAACGT

V   G   Y   F   T   K   E   N   P   V   K   G   S   P   G   V   P   S   F   A   -

GCTGGGCCCCCCATCTCTGAGGGCAAATACTTCTCCAGCAACCCCATCATCCCCAGCCAG
1035  -----+---------+---------+---------+---------+---------+----  1094
                      CGACCCGGGGGGTAGAGACTCCCGTTTATGAAGAGGTCGTTGGGGTAGTAGGGGTCGGTC

A   G   P   P   I   S   E   G   K   Y   F   S   S   N   P   I   I   P   S   Q

A
                      TCGGCAGCTTCCTCGGCCATTGCGTTCCAGCCAGTGGGGACTGGTGGGGTCCAGCTCTGT
1095  -----+---------+---------+---------+---------+---------+----  1154
                      AGCCGTCGAAGGAGCCGGTAACGCAAGGTCGGTCACCCCTGACCACCCCAGGTCGAGACA

S   A   A   S   S   A   I   A   F   Q   P   V   G   T   G   G   V   Q   L   C   -

GGAGGCGGCTCCACGGGCTCCAAGGGACCCTGCTCTCCCTCCAGTTCTCGAGTCCCCAGC
1155  -----+---------+---------+---------+---------+---------+----  1214
                      CCTCCGCCGAGGTGCCCGAGGTTCCCTGGGACGAGAGGGAGGTCAAGAGCTCAGGGGTCG

G   G   G   S   T   G   S   K   G   P   C   S   P   S   S   S   R   V   P   S   -

G                      T           T       T
                      AGTTCTAGCATTTCCAGCAGCGCCGGTTCACCCTACCATCCCTGCGGCAGTGCTTCCCAG
1215  -----+---------+---------+---------+---------+---------+----  1274
                      TCAAGATCGTAAAGGTCGTCGCGGCCAAGTGGGATGGTAGGGACGCCGTCACGAAGGGTC

S   S   S   I   S   S   S   A   G   S   P   Y   H   P   C   G   S   A   S   Q   -
                                       S   V   L
```

FIG. 2CONT'D

```
                                                                   C
     AGCCCCTGCTCCCCACCAGGCACCGGCTCCTTCAGCAGCAGCTCCAGTTCCCAATCGAGT
1275 -----+---------+---------+---------+---------+---------+---- 1334
     TCGGGGACGAGGGGTGGTCCGTGGCCGAGGAAGTCGTCGTCGAGGTCAAGGGTTAGCTCA

S   P   C   S   P   P   G   T   G   S   F   S   S   S   S   S   Q   S   S   -

C
     GGCAAAATCATCCTTCAGCCTTGTGGCAGCAAGTCCAGCTCTTCTGGTCACCCTTGCATG
1335 -----+---------+---------+---------+---------+---------+---- 1394
     CCGTTTTAGTAGGAAGTCGGAACACCGTCGTTCAGGTCGAGAAGACCAGTGGGAACGTAC

G   K   I   I   L   Q   P   C   G   S   K   S   S   S   S   G   H   P   C   M   -

TCTGTCTCCTCCTTGACACTGACTGGGGGCCCCGATGGCTCTCCCCATCCTGATCCCTCC
1395 -----+---------+---------+---------+---------+---------+---- 1454
     AGACAGAGGAGGAACTGTGACTGACCCCCGGGGCTACCGAGAGGGGTAGGACTAGGGAGG

S   V   S   S   L   T   L   T   G   G   P   D   G   S   P   H   P   D   P   S   -

GCTGGTGCCAAGCCCTGTGGCTCCAGCAGTGCTGGAAAGATCCCCTGCCGCTCCATCCGG
1455 -----+---------+---------+---------+---------+---------+---- 1514
     CGACCACGGTTCGGGACACCGAGGTCGTCACGACCTTTCTAGGGGACGGCGAGGTAGGCC

A   G   A   K   P   C   G   S   S   S   A   G   K   I   P   C   R   S   I   R   -

GATATCCTAGCCCAAGTGAAGCCTCTGGGGCCCCAGCTAGCTGACCCTGAAGTTTTCCTA
1515 -----+---------+---------+---------+---------+---------+---- 1574
     CTATAGGATCGGGTTCACTTCGGAGACCCCGGGGTCGATCGACTGGGACTTCAAAAGGAT

D   I   L   A   Q   V   K   P   L   G   P   Q   L   A   D   P   E   V   F   L

A
     CCCCAAGGAGAGTTACTCGACAGTCCATAA
1575 -----+---------+---------+---- 1604
     GGGGTTCCTCTCAATGAGCTGTCAGGTATT

P   Q   G   E   L   L   D   S   P   *
                              N
```

FIG. 2CONT'D

Distribution of SNPs across the Corneodesmosin gene (not to scale)

CORNEODESMOSIN BASED TEST AND MODEL FOR INFLAMMATORY DISEASE

The present invention relates to nucleotide substitutions, deletions or insertions in the corneodesmosin gene, and the exploitation of these polymorphisms in the detection and/or treatment of corneodesmosin mediated disease, for example inflammatory diseases including psoriasis. The present invention also relates to polynucleotides encoding the corneodesmosin protein, and having one or more nucleotide polymorphisms, and to a protein encoded by said polynucleotides. Also provided are transgenic non-human animals comprising the polynucleotides of the present invention; and methods and kits for treating, diagnosing or determining susceptibility to corneodesmosin mediated disease, in particular by way of gene therapy.

In recent years, it has been recognised that there is considerable genetic diversity in human populations, with common polymorphisms occurring on average at least every kilobase in the genome. Polymorphisms which affect gene expression or activity of the encoded gene product may account for susceptibility to, or expression of, disease conditions, either directly or through interaction with other genetic and environmental factors.

Understanding the molecular basis for disease, by sequencing the human genome and characterising polymorphisms, will enable the identification of those individuals at greatest risk of disease. This will allow the better matching of treatment and disease, and enable the production of new and improved targets for drugs. Screening and treatment of disease may also be better targeted to those in need, thus increasing the cost-effectiveness of health-care provision.

One area in need of such approaches is the diagnosis and treatment of inflammatory diseases. Inflammation, which can be broadly defined as the destructive sequelae to activation of elements of the body's immune system, is a feature of many diseases including infection, autoimmune disorders and benign and malignant hyperplasia. The identification of genetic factors which influence susceptibility to such disorders will provide important new insights into inflammatory disease, and may yield important new diagnostic and/or prognostic tests and treatments.

Psoriasis is a chronic inflammatory cutaneous disorder which affects approximately 2% of the population in the UK and US. Psoriasis manifests itself as red scaly skin patches, principally on the scalp, elbows and knees, and is caused by epidermal hyperproliferation, and abnormal differentiation and infiltration of inflammatory cells. Psoriasis may also be associated with other inflammatory diseases such as arthritis, Crohn's disease, and HIV infection. Population, family, and twin studies all suggest an important genetic component in the pathogenesis of psoriasis, coupled with environmental triggers such as streptococcal infection and stress.

Psoriasis is one of a number of autoimmune diseases that display significant human leukocyte antigen (HLA) associations. The analysis of population-specific HLA haplotypes has provided evidence that susceptibility to psoriasis is linked to the class I and II major histocompatibility complexes (MUC) on human chromosome 6 (Jenisch et al. (1998) *Am. J. Hum. Genet* 63:191-199). These studies show that psoriasis consists of two distinct disease subtypes (Type I and Type II), which differ in age of onset and in the frequency of HLA types. Type I psoriasis has an age of onset of prior to 40 years and HLA types Cw6, B57, and DR7 are strongly increased. Patients with Type I psoriasis are much more likely to have a positive family history for the disease. In contrast, only about 10% of Cw6-positive individuals develop Type II psoriasis disease, with HLA-Cw2 being over-represented in this group.

Linkage analysis and association studies suggest the presence of a major genetic determinant of psoriasis within the MHC, the strongest candidate gene marker being HLA-C. The most significant association has been shown between HLA-Cw6 and disease Type IA, which has the earliest onset of disease at 0 to 20 years. However, specific involvement of the HLA-Cw6 genotype in disease pathogenesis has yet to be established.

Recently, attention has focussed on non-HLA genes close to HLA-C, in particular the corneodesmosin gene (also known as the S gene), which is located approximately 160 kb telomeric of the HLA-C locus. The corneodesmosin gene consists of 2 exons spanning approximately 5.3 kb of genomic DNA sequence. Two corneodesmosin mRNAs of 2.2 kb and 2.6 kb, resulting from alternative splicing, have been described (Guerrin et al. (1998) *J. Biol. Chem.* 273: 22640-22647). Association studies (Alnini et al. (1999) *Hum. Mol. Genet.* 8:1135-1140) suggest a strong, significant association between a polymorphism at position 1243 of the corneodesmosin-gene and psoriasis. A corneodesmosin gene haplotype was subsequently defined, which by TDT analysis was shown to have a strong, significant association with psoriasis (Allen et al. (1999) *Lancet* 353:1589-90).

In human epidermis and other cornified squamous epithelia, corneodesmosin is located in the desmosomes of the upper living layers, and in related structures of the cornified layers, the corneodesmosomes. During maturation of the cornified layers, the protein undergoes a series of cleavages, thought to be a prerequisite of desquamation (shedding of the cuticle or epidermis). Corneodesmosin is detected as a glycosylated and phosphorylated basic protein with an apparent molecular mass of 52-56 kDa. During stratum corneum maturation, corneodesmosin is progressively proteolysed until desquamation occurs. In superficial corneocytes, the 52-56 kDa form is no longer detected and immunoreactive fragments of 45 to 30 kDa predominate; Since location, biochemical characteristics and processing of corneodesmosin are similar in several mammals, it is likely that the protein is essential for the function of corneodesmosomes and corneocyte cohesion. It has been shown that expression of the 56 kDa epidermal keratin polypeptide is increased in psoriatic lesions compared with normal skin and transformation of desmosomes into corneodesmosomes is altered in psoriatic epidermis.

Psoriasis affects approximately 6.4 million people in the US and causes varying ranges of physical discomfort, pain and disability. At present, the causes of psoriasis are unknown. There is no specific test for psoriasis or susceptibility thereto, and diagnosis is based solely on clinical examination and skin histopathology.

It is likely that corneodesmosin is implicated in a range of skin diseases, including psoriasis. In this text, diseases in which corneodesmosin is implicated in the pathology will be referred to as "corneodesmosin-mediated disease".

The present invention aims to overcome or ameliorate previous limitations in the art by providing means and methods for the detection and treatment of individuals having, or being susceptible to, corneodesmosin mediated disease, in particular inflammatory conditions such as psoriasis.

In a first aspect, the present invention provides an isolated or recombinant polynucleotide comprising a nucleic acid sequence encoding the corneodesmosin gene of FIG. 1, wherein said nucleic acid sequence comprises a nucleotide substitution, deletion or insertion at one or more positions 6984, 7068, 7077, 7107, 7164, 8884, 8906, 8931, 9538, 9607, 9608, 9647, 9667, 9745, 9761, 9926, 9952, 9968, 10082, 10161, 10162, 10363, 11567, 11641, 11649, 11808, 11839, 11885, 11977, 12018, 12136, 12149, 12198, 12283, 12318, 12345, 12373, 12901, 13001, 13020, 13108, 13117, 13178, 13224, 13316, 13365, 13562, 13605, 13670, 13859, 13889 and 13914 of FIG. 1. (corresponding to positions 284, 368, 377, 407, 464, 2184, 2206, 2231, 2838, 2907, 2908, 2967, 3045, 3061, 3226, 3252, 3268, 3382, 3461, 3462, 3663, 4867, 4941, 4949, 5108, 5139, 5185, 5277, 5318, 5436, 5449, 5498, 5583, 5618, 5645, 5673, 6201, 6301, 6320, 6408, 6417, 6778, 6524, 6616, 6665, 6862, 6905, 6970, 7159, 7189 and 7214 of SEQ ID NO: 1). These novel polymorphisms in the corneodesmosin gene, at the positions indicated above, may be responsible for corneodesmosin mediated disease. In particular, the polymorphisms of the present invention may be useful in identifying individuals susceptible or resistant to corneodesmosin-mediated disease, and in the diagnosis or treatment of such conditions. Preferred combinations of the polymorphisms of the invention are the haplotypes shown in Tables 10a and b. The most preferred haplotype is B of Table 10a.

The polynucleotide of this invention is preferably DNA, or may be RNA or other options.

By "isolated" is meant a polynucleotide sequence which has been purified to a level sufficient to allow allelic discrimination. For example, an isolated sequence will be substantially free of any other DNA or protein product. Such isolated sequences may be obtained by PCR amplification, cloning techniques, or synthesis on a synthesiser. By recombinant is meant polynucleotides which have been recombined by the hand of man.

The corneodesmosin gene sequence shown in FIG. 1 (SEQ ID NO:1) refers to the genomic clone of corneodesmosin, detailed in GenBank Accession No. AC006163 (a genomic clone of the MHC region on chromosome 6p21.3). The single nucleotide polymorphisms of the invention are shown in bold type and underlined on this figure, and have each been given a positional reference with respect to this figure. For reference and comparison with prior art publications, the positional references with respect to the coding sequence have also been given in Table 6, column 2, where nucleotide position 1 corresponds to the first nucleotide of exon 1 and nucleotides upstream of this are given a negative prefix.

A polymorphism is typically defined as two or more alternative sequences, or alleles, of a gene in a population. A polymorphic site is the location in the gene at which divergence in sequence occurs. Examples of the ways in which polymorphisms are manifested include restriction fragment length polymorphisms, variable number of tandem repeats, hypervariable regions, minisatellites, di- or multi-nucleotide repeats, insertion elements and nucleotide deletions, additions or substitutions. The first identified allele is usually referred to as the reference allele, or the wild type. Additional alleles are usually designated alternative or variant alleles. Herein, the sequence exactly as shown in FIG. 1 is designated the reference sequence, and is not part of the invention. Nucleic acid sequences of the present invention which differ from the sequence of FIG. 1 (SEQ ID NO:1) at one or more of the positions indicated above may be referred to as variants of FIG. 1 (SEQ ID NO:1).

A single nucleotide polymorphism is a variation in sequence between alleles at a site occupied by a single nucleotide residue. Single nucleotide polymorphisms (SNP's) arise from the substitution, deletion or insertion of a nucleotide residue at a polymorphic site. Typically, this results in the site of the variant sequence being occupied by any base other than the reference base. For example, where the reference sequence contains a "T" base at a polymorphic site, a variant may contain a "C", "G" or "A" at that site. Single nucleotide polymorphisms may result in corresponding changes to the amino acid sequence. For example, substitution of a nucleotide residue may change the codon, resulting in an amino acid change. Similarly, the deletion or insertion of three consecutive bases in the nucleic acid sequence may result in the insertion or deletion of an amino acid residue. For ease of reference, where a single nucleotide polymorphism of the present invention results in the insertion or deletion of a nucleotide or amino acid residue, the numbering system of FIGS. 1 (SEQ ID NO:1) and 2 (SEQ ID NO:2) have been maintained.

The single nucleotide polymorphisms of the present invention which occur within the protein coding sequence may contribute to the phenotype of an organism by affecting protein structure or function. The effect may be neutral, beneficial or detrimental, depending upon the circumstances. Whatever the effect, the identification of such polymorphisms enables for the first time determination of susceptibility to disease, and new methods of treatment. The single nucleotide polymorphisms of the invention which occur in the non-coding 5' or 3' untranslated regions, may not affect protein sequence, but may exert phenotypic effects by influencing replication, transcription and/or translation. A polymorphism may affect more than one phenotypic trait or may be related to a specific phenotype. In the present invention, polymorphisms in the corneodesmosin gene are likely to affect the phenotype of an individual with respect to corneodesmosin-mediated disease, such as inflammatory disease, in particular psoriasis.

The single nucleotide polymorphisms of the corneodesmosin gene, including those of the present invention, are listed in Table 6 where:

Column 1 designates each single nucleotide polymorphism a reference number.

Column 2 provides the positional reference of the polymorphism with respect to FIG. 1.

Column 3 indicates position of the SNP with respect to the corneodesmosin coding sequence.

Column 4 shows the location of the polymorphisms in the gene.

Column 5 shows the sequence flanking the polymorphism, the polymorphism itself being shown in bold type. For example, the polymorphism at position 6984 is shown as C/T, meaning that the variant sequence comprises a T residue, rather than the native C residue.

Column 6 denotes the standard IUB code.

Column 7 denotes the SEQ ID NO of the corresponding flanking sequence.

As discussed above, where a single nucleotide polymorphism of the present invention comprises a nucleotide substitution, the substitution may comprise the replacement of the reference base at a polymorphic site with any other base. Each single nucleotide polymorphism described in Table 6, column 4 represents a preferred embodiment of the invention.

It will be appreciated by those skilled in the art that corneodesmosin gene sequences of the invention may comprise one or more nucleotide substitutions, deletions or insertions in addition to one or more of the single nucleotide polymorphisms of the invention.

In a second aspect, fragments of the above polynucleotides are provided, which comprise one or more nucleotide substitutions, insertions or deletions at one or more of the above mentioned positions of FIG. 1 (SEQ ID NO:1). Preferably, a fragment may comprise, or even consist of, the polynucleotide sequence of Table 6, column 4. The novelty of a fragment according to the present embodiment may be easily ascertained by comparing the nucleotide sequence of a fragment with sequences catalogued in databases such as GenBank, or by using computer programs such as DNASIS (Hitachi Engineering, Inc.) or Word Search or FASTA of the Genetic Computer Group (Madison, Wis.).

Preferably, the fragments do not encode a full length protein, as is generally the case with the aforementioned polynucleotides, but otherwise satisfy the requirements of the first aspect. Preferred fragments may be 10 to 150 nucleotides in length. More preferably, the fragments are between 5 to 10, 5 to 20, 10 to 20, 20 to 50, or 50 to 100 nucleotides in length. For example, the fragments may be 5, 8, 10, 12, 15, 18, 20, 22, 25, 28, 30, or 35 nucleotides in length. The fragments may be useful in a variety of diagnostic, prognostic or therapeutic methods, or may be useful as research tools for example in drug screening.

In a third aspect of the invention, there is provided non-coding, complementary sequences which hybridise to the corneodesmosin gene sequence. Such "anti-sense" sequences are useful as probes or primers for-detecting an allele of a polymorphism of the invention, or in the regulation of the corneodesmosin gene. They may also be used as agents for use in the identification and/or treatment of individuals having or being susceptible to corneodesmosin mediated disease.

The anti-sense sequences of the invention include those which hybridise to an allele of a polymorphism of the invention, and also those which hybridise a region flanking the polymorphic site to enable amplification of an allele of one or more polymorphisms. These sequences may be useful as probes or primers. To be useful as a probe, the anti-sense sequence should bind preferentially one allele of one or more polymorphisms of the present invention and will, preferably, comprise the exact complement of one allele of one or more polymorphisms of the invention. Thus, for example, where the variant comprises a "G" residue at position 7068 of FIG. 1 corresponding to posittion 368 of SEQ ID NO:1), it is preferred that the anti-sense sequence will comprise a "C" residue. Such anti-sense sequences which are capable of specific hybridisation to detect a single base mis-match may be designed according to methods known in the art and described in Maniatis et al., *Molecular Cloning: A Laboratory Manual* $2^{nd}$ Edition (1989), Cold Spring Harbor, N.Y. and Berger et al., Methods in Enzymology 152: Guide to Molecular Cloning Techniques (1987) Academic Press Inc. San Diego, Calif.; Gibbs et al., *Nuc Acids Res.*, 17: 2437 (1989); Kwok et al., *Nuc Acids Res* 18: 999; and Miyada et al., *Methods Enzymol.* 154: 94 (1987). Variation in the sequence of these anti-sense sequence is acceptable for the purposes of the present invention, provided that the ability of the anti-sense sequence to distinguish between alleles of a polymorphism is not compromised. Similarly, variation in the sequence of a primer sequence is acceptable, provided its ability to mediate amplification of a polymorphic site is not compromised. Preferably, a primer sequence will hybridise to the corneodesmosin gene under stringent conditions which are defined below.

In relation to the present invention, "stringent conditions" refers to the washing conditions used in a hybridisation protocol. In general, the washing conditions should be a combination of temperature and salt concentration so that the denaturation temperature is approximately 5 to 20° C. below the calculated $T_m$ of the nucleic acid under study. The $T_m$ of a nucleic acid probe of 20 bases or less is calculated under standard conditions (1M NaCl) as [4° C.x(G+C)+2° C.x(A+T)], according to Wallace rules for short oligonucleotides. For longer DNA fragments, the nearest neighbour method, which combines solid thermodynamics and experimental data may be used, according to the principles set out in Breslauer et al., *PNAS* 83: 3746-3750 (1986). The optimum salt and temperature conditions for hybridisation may be readily determined in preliminary experiments in which DNA samples immobilised on filters are hybridised to the probe of interest and then washed under conditions of different stringencies. While the conditions for PCR may differ from the standard conditions, the $T_m$ may be used as a guide for the expected relative stability of the primers. For short primers of approximately 14 nucleotides, low annealing temperatures of around 44° C. to 50° C. are used. The temperature may be higher depending upon the base composition of the primer sequence used.

The anti-sense polynucleotides of this embodiment may be the full length of the corneodesmosin gene of FIG. 1 (SEQ ID NO:1), or more preferably may be 5 to 200 nucleotides in length. Preferred polynucleotides are 5 to 10, 10 to 20, 20 to 50, 50 to 100 or 100 to 200 nucleotides in length. Primers, in particular, are typically 10 to 15 nucleotides long, and may occasionally be 16 to 25.

In a preferred embodiment; the polynucleotides of the aforementioned aspects of the invention may be in the form of a vector, to enable the in vitro or in vivo expression of the polynucleotide sequence. The polynucleotides may be operably linked to one or more regulatory elements including a promoter; regions upstream or downstream of a promoter such as enhancers which regulate the activity of the promoter; an origin of replication; appropriate restriction sites to enable cloning of inserts adjacent to the polynucleotide sequence; markers, for example antibiotic resistance genes; ribosome binding sites: RNA splice sites and transcription termination regions; polymerisation sites; or any other element which may facilitate the cloning and/or expression of the polynucleotide sequence. Where two or more polynucleotides of the invention are introduced into the same vector, each may be controlled by its own regulatory sequences, or all sequences may be controlled by the same regulatory sequences. In the same manner, each sequence may comprise a 3' polyadenylation site. The vectors may be introduced into microbial, yeast or animal DNA, either chromosomal or mitochondrial, or may exist independently as plasmids. Examples of suitable vectors will be known to persons skilled in the art and include pBluescript II, LambdaZap, and pCMV-Script (Stratagene Cloning Systems, La Jolla (USA))

Appropriate regulatory elements, in particular, promoters will usually depend upon the host cell into which the expression vector is to be inserted. Where microbial host cells are used, promoters such as the lactose promoter system, tryptophan (Trp) promoter system, β-lactamase promoter system or phage lambda promoter system are suitable. Where yeast cells are used, preferred promoters include alcohol dehydrogenase I or glycolytic promoters. In mammalian host cells, preferred promoters are those derived from immunoglobulin genes, SV40, Adenovirus, Bovine Papilloma virus etc. Suitable promoters for use in various host cells would be readily apparent to a person skilled in the art (See, for example, Current Protocols in Molecular Biology Edited by Ausubel et al, published by Wiley).

In a fourth aspect of the present invention there is provided a protein or protein fragment comprising an amino acid substitution, deletion or insertion at one or more of positions 18, 130 or 180 of the amino acid sequence of FIG. 2 (SEQ ID NO:2). Preferably, the protein or protein fragment is encoded by a polynucleotide according to the first aspect of the invention, and comprises a nucleotide insertion, deletion or substitution at one or more of positions 7164, 10082, 10161, 10162 and 10363 of FIG. 1. corresponding to positions 464, 3382, 3461, 3462, and 3663 of (SEQ ID NO:1, respectively). The corneodesmosin protein or protein fragments of the invention may comprise one or more polymorphisms in addition to one or more of the above-mentioned polymorphisms of FIG. 2.

The amino acid sequence exactly as shown in FIG. 2 (SEQ ID NO:2) may be referred to as the reference sequence, and is not part of the invention. The amino acid sequence of FIG. 2 (SEQ ID NO:2) having an amino acid substitution, deletion or insertion at one or more of the positions indicated above may be referred to as a variant of FIG. 2 (SEQ ID NO:2). The reference amino acid at one or more of the above polymorphic sites may be replaced by any other amino acid residue to produce a variant sequence. Amino acid sequences of FIG. 2 (SEQ ID NO:2) having one or more of the polymorphisms disclosed in Table 4 are each preferred embodiments of the invention.

Protein fragments may be functional or non-functional and may be useful in drug screening or gene therapy. Functional fragments may be defined as those which have characteristics of the corneodesmosin protein. The fragments may be at least 10, preferably at least 15, 20, 25, 30, 35, 40 or 50 amino acids in length.

In a fifth aspect of the present invention, there are provided antibodies which react with an antigen of a protein or protein fragment of the fourth aspect. Antibodies can be made by the procedure set forth by standard procedures (Harlow and Lane, "Antibodies; A Laboratory Manual" Cold Spring Harbor Laboratory, Cold Spring Harbor, N.Y., 1998). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen DNA clone libraries for cells secreting the antigen. Those positive clones can then be sequenced as described in, for example, Kelly et al., Bio/Technology 10:163-167 (1992) and Bebbington et al., Bio/Technology 10:169-175 (1992). Preferably, the antigen being detected and/or used to generate a particular antibody will include proteins or protein fragments according to the fourth aspect.

In a sixth aspect of the present invention, there is provided host cell comprising a polynucleotide according to any of the aforementioned aspects, for expression of the polynucleotide. The host cell may comprise an expression vector, or naked DNA encoding said polynucleotides. A wide variety of suitable host cells are available, both eukaryotic and prokaryotic. Examples include bacteria such as *E. coli*, yeast, filamentous fungi, insect cells, mammalian cells, preferably immortalised, such as mouse, CHO, HeLa, myeloma or Jurkat cell lines, human and monkey cell lines and derivatives thereof. Such host cells are useful in drug screening systems to identify agents for use in diagnosis or treatment of individuals having, or being susceptible to corneodesmosin mediated disease.

The method by which said polynucleotides are introduced into a host cell will usually depend upon the nature of both the vector/DNA and the target cell, and will include those known to a person skilled in the art. Suitable known methods include fusion, conjugation, transfection, transduction, electroporation or injection, as described in Sambrook et al.

In an seventh aspect of the present invention, there is provided a transgenic non-human animal comprising a polynucleotide according to an aforementioned aspect of the invention. Preferably, the transgenic, non-human animal comprises a polynucleotide according to the first or second aspects. The transgenic animal may be either homozygous or heterozygous for the variant sequence. The animal, and cells derived therefrom, are useful for screening biologically active agents that may modulate corneodesmosin function. Such screening methods are of particular use for determining the specificity and action of potential therapies for corneodesmosin mediated disease; such as psoriasis. The animals are useful as a model to investigate the role of corneodesmosin in normal skin function. Transgenic non-human animals are also useful for the analysis of the single nucleotide polymorphisms and their phenotypic effect.

Expression of a polynucleotide of the invention in a transgenic non-human animal is usually achieved by operably linking the polynucleotide to a promoter and/or enhancer sequence, preferably to produce a vector of the fourth aspect, and introducing this into an embryonic stem cell of a host animal by microinjection techniques (Hogan et al., A Laboratory Manual, Cold Spring harbour and *Capecchi Science* (1989) 244: 1288-1292). Preferably, the construct to be introduced into the animal additionally comprises a) a first homology region with substantial identity to a first corneodesmosin gene sequence; and b) a second homology with substantial identity to a second corneodesmosin gene sequence. The first and second homology regions are of sufficient length for homologous recombination to occur with an endogenous corneodesmosin gene. Those embryonic stem cells comprising the desired polynucleotide sequence may be selected, usually by monitoring expression of a marker gene, and used to generate a non-human transgenic animal. Preferred host animals include mice and other rodents. Further development of such an embryonic stem cell may produce a transgenic animal having cells that are descendant from the embryonic stem cell and thus carry the variant sequence in their genome. Such animals can then be selected and bred to produce animals having the variant sequence in all somatic and germ cells. Such mice can then be bred to homozygosity.

In a preferred embodiment, the transgenic non-human animal may comprise an anti-sense nucleic acid sequence of the third aspect. The expression of an anti-sense sequence in a transgenic non-human animal may be useful in determining the effects of such sequences in treating corneodesmosin-mediated disease, or in neutralising deleterious effects of variant corneodesmosin genes in an animal. Preferably, the host animal will be one which suffers from corneodesmosin mediated disease. The disease may be naturally occurring or artificially introduced.

In some preferred embodiments, for example where the mediated disease has been artificially induced, the transgenic non-human animal will be modulated to no longer expresses the endogenous corneodesmosin gene. Such animals may be referred to as "knock out". In some cases, it may be appropriate to modulate the expression of the endogenous corneodesmosin gene, or express the polynucleotides of the present invention, in specific tissues. This approach removes viability problems if the expression of a gene is abolished or induced in all tissues. Preferably, the specific tissue would be skin. Where the heterologous gene is human, the animal may be useful in identifying agents which inhibit expression or activity of the variant corneodesmosin sequences of the invention, either in vivo or in vitro.

In an eighth aspect of the present invention there is provided a method of screening for agents for use in the prognosis, diagnosis or treatment of individuals having, or being susceptible to, corneodesmosin-mediated disease, said method comprising contacting a putative agent with a polynucleotide or protein according to an aforementioned aspect of the present invention, and monitoring the reaction there between. Preferably, the method further comprises contacting a putative agent with a reference polynucleotide or protein of FIG. 1 or 2 (SEQ ID NO:1or (SEQ ID NO:2) respectively, and comparing the reaction between (i) the agent and the polynucleotide or protein encoding the reference allele; and (ii) the agent and polynucleotide or protein of the invention. Potential agents are those which react differently with a variant of the invention and a reference allele. It is envisaged that the present method may be carried out by contacting a putative agent with a host cell or transgenic non-human animal comprising a polynucleotide or protein according to the invention. Putative agents will include those known to persons skilled in the art, and include chemical or biological compounds, such as anti-sense polynucleotide sequences, complementary to the coding sequences of the first aspect, or polyclonal or monoclonal antibodies which bind to a product such as a protein or protein fragment of the second aspect. The agents identified in the present method may be useful in determining susceptibility to corneodesmosin-mediated disease, or in the diagnosis, prognosis or treatment of said disease.

In a ninth aspect of the present invention, there is provided a method of diagnosing, or determining susceptibility of a subject to corneodesmosin-mediated disease, said method comprising determining which allele of one or more of the polymorphisms of the invention is present in a subject. The above method may be used in diagnosing or determining susceptibility of a subject to any disease in which corneodesmosin is implicated in the pathology, in particular inflammatory disease, such as psoriasis. The method of the ninth aspect may also be used to identify the presence of a combination of single nucleotide polymorphisms in a subject which define a haplotype linked to corneodesmosin mediated disease. The haplotype may be any particular combination of the above single nucleotide polymorphisms, optionally including known polymorphisms. Preferred haplotypes are those shown in Table 10a, the most preferred haplotype being B of Table 10a.

Any method, including those known to persons skilled in the art, may be used to determine which allele of one or more polymorphisms of the invention is present. Preferably, the method comprises first removing a sample from a subject. More preferably, the method comprises isolating from a sample a polynucleotide or protein to determine therein which allele of one or more polymorphisms of the invention is present.

Any biological sample comprising cells containing nucleic acid or protein is suitable for this purpose. Examples of suitable samples include whole blood, semen, saliva, tears, buccal, skin or hair. For analysis of cDNA, mRNA or protein, the sample must come from a tissue in which the corneodesmosin gene is expressed, and thus it is preferable to use skin samples.

In a preferred embodiment, the method for diagnosing, or determining susceptibility of a subject to a corneodesmosin-mediated disease, comprises determining which allele of one or more polymorphisms of the invention is present, in a polynucleotide. Any method for determining alleles in a polynucleotide may be used, including those known to persons skilled in the art. Preferably, the method may comprise the use of anti-sense polynucleotides, as defined above. Such polynucleotides may include sequences which are able to distinguish between alleles of one or more polymorphisms of the invention, by preferential binding, and sequences which hybridise under stringent conditions to a region either side of a polymorphism of the invention to enable amplification of one or more of the polymorphisms.

Methods of this embodiment include those known to persons skilled in the art, for example direct probing, allele specific hybridisation, PCR methodology including Allele Specific Amplification (ASA), and RFLP.

Determination of an allele of a polymorphism using direct probing involves the use of anti-sense sequences of the third aspect of the invention. These may be prepared synthetically or by nick translation. The anti-sense probes may be suitably labelled using, for example, a radiolabel, enzyme label, fluoro-label, biotin-avidin label for subsequent visualization in, for example, a southern blot procedure. A labelled probe may be reacted with a sample DNA or RNA, and the areas of the DNA or RNA which carry complimentary sequences will hybridise to the probe, and become labelled themselves. The labelled areas may then be visualized, for example by autoradiography.

Allele specific amplification (ASA) discriminates between alleles of a polymorphism on the basis of primers which carry 3' nucleotides specific for a particular polymorphism. Typically, first and second forward primers are provided, wherein the first forward primer hybridises to one allele of a polymorphism of the invention, and the second forward primer comprises a mis-match at the polymorphic site, thus preventing hybridisation. These primers are used in combination with a backward primer, which hybridises to a distal site to enable amplification of the region between a forward primer and the backward primer. As the first forward primer will only bind to a polymorphic site with which it exhibits perfect complementarity, amplification of the region between the forward and backward primers will indicate the presence of a particular allele. The second forward primer having a is-match at the polymorphic site will not hybridise to the particular allele of a polymorphism, and the absence of a amplification product when this primer is used indicates the absence of the polymorphism. Preferably, the forward primer will be an anti-sense sequence according to the third aspect of the invention. Preferably, the first forward primer will comprise the complement of a single nucleotide polymorphism of the invention at the 3' most position. The backward primer may hybridise to any suitable portion of the corneodesmosin gene to enable amplification of the intervening region. (see, for example, WO93/22456)

Thus, in a preferred embodiment there is provided a method for diagnosing or determining susceptibility of a subject to corneodesmosin-mediated disease, said method comprising removing a sample from a subject and isolating the nucleic acid therefrom; contacting the sample with either a forward primer which preferentially hybridises to one allele of one or more polymorphisms of the present invention or a forward primer which comprises a mis-match at the polymorphic site and does not hybridise thereto, and a backward primer which hybridises to a distal site; subjecting the nucleic acid sample to amplification; and monitoring for presence of an amplification product which is indicative of the presence of a particular allele of one or more of the polymorphisms of the invention. Preferably, a first reaction is performed using one of the forward primers, and a control reaction is then performed using the other forward primer. It is envisaged that a number alleles of the single nucleotide polymorphisms of the invention may be detected in a single reaction by using multiple primer pairs. Amplification products may then be distinguished by size, using techniques known in the art such as gel electrophoresis, or southern blotting. This method allows the unambiguous identification of individuals homozygous for either allele as well as heterozygous individuals.

"RFLP" refers to restriction fragment length polymorphism and is defined as a method of discriminating between two alleles based upon differences in sequence which result in the presence or absence of a restriction enzyme recognition site. In a preferred embodiment of the present aspect there is provided a method for diagnosing or determining susceptibility to corneodesmosin-mediated disease, said method comprising removing a nucleic acid sample from a subject, and contacting with one or more appropriate restriction enzymes. The size of fragments produced is indicative of which allele of one or more single nucleotide polymorphism according to the invention is present. An allele of a polymorphism of the invention may naturally produce a restriction enzyme site, thus allowing for determination of its presence by analysis of the restriction fragments produced. In some cases, however, an allele of a polymorphism does not create a restriction enzyme site, and one must be artificially introduced. This may be done by using a suitable mis-match primer, according to methods known in the art.

The appropriate restriction enzyme, will, of course, be dependent upon the polymorphism and restriction site, and will include those known to persons skilled in the art. Preferred restriction enzymes are listed in Table 3 (ii), column 11, with the expected fragments sizes in columns 7, 8 and 9. Analysis of the digested fragments may be performed using any method in the art, for example gel analysis, or southern blots.

Preferably, the method may first comprise the amplification of a region of the corneodesmosin gene containing one or more of the polymorphic sites of the invention, for example, using PCR techniques. The probes of the present invention may be useful for this purpose.

The above described methods may require amplification of the DNA sample from the subject, and this can be done by techniques known in the art, such as PCR (see *PCR Technology: Principles and Applications for DNA Amplification* (ed. H. A. Erlich, Freeman Press, NY 1992; *PCR Protocols: A Guide to methods and Applications* (eds. Innis et al., Academic press, San Diego, Calif. 1990); Mattila et al., *Nucleic Acids Res.* 19-4967 (1991); Eckert et al., *PCR Methods and Applications* 117 (1991) and U.S. Pat. No. 4,683,202. Other suitable amplification methods include ligase chain reaction (LCR) (Wu et al., *Genomics* 4 560 (1989); Landegran et al., *Science* 241 1077 (1988)), transcription amplification (Kwoh et al, *Proc Natl Acad Sci USA* 86 1173 (1989)), self sustained sequence replication (Guatelli et al., *Proc Natl Acad Sci USA* 87 1874,(1990)) and nucleic acid based sequence amplification (NASBA). The latter two methods both involve isothermal reactions based on isothermal transcription which produce both single stranded RNA and double stranded DNA as the amplification products, in a ratio of 30 or 100 to 1, respectively.

It may often be desirable to identify the presence of multiple single nucleotide polymorphisms in a sample from a subject. This may be the case in the present invention where the corneodesmosin gene contains 39 polymorphisms, each of which may be indicative of a different phenotype. For this purpose, nucleic acid arrays may be useful, as described in WO95/11995. The array may contain a number of probes, each designed to identify one or more of the above single nucleotide polymorphisms of the corneodesmosin gene, as described in WO95/11995.

In a further preferred embodiment of the ninth aspect, the method may comprise determining which allele of one or more polymorphisms is present in a protein of the invention Any method for determining the presence of a particular form, or allele, of a protein is present, may be used. One such method involves the use of antibodies in diagnosing or determining susceptibility to corneodesmosin mediated disease. The method may comprise removing a sample from a subject, contacting the sample with an antibody to an antigen of a protein or protein fragments according to the second aspect of the present invention, and detecting binding of the antibody to the antigen, wherein binding is indicative of the presence of a particular allele or form of the protein and thus risk to corneodesmosin mediated disease. Tissue samples as described above are suitable for this method.

The detection of binding of the antibody to the antigen in a sample may be assisted by methods known in the art, such as the use of a secondary antibody which binds to the first antibody, or a ligand. Immunoassays including immunofluorescence assays (IFA) and enzyme linked immunosorbent assays (ELISA) and immunoblotting may be used to detect the presence of the antigen. For example, where ELISA is used, the method may comprise binding the antibody to a substrate, contacting the bound antibody with the sample containing the antigen, contacting the above with a second antibody bound to a detectable moiety (typically an enzyme such as horse radish peroxidase or alkaline phosphatase), contacting the above with a substrate for the enzyme, and finally observing the colour change which is indicative of the presence of the antigen in the sample.

In a tenth aspect of the invention, there is provided a method of treating a subject who has been diagnosed as having, or being susceptible to, corneodesmosin mediated disease such as psoriasis. The mode of treatment will depend upon the nature of the polymorphism(s) and the phenotypic effect, and preferably comprises negating the effect of the disease causing polymorphism(s). Where a subject has been diagnosed according to the methods of the invention, treatment to negate the effect of the disease causing polymorphism may include any suitable means. A suitable treatment includes the administration of a polynucleotide sequence which hybridises, preferably under stringent conditions (as defined above), to the corneodesmosin gene. Such polynucleotide sequences may include the anti-sense sequences of the third aspect. Alternatively, the treatment may comprise a polynucleotide sequence encoding the corneodesmosin gene or a fragment thereof, and having either a reference or variant allele of a polymorphism of the invention. Preferably, the method, comprises:

(i) determining which allele of one or more polymorphisms of the invention are present; and (ii) administering a polynucleotide sequence which hybridises under stringent conditions to the corneodesmosin gene; or a polynucleotide sequence encoding the reference sequence of the corneodesmosin gene or a fragment thereof, or a polynucleotide sequence of the first aspect.

In an alternative embodiment of this aspect, there is provided the use of a polynucleotide sequence of the tenth aspect in the manufacture of a medicament for use in the diagnosis and treatment of corneodesmosin mediated disease.

This method of diagnosis and treatment may comprise determining and introducing alleles in the form of a polynucleotide or protein. In the above embodiments, the allele of a polymorphism may be determined using any method, as discussed above. The treatment may be introduced in the form of a protein, or polynucleotide. Any suitable means for introduction of a protein may be used. Introduction of a polynucleotide may use gene therapy methods including those known in the art. In general, a polynucleotide encoding the allele will be introduced into the target cells of a subject, usually in the form of a vector and preferably in the form of a pharmaceutically acceptable carrier. Any suitable delivery vehicle may be used, including viral vectors, such as retroviral vector systems which can package a recombinant genome. The retrovirus could then be used to infect and deliver the polynucleotide to the target cells. Other delivery techniques are also widely available, including the use of adenoviral vectors, adeno-associated vectors, lentiviral vectors, pseudotyped retroviral vectors and pox or vaccinia virus vectors. Liposomes may also be used, including commercially available liposome preparations such as Lipofectin®, Lipofectamine®, (GIBCO-BRL, Inc. Gaitherburg, Md.), Superfect® ((Qiagen Inc, Hilden, Germany) and Transfectam® (Promega Biotec Inc, Madison Wis.).

The polynucleotide or vehicle may be administered parenterally (eg, intravenously), transdermally, by intramuscular injection, topically or the like. As corneodesmosin mediated diseases are usually manifested in the skin, topical administration is preferred. The exact amount of polynucleotide or vehicle to be administered will vary from subject to subject and will depend upon age, weight, general condition, and severity or mechanism of the disorder.

In a further aspect, the present invention provides a kit for the detection in a subject of a single nucleotide polymorphism according to the present invention. Preferably, the kit will contain polynucleotides according to the aforementioned aspects, most preferably the anti-sense sequences of the third aspect for use as probes or primers; antibodies of the fifth aspect; or restriction enzymes for use in detecting the presence of a polynucleotide, protein or protein fragment of the invention. Preferably, the kit will also comprise means for detection of a reaction, such as nucleotide label detection means, labelled secondary antibodies or size detection means. In yet a flirter preferred embodiment, the polynucleotides, or antibodies may be fixed to a substrate, for example an array, as described in WO95/11995.

The preferred embodiments of each aspect apply to the other aspects of the invention, mutatis mutandis.

The present invention will now be described by way of a non-limiting example, with reference to the following figures in which:

FIG. 1 shows the nucleotide sequence (SEQ ID NO:1) of the genomic clone of the corneodesmosin gene, of GenBank Accession No. AC006163.

FIG. 2 shows the amino acid sequence (SEQ ID NO:2) of the corneodesmosin protein and coding sequence therefor.

EXAMPLES

Determination of Gene Structure

Figure 3:
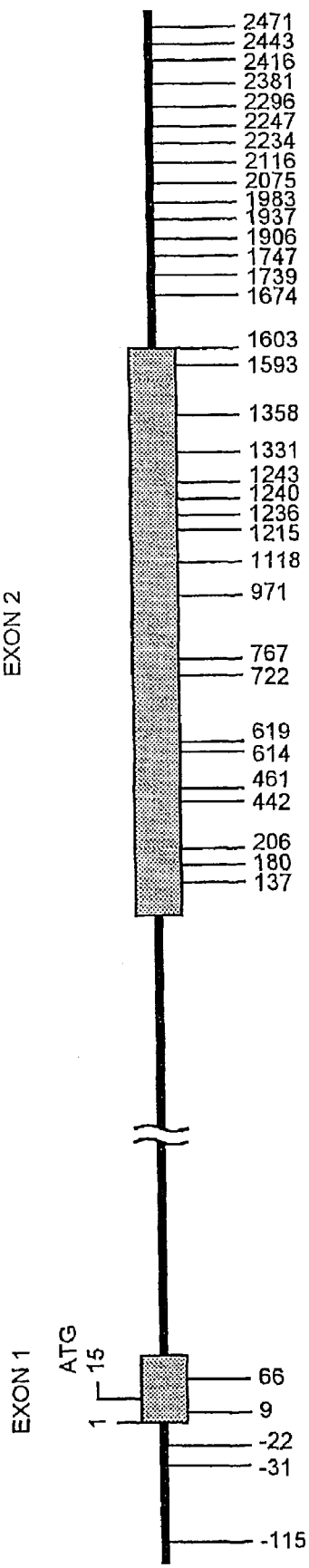
FIG. 3 shows the exon and intron structure of the corneodesmosin gene.

The mRNA sequence of the corneodesmosin gene (GenBank Accession ID NM_001264) was used to screen the following public DNA databases: (available through the National Centre for Biotechnology Information website—http://www.ncbi.nlm.nih.gov/); NR (Non-Redundant DNA), HTGS (High Throughput Genomic Sequence), and GSS (Genome Survey Sequence). The analysis was performed using the BLASTN algorithm (Altschul, et al., (1990) *J. Mol. Biol.* 215-403-410). Any genomic sequences containing the corneodesmosin gene were identified by their degree of sequence identity. The gene structure was determined by comparison of the mRNA sequence with the genomic clones. The deduced exon-intron organisation of the corneodesmosin gene is presented in FIG. 3.

Oligonucleotide Primer Design for Corneodesmosin Gene Sequencing 5 pairs of oligonucleotide primers (S1F/S1R; S2.1F/S2.1R; S2.2F/S2.2R; S2.3F/S2.3R; S2.4F/S2.4R, S2.5F/S2.5R Table 1) were designed to amplify exons 1 and 2 of the corneodesmosin gene including 350 bp 5' untranslated region (UTR) and 909 bp 3' UTR sequences. Oligonucleotide primer sequences were derived from human chromosome 6p21 genomic DNA sequence (GenBank Accession AC006163).

TABLE 1

Oligonucleotide Primer DNA Sequences.

| Primer ID | Primer Sequence | SEQ ID NO |
|---|---|---|
| S 1F | dCTGGGTCCCGTGGCAAGA | 5 |
| S 1R | dGTCCTCTCCCGGAGTCTC | 6 |
| S 2.1F | dGGTGAGGGAGGAAGCCAAG | 7 |
| S 2.1R | dGAGCTGACGCTTTGGCCAC | 8 |
| S 2.2F | dGCCAACCAATGACAACTCTTACC | 9 |
| S 2.2R | dGCCTCCACAGAGCTGGAC | 10 |
| S 2.3F | dGGCAAATACTTCTCCAGCAACC | 11 |
| S 2.3R | dGGCCTTCTCCCATATGGGA | 12 |
| S 2.4F | dCCAAGGAGAGTTACTCGACAG | 13 |
| S 2.4R | dGGCATATTGGGTGGGTTGAC | 14 |
| S 2.5F | dCATCTGGAAACAGTGGCCAC | 15 |
| S 2.5R | dGTCTTCCTCCTCTGTGGGAG | 16 |

Corneodesmosin Gene Amplification

Genomic DNA from a panel of 24 unrelated individuals was amplified using primer pairs S1F/S1R; S2.1F/S2.1R; S2.2F/S2.2R; S2.3F/S2.3R; S2.4F/S2.4R, S2.5F/S2.5 R. 100 ng genomic DNA was amplified by PCR in a total reaction volume of 25 μl containing 50 mM KCl, 20 mM Tris.HCl (pH 8.4), 2 mM MgCl$_2$ 200μM each dATP, dCTP, dGTP, dTTP, 1 μM each oligonucleotide primer and 0.5 units AmpliTaq Gold DNA polymerase (Applied Biosystems). Reactions were thermocycled with an initial denaturation step of 95° C./10 mins followed by 35 cycles of 94° C./30 secs; T$_m$ annealing/30 secs; 72° C./30 secs. A final elongation step of 72° C./10 mins completed the amplification. Annealing temperatures (T$_m$) for specific primer pairs are presented in Table 2.

TABLE 2

Primer Annealing Temperatures and Amplimer Sizes.

| Amplimer | Primer Pairs | Fragment size (bp) | Tm (° C.) |
|---|---|---|---|
| 1 | S1F and S1R | 495 | 63 |
| 2.1 | S2.1F and S2.1R | 610 | 62 |
| 2.2 | S2.2F and S2.2R | 619 | 62 |
| 2.3 | S2.3F and S2.3R | 621 | 63 |
| 2.4 | S2.4F and S2.4R | 532 | 59 |
| 2.5 | S2.5F and S2.5R | 474 | 61 |

Heteroduplex Analysis using DHPLC:

Oligos were designed to amplify products of between 400-800 bp in length from the genomic DNA of 12-25 individuals. Denaturing high-performance liquid chromatography (DHPLC) analysis was performed using the WAVE™ DNA fragment analysis system (Transgenomic) (Kuklin, et al., (1997-98) *Genet Test.* 1(3):, 201-6.). The temperature required for successful resolution of heteroduplex molecules within each PCR product was determined empirically by injecting PCR product at a series of increasing mobile phase temperatures and constructing a fragment specific melting curve. A universal gradient for double stranded DNA was used to determine the appropriate acetonitrile concentration for the heteroduplex identification. For mutation detection, 1-2 µl aliquots of the PCR reactions from each of the eleven individuals were injected onto the WAVE™ column. Mutation detection gradients were for four minutes. Results were graphically visualised using the D-7000 HSM software (Transgenomic).

Direct Sequencing of PCR Products 50-100 ng of PCR products were sequenced in both orientations using the DYEnamic ET terminator cycle sequencing premix kit from Amersham. Reactions were fractionated on ABI 377 automated sequencers using standard procedures. Chromatographic traces were analysed using the SEQUENCHER programme (Gene Codes, USA), to identify SNP positions.

Detection of Variant Alleles—Assay Design for Genotyping

The fragment sequence containing the polymorphism was analysed for the creation or deletion of a naturally occurring restriction enzyme recognition site in response to variation in the nucleotide sequence. If the polymorphism did not result in any changes in restriction enzyme recognition sites then the sequence was interrogated with the Primer Design Mismatch Program™. This is an adaptation of the program described by Davidow L S ((1992) *Comput Appl Biosci* 8:193-194).

Detection of Polymorphisms in 24 Population Controls

The application of the approach outlined above resulted in the identification of 39 SNPs. These are described in Table 3, in which:

Column 1 designates each single nucleotide polymorphism a reference number.

Column 2 provides the positional reference of the polymorphism with respect to FIG. 1, together with details of the polymorphism itself. For example, the reference "C6948T" indicates a substitution of the nucleotide "C" for nucleotide "T" at position 6984 of FIG. 1.

Column 3 of (i) provides the corresponding positional references with respect to the coding sequence of the corneodesmosin gene.

Column 4 of (i) indicates the region of the gene which the polymorphism occurs.

Column 5 of (i) shows the sequence flanking the polymorphism, the polymorphism itself being shown in bold type. The single nucleotide polymorphisms are defined using standard IUB code.

Column 6 of (i) indicates the SEQ ID NO of the corresponding flanking sequence.

Columns 3 and 5 of (ii) show primer sequences which may be used to amplify a region of the corneodesmosin gene to enable detection of the single nucleotide polymorphism by using restriction enzyme analysis. The amplified product size is shown in Column 7 of (ii).

Columns 4 to 6 of (ii) indicate the SEQ ID NO of the corresponding primer sequence.

Columns 8 to 10 of (ii) list the restriction enzymes used to digest the amplified product, and the sizes of fragments generated by the reference, variant and heterozygous sequences respectively.

RFLP or ASA assays were developed for all of these SNPs and the corresponding primers along with amplification product and digestion fragment sizes are also given in Table 3. Of these 39 SNPs, 9 give rise to amino acid changes. These are shown in Table 4.

Additional Corneodesmosin Polymorphisms

In a subsequent experiment, DNAs from 96 individuals comprising 24 type TA psoriatics, 24 type MB psoriatics, 24 type II psoriatics and an additional 24 healthy controls, were sequenced as described above using primers designed to cover the remainder of the Corneodesmosin gene (see Table 5a)

The sequencing reactions were carried out with 50-100 ng of PCR products sequenced in both orientations using the DYEnamic ET terminator cycle sequencing premix kit from Amersham according to the following protocol:

The PCR products were Exo/Sap treated and desalted using p10 columns, prior to setting up the sequencing reactions in a thermowell plate including:

200-400 ng PCR Product

1 µl primer@ 10 pmolml$^{-1}$

8 µl ET Termination mix

H$_2$O to 20 µl

The plates were sealed with an MJ Research Microseal film and then vortexed to mix samples, followed by a spin to ensure reaction is at the bottom of the wells.

PCR was carried out according to the following protocol:

No Predenaturation

95° C. for 30 sec

50° C. for 15 sec

60° C. for 1 min for 40 cycles and then hold at 10° C. until ready to purify.

After removing the plate from the thermocycler, the products were purified by ethanol precipitation. To each well we added 2 µl 7.5M ammonium acetate followed by 80 µl 100% ethanol and incubated at room temperature for 10 minutes before spinning at 4000 rpm for 1 hour at room temperature. The supernatant was discarded and the pellet washed with 70% ethanol before centrifugation for a further 30 minutes. The supernatant was discarded and remaining ethanol removed gently by pipetting using p10 tips before allowing the pellets to air dry.

The samples were then resuspended in 10 µl MegaBACE Loading Buffer (Molecular Dynamics) and transferred to a Robbins plate prior to loading onto the MegaBACE. Reactions were fractionated on a Molecular Dynamics MegaBACE capillary sequencer using standard procedures.

Chromatographic traces were analysed using the SEQUENCHER programme (Gene Codes, USA), to identify SNP positions.

A total of 28 novel SNPs were identified (additional to those given in the example above). For reference, these are SNPs 6-18 and 53-67 in Table 5b. A combined list of Corneodesmosin SNPs is given in Table 6.

Corneodesmosin Gene Association with Psoriasis

A total of 21 SNPs (see Table 7) were genotyped in 147 families identified through a proband with psoriasis (a total of 499 individuals, of whom 233 were affected). The genotyping was carried out using a variety of methods (single base extension using the Snapshot kit from Amersham Pharmacia Biotech, Pyrosequencing (Ahmadian A et al., Anal Biochem 2000 280:103-10), or direct sequencing) as given in Table 7. All these methods used established methodologies that are provided by the equipment manufacturers and/or are well known to those skilled in the art.

Linkage Disequilibrium

The extent of linkage disequilibrium (LD) between markers was calculated using genotype data from 199 unrelated, unaffected individuals and is expressed as correlation coefficients in Table 8. This analysis shows that there is extensive linkage disequilibrium between many of the Corneodesmosin polymorphisms.

Single Point Association

Single point associations between each SNP and psoriasis affected status were calculated using the TRANSMIT program (Clayton D, MRC Biostatistics Unit, Cambridge)—see Table 9. Highly significant associations were observed between SNPs 19, 21, 23, 24, 26, 28, 30, 33, 34, 37, 38 and psoriasis. The single SNP showing the most significant association with psoriasis that has been previously reported is SNP 33 (Tazi Ahnini R et al, Hum. Mol. Genet. 1999: 8 pp 1135-40; Allen M H et al, Lancet 1999: 353 pp1589-90).

This study has identified 9 SNPs, (19, 21, 24, 26, 28, 30, 34, 37 and 38) which show global chi-squared values greater than that seen for SNP 33, and are therefore more powerfully predictive of affected status.

Haplotype Analysis

A total of 19 SNPs were used for haplotype analysis (SNPs at positions 29 and 32 were excluded due to low information content). Three common haplotypes were identified.(Table 10). Of the three common haplotypes, haplotype B is significantly associated with psoriasis. The alleles are coded alphabetically (Table 10b) such that the nucleotide first in the alphabet is given coded as 1, and the other nucleotide is coded as 2. Thus A is always 1, T is always 2, and G or C are coded depending on the other nucleotide. For example, in SNP No. 1, which is a C to T substitution, the presence of the C allele is coded as 1 and the presence of the T allele is coded as 2 (see Table 10b). In Table 10a, this means that haplotypes A and B have C residues, and haplotype C has a T residue at this position. For an A to C substitution, the A allele will be coded as 1, and the C allele as 2. In a C to G substitution, the C allele will be 1 and the G allele 2.

Construction of Corneodesmosin Gene Targeting Vector

As the genetic data pointed strongly to an involvement of the Corneodesmosin gene in the pathophysiology of psoriasis, we decided to engineer mouse strains in which the mouse orthologue of the corneodesmosin gene is knocked out by homologous recombination using a vector construct designed to remove exon 2 of the Corneodesmosin gene.

Murine Corneodesmosin genomic clones were isolated from a mouse large insert PAC library, using mouse Corneodesmosin cDNA sequence as a probe by standard techniques. The isolated murine Corneodesmosin genomic clones were then restriction mapped in the region of the Corneodesmosin gene using small oligonucleotide probes and standard techniques. The murine genomic locus was partially sequenced to enable the design of homologous arms to clone into the targeting vector. The murine Corneodesmosin gene is a two-exon gene. A 4 kb 5' homologous arm and a 1 kb 3' homologous arm where amplified by PCR and the fragment cloned into the targeting vector. The position of these arms was chosen to functionally disrupt the Corneodesmosin gene by deleting the majority of the coding sequence. A targeting vector was prepared where the deleted Corneodesmosin sequence was replaced with non-homologous sequences composed of an endogenous gene expression reporter (an in frame fusion with lacZ) upstream of a selection cassette composed of a self promoted neomycin phosphotransferase (neo) gene in the same orientation as the Corneodesmosin gene.

Transfection and Analysis of Embryonal Stem Cells

Embryonal stem cells (Evans M J & Kaufman M H Nature 1981 292:154-6) were cultured on a neomycin resistant embryonal fibroblast feeder layer grown in Dulbecco's Modified Eagles medium supplemented with 20% Fetal Calf Serum, 10% new-born calf serum, 2 mM glutamine, non-essential amino acids, 100 µM 2-mercaptoethanol and 500 u/ml leukemia inhibitory factor. Medium was changed daily and ES cells were subcultured every three days. 5.times.10.sup.6 ES cells were transfected with 5 µg of linearized plasmid by electroporation (25 µF capacitance and 400 Volts). 24 hours following electroporation the transfected cells were cultured for 9 days in medium containing 200 µg/ml neomycin. Clones were picked into 96 well plates, replicated and expanded before being screened by PCR to identify clones in which homologous recombination had occurred between the endogenous Corneodesmosin gene and the targeting construct. From 96 picked clones 45 targets were identified. These clones where expanded to allow replicas to be frozen and sufficient high quality DNA to be prepared for Southern blot confirmation of the targeting event using external 5' and 3' probes, all using standard procedures (Russ et al. Nature 404:95-99).

Generation of Corneodesmosin Deficient Mice

C57BL/6 female and male mice were mated and blastocysts were isolated at 3.5 days of gestation. 10-12 cells from Clone 7 (described in Example 2) were injected per blastocyst and 7-8 blastocysts were implanted in the uterus of a pseudopregnant F1 female. Five chimeric pups were born of which one male was 100% agouti (indicating cells descendent from the targeted clone). This male chimera was mated with female and MF1 and 129 mice, and germline transmission was determined by the agouti coat color and by PCR genotyping respectively.

Corneodesmosin Knock-out Mouse as a Model of Corneodesmosin-mediated Disease

Mice heterozygous for the Corneodesmosin knockout are superficially normal. Staining for expression of the lacZ reporter gene fused to the Corneodesmosin promoter in the knockout construct shows clear expression in desquamating skin. We then genotyped surviving offspring from intercrosses of heterozygous knockout mice on an outbred genetic background in an attempt to isolate mice homozygous for the knockout.

From 44 surviving progeny we identified:
17 wild type
27 heterozygotes
0 homozygous mutant.

Statistical analysis of these data indicate that the ratio of wild type:heterozygous animals conforms to a 1:2 ratio consistent with a homozygous lethal phenotype (Chi square 0.557).

In keeping with this analysis, two pups found dead 24-48 hours after birth were homozygous mutant. Together these data indicate the Corneodesmosin deficiency in mice is lethal with pups dying soon after birth, most likely through dehydration as a result of failure to establish a permeability barrier in the skin.

We conclude from this that altering the activity of Corneodesmosin (e.g. by modulating expression or altering its proteolytic processing) will be useful in developing models of disease in which epithelial integrity is increased (e.g. psoriasis) or decreased (e.g. dermatitis), and for testing novel agents for the alleviation of Corneodesmosin mediated disease.

TABLE 3

(i) S Gene SNPs with location and assay details

| SNP | SNP nt position | Corneodesmosin nt position | Location | Flanking Sequence | SEQ ID NO |
|---|---|---|---|---|---|
| 1 | C6984T | −115 | 5'UTR | CTCCCGGCCA CACCAACTTC CCCCYGGGCA CCCACCCCCT CCACCTCTCC | 17 |
| 2 | A7068G | −31 | 5'UTR | AATGTCCAGCTCTGGCATAA AGGACCCRGG TGTCCTCGAG CTGCCATCAG | 18 |
| 3 | C7077T | −22 | 5'UTR | TCTGGCATAA AGGACCCAGG TGTCCTYGAG CTGCCATCAG TCAGGAGGCC | 19 |
| 4 | C7107T | 9 | 5'UTR | CTGCCATCAG TCAGGAGGCCGTGCAGYCCC AGATGGGCTC GTCTCGGGCA | 20 |
| 5 | A7164T | 86 | Coding Sequence | GGCGTGTGGGTGGGCACGGG ATGWTGGCAC TGCTGCTGGC TGGTCTCCTC | 21 |
| 6 | C10039T | 137 | Coding Sequence | CTAAGAGCAT TGGCACCTTC TCAGACCCYT GTAAGGACCCCACGCGTATC | 22 |
| 7 | C10082T | 180 | Coding Sequence | ACCTCCCCTAACGACCCCTGCYTCACTGGGAAGGGTG | 23 |
| 8 | C10134T | 206 | Coding Sequence | CAGTAGCTAC AGTGGCTCCA GCAYTTCTGG CAGCTCCATTTCCAGTGCCA | 24 |
| 9 | G10344A | 442 | Coding Sequence | GAGCAGCAGC TCTCACTCGG GAARCAGCGGCTCTCACTCG GAAGCAGCA | 25 |
| 10 | 10363(AAG)ins | 461 | Coding Sequence | GAAGCAGCGGCTCTCACTCG GG(AAG)CAGCA GCTCTCATTCGAGCAGCAGC | 26 |
| 11 | A10516G | 614 | Coding Sequence | CTGGACAAAGCTCTTCCTCT TCCCARACCT CTGGGGTATC CAGCAGTGGC | 27 |
| 12 | C10521T | 619 | Coding Sequence | CTGGACAAAGCTCTTCCTCT TCCCAAACCT YTGGGGTATC CAGCAGTGGC | 28 |
| 13 | T10624C | 722 | Coding Sequence | GGAGGGCCCA TCGTCTCGCA CTCYGGCCCC TACATCCCCA GCTCCCACTC | 29 |
| 14 | G10669A | 767 | Coding Sequence | GCTCCCACTCTGTGTCAGGG GGTCAGAGRC CTGTGGTGGT GGTGGTGGAC | 30 |
| 15 | T10873C | 971 | Coding Sequence | CCTACAGTAA GGGTAAAATC TAYCCTGTGG GCTACTTCAC CAAAGAGAAC | 31 |
| 18 | G11020A | 1118 | Coding Sequence | AGCCAGTCGGCAGCTTCCTC GGCCATTGCR TTCCAGCCAG TGGGGACTGG | 32 |
| 17 | A11117G | 1215 | Coding Sequence | CTCCCTCCAGTTCTCGAGTC CCCAGCRGTT CTAGCATTTC CAGCAGCTCC | 33 |
| 18 | T11138G | 1236 | Coding Sequence | CCCAGCAGTTCTAGCATTTC CAGCAGCKCC GGTTCACCCTACCATCCCTG | 34 |
| 19 | G11142T | 1240 | Coding Sequence | CTAGCATTTC CAGCAGCTCC GKTTCACCCTACCATCCCTGCGGCAGTGCT | 35 |
| 20 | C11145T | 1243 | Coding Sequence | CTAGCATTTC CAGCAGCTCC GGTTYACCCTACCATCCCTGCGGCAGTGCT | 36 |

TABLE 3-continued

| | | | | | |
|---|---|---|---|---|---|
| 21 | G11233C | 1331 | Coding Sequence | GCAGCAGCTC CAGTTCCCAA TCSAGTGGCA AAATCATCCTTCAGCCTTGT | 37 |
| 22 | T11260C | 1358 | Coding Sequence | TCGAGTGGCA AAATCATCCTTCAGCCTTGY GGCAGCAAGT CCAGCTCTTC | 38 |
| 23 | G11495A | 1593 | Coding Sequence | TTCCTACCCC AAGGAGAGTT ACTCRACAGTCCATAAGTCA ACTGTTGTGT | 39 |
| 24 | 11505(AAG)ins | 1603 | 3'UTR | GAGAGTTACTCGACAGTCCATAAG(AAG)TCAACTGTTGTGTGTGTGCATGC | 40 |
| 25 | G11576T | 1674 | 3'UTR | TACACTATATCCCATATGGGAGAAGKCCAGTGCCCAGGCATAGGGTTAGC | 41 |
| 26 | T11641C | 1739 | 3'UTR | CCCAAAAGAGTGGTTCTGCTTTCTCYACTACCCTAAGGTTGCAGACTCTC | 42 |
| 27 | T11649C | 1747 | 3'UTR | AGTGGTTCTGCTTTCTCTACTACCCYAAGGTTGCAGACTCTCTCTTATCA | 43 |
| 28 | T11808G | 1906 | 3'UTR | CCCCTTACAATTCCCTCTACTGTGTKGAAATGGTCCATTGAGTAACACCC | 44 |
| 29 | C11839G | 1937 | 3'UTR | GGTCCATTGAGTAACACCCCCATCASCTTCTCAACTGGGAAACCCCTGAA | 45 |
| 30 | C11885T | 1983 | 3'UTR | TGAAATGCTCTCAGAGCACCTCTGAYGCCTGAAGAAGTTATACCTTCCTC | 46 |
| 31 | C11977T | 2075 | 3'UTR | AAACAGTGGC CACTTTTCAC TGACCTYTCT TCGACATCTA GTCAACCCAC | 47 |
| 32 | T12018C | 2116 | 3'UTR | CAACCCACCCAATATGCCACTGGGCYTTCGCTCCCAATTCCACCCCACCC | 48 |
| 33 | T12136C | 2234 | 3'UTR | TTATCTCAGCCCCTTCCTGTGGCCAYTTCCCTCAGTGCCCAGATGATTCC | 49 |
| 34 | C12149T | 2247 | 3'UTR | TTCCTGTGGCCATTTCCCTCAGTGCYCAGATGATTCCCTGGGTGAGGGAG | 50 |
| 35 | G12198A | 2296 | 3'UTR | GACACTGGGGCACCCTCAGAGGTTGRAGCAGGCTCCCTGCTGTCCCTGGA | 51 |
| 36 | G12283A | 2381 | 3'UTR | GGTGCAGACTTTTTGCCTTCTTGGARTCCTGGGTCTCCCTCTGAGAGTCTG | 52 |
| 37 | T12318C | 2416 | 3'UTR | TCCTCTGAGAGTCTGGGTGGTGCTCYTCCTACGCCTCTAGAGGTCTCTGT | 53 |
| 38 | C12345T | 2443 | 3'UTR | CCTACGCCTCTAGAGGTCTCTGTGTYCCTCATTTTCCTTCAAAAGCGGGC | 54 |
| 39 | G12373A | 2471 | 3'UTR | TCATTTTCCTTCAAAAGCGGGCTGTRTTTCTCTTCTACCTTCCAGCTCCT | 55 |

(ii)

| SNP | SNP nt position | Primer sequence | SEQ ID NO | Primer sequence | SEQ ID NO | PCR product size (bp) |
|---|---|---|---|---|---|---|
| 1 | C6984T | dCTGGGTCCCGTGGCAAGA | 5 | dGTCCTCTCCCGGAGTCTC | 6 | 495 |
| 2 | A7068G | dCTGGGTCCCGTGGCAAGA | 5 | dCTGACTGATGGCAGCTCGAGGACAGC | 58 | 333 |
| 3 | C7077T | dCTGGGTCCCGTGGCAAGA | 5 | dGTCCTCTCCCGGAGTCTC | 6 | 496 |
| 4 | C7107T | dCCCACCCCCTCCACCTCT | 59 | dCCGTCCCCTTCGCTGGGTCCTC | 60 | 283 |
| 5 | A7164T | dATTACCACGCTCCTCCCG | 61 | dGCAGGAGGAGACCAGCCAGCAGCAGTGTCA | 62 | 249 |
| 6 | C10039T | dCAGTTCTTCCTCCTTTCTCCAT | 63 | dAGGGGAGGTGATACGCGTGGGGTCCTTCCA | 64 | 215 |
| 7 | C10082T | dGACCTTGGCTAAGAGCATTG | 65 | dCCTGGCTTAAAAGATCCTGC | 66 | 240 |
| 8 | C10134T | dGGTGAGGGAGGAAGCCAAG | 7 | dAGAACTGCTGGAGCCACTGTAGCTACTGCA | 68 | 193 |
| 9 | G10344A | dCAGCTGGGGAGCAGCAGCTCTCCCTCGGGA | 69 | dGAGCTGACGCTTTGGCCAC | 8 | 243 |
| 10 | 10363(AAG)ins | dAGCGGCTCTCACTCGGGAAG | 71 | dTGACGCTTTGGCCACTGCTG | 72 | 204 |
| | | dAGCGGCTCTCACTCGGGCAG | 73 | | | |
| 11 | A10516G | dCAGCCTGGACAAAGCTCTTCCTCTTCTCA | 74 | dCTGGAAGGCCACCATTGCTA | 75 | 269 |
| 12 | C10521T | dGCCAACCAATGACAACTCTTACC | 9 | dGCCTCCACAGAGCTGGAC | 10 | 620 |
| 13 | T10624C | dCTGCAGTGGAGGGCCCATCGTCTCGCACAC | 78 | dCTGGAAGGCCACCATTGCTA | 79 | 162 |
| 14 | G10669A | dGCCAACCAATGACAACTCTTACC | 76 | dGCCTCCACAGAGCTGGAC | 77 | 620 |

TABLE 3-continued

| | | | | | | |
|---|---|---|---|---|---|---|
| 15 | T10873C | dAGGCATGACCTACAGTAAGGGTAAAATCGA | 80 | dGCCTCCACAGAGCTGGAC | 77 | 221 |
| 16 | G11020A | dCAGCCAGTCGGCAGCTTCCTCGGCCATCGC | 81 | dTGAAGGAGCCGGTGCCTG | 82 | 225 |
| 17 | A11117G | dTGCTCTCCCTCCAGTTCTCGAGTCCCCTGC | 83 | dGTGTCAAGGAGGAGACAGACA | 84 | 231 |
| 18 | T11138G | dGGCAAATACTTCTCCAGCAACC | 11 | dGGCCTTCTCCCATATGGGA | 12 | 622 |
| 19 | G11142T | dGGCAAATACTTCTCCAGCAACC | 11 | dGGCCTTCTCCCATATGGGA | 12 | 622 |
| 20 | C11145T | dGTTCTAGCATTTCCAGCAGCTCCGATT | 87 | dGTGTCAAGGAGGAGACAGACA | 88 | 200 |
| 21 | G11233C | dGGCAAATACTTCTCCAGCAACC | 11 | dGGCCTTCTCCCATATGGGA | 12 | 622 |
| 22 | T11260C | dGGCAAATACTTCTCCAGCAACC | 11 | dGTGACCAGAAGAGCTGGACTTGCTGGC | 89 | 331 |
| 23 | G11495A | dGGCAAATACTTCTCCAGCAACC | 11 | dGGCCTTCTCCCATATGGGA | 12 | 622 |
| 24 | 11505(AAG)ins | dGGAGAGTTACTCGACAGTCCATAAGAAG | 90 | dCAGTAGGAGAGAATCAAGAGAGGAGC | 91 | 259 |
| | | dGGAGAGTTACTCGACAGTCCATAAGTCA | 92 | dCAGTAGGAGAGAATCAAGAGAGGAGC | 91 | |
| 25 | G11576T | dAAGGAGAGTTACTCGACAGTCC | 93 | dAGGAGAGAATCAAGAGAGGAGC | 94 | 254 |
| 26 | T11641C | dAAGGAGAGTTACTCGACAGTCC | 93 | dTAAGAGAGTCTGCAACCTTAGGGTAGC | 95 | 190 |
| 27 | T11649C | dAAGGAGAGTTACTCGACAGTCC | 93 | dAGGAGAGAATCAAGAGAGGAGC | 94 | 254 |
| 28 | T11808G | dAGGTTGCAGACTCTCTCTTATCACCC | 96 | dATGGGGTGTTACTCAATGGACCATGTC | 97 | 186 |
| 29 | C11839G | dAGGTTGCAGACTCTCTCTTATCACCC | 96 | dAAGTGGCCACTGTTTCCAGATGATGG | 98 | 315 |
| 30 | C11885T | dAGGTTGCAGACTCTCTCTTATCACCC | 96 | dAAGTGGCCACTGTTTCCAGATGATGG | 98 | 315 |
| 31 | C11977T | dCCATCATCTGGAAACAGTGG | 99 | dCGTGGTGAGCTCTGTAATGG | 100 | 124 |
| 32 | T12018c | dACCATCATCTGGAAACAGTGGC | 101 | dTGAGCTCTGTAATGGAGGGTGG | 102 | 120 |
| 33 | T12136C | dCCTTATCTCAGCCCCTTCCTGTGGCCT | 103 | dATCTGTCCAGGATCCAGGGACAGC | 104 | 126 |
| 34 | C12149T | dAACACACCCATTGCCTCTCAAG | 105 | dCCACAGTTTACTGAGCCATCTG | 106 | 167 |
| 35 | G12198A | dCCTTATCTCAGCCCCTTCCTGTGGC | 107 | dAGGATCCAGGGACAGCAGGGAGCCTGGT | 108 | 118 |
| 36 | G12283A | dGGACAGATGGCTCAGTAAACTG | 109 | dAGGGACACAGAGACCTCTAG | 110 | 122 |
| 37 | T12318C | dGGACAGATGGCTCAGTAAACTG | 109 | dAGGGACACAGAGACCTCTAG | 110 | 122 |
| 38 | C12345T | dCTCTTCCTACGCCTCTAGAGGTCTCTGGGT | 111 | dGCAATGAGAGAGGAGGGAAATGGCG | 112 | 179 |
| 39 | G12373A | dGTCCCTCATTTTCCTTCAAAAGCGGGCAG | 113 | dGGGAAGAGAATGGATTTCCTGGAGC | 114 | 174 |

| SNP | Enzyme | Allele 1 | Allele 2 | Heterozygate |
|---|---|---|---|---|
| 1 | AvaI | 313, 32, 16, 135 | 220, 93, 32, 16, 135 | 313, 220, 135, 93, 32, 16 |
| 2 | PvuII | 333 | 309, 24 | 333, 309, 24 |
| 3 | TaqI | 496 | 315, 181 | 496, 315, 181 |
| 4 | AvaI | 150, 85, 48 | 150, 85, 32, 16 | 150, 85, 48, 32, 16 |
| 5 | HincII | 249 | 220, 29 | 249, 220, 29 |
| 6 | BstNI | 215 | 184, 31 | 215, 184, 31 |
| 7 | MnlI | 240 | 151, 70, 19 | 240, 151, 70, 19 |
| 8 | PstI | 193 | 163, 30 | 193, 163, 30 |
| 9 | BslI | 243 | 219, 22 | 243, 219, 22 |
| 10 | | 204 | 204 | 204 |
| 11 | DdeI | 269 | 243, 26 | 269, 243, 26 |

TABLE 3-continued

| | | | | |
|---|---|---|---|---|
| 12 | BsnFI | 162 | 132, 30 | 162, 132, 30 |
| 13 | BsmAI | 451, 169 | 401, 169, 50 | 451, 401, 169, 50 |
| 14 | Mbd | 190, 31 | 221 | 221, 190, 31 |
| 15 | MnlI | 62, 270, 45, 186, 57 | 62, 12, 258, 45, 186, 57 | 270, 258, 186, 62, 57, 45, 12 |
| 16 | BstU | 225 | 195, 30 | 225, 195, 30 |
| 17 | PstI | 231 | 199, 32 | 231, 199, 32 |
| 18 | HnaI | 622 | 440, 182 | 622, 440, 182 |
| 19 | MspI | 241, 214, 167 | 181, 60, 214, 167 | 241, 214, 181, 167, 60 |
| 20 | HnfI | 200 | 176, 24 | 200, 176, 24 |
| 21 | TaqI | 146, 389, 87 | 146, 127, 262, 87 | 389, 262, 146, 127, 87 |
| 22 | HnaI | 331 | 304, 27 | 331, 304, 27 |
| 23 | TaqI | 146, 127, 349 | 146, 127, 262, 87 | 349, 262, 146, 127, 87 |
| 24 | | 259 | 259 | 259 |
| 25 | HaeIII | 254 | 96, 158 | 254, 158, 96 |
| 26 | Acl I | 190 | 160, 30 | 190, 160, 30 |
| 27 | Bsu 361 | 254 | 168, 86 | 254, 168, 86 |
| 28 | Hinc II | 186 | 158, 28 | 186, 158, 28 |
| 29 | Alu I | 315 | 252, 63 | 315, 252, 63 |
| 30 | Bsa H | 315 | 234, 81 | 315, 234, 81 |
| 31 | EarI | 124 | 80, 44 | 124, 80, 44 |
| 32 | Ban II | 120 | 80, 38, 2 | 120, 80, 38, 2 |
| 33 | Ear I | 126 | 94, 32 | 126, 94, 32 |
| 34 | BsiHKAI | 167 | 102, 65 | 167, 102, 65 |
| 35 | Sau961 | 118 | 89, 29 | 118, 89, 29 |
| 36 | TfiI | 122 | 67, 55 | 122, 67, 55 |
| 37 | Ear I | 122 | 95, 27 | 122, 95, 27 |
| 38 | Eco0109 I | 179 | 151, 28 | 179, 151, 28 |
| 39 | TspRI | 174 | 141, 33 | 174, 141, 33 |

TABLE 4

Amino Acid Polymorphisms

| SNP | POSITION | LOCATION | VARIANT 1 | VARIANT 2 | Effect on amino acid side chain |
|---|---|---|---|---|---|
| 5 | A7164T | EXON 1 | MET | LEU | Conservative |
| 6 | C10039T | EXON 2 | PRO | PRO | Neutral |
| 7 | C10082T | EXON 2 | LEU | SER | Hydrophobic - Hydrophilic |
| 8 | C10108T | EXON 2 | GLY | GLY | Neutral |
| 9 | G10344A | EXON 2 | SER | ASN | Conservative |
| 10 | 10363 (AAG)ins | EXON 2 | SER insertion | SER deletion | SER insertion/deletion |
| 11 | A10516G | EXON 2 | GLN | GLN | Neutral |
| 12 | C10521T | EXON 2 | SER | PHE | Hydrophilic - Hydrophobic |
| 13 | T10624C | EXON 2 | SER | SER | Neutral |

TABLE 4-continued

Amino Acid Polymorphisms

| SNP | POSITION | LOCATION | VARIANT 1 | VARIANT 2 | Effect on amino acid side chain |
|---|---|---|---|---|---|
| 14 | G10669A | EXON 2 | ARG | ARG | Neutral |
| 15 | T10873C | EXON 2 | TYR | TYR | Neutral |
| 16 | G11020A | EXON 2 | ALA | ALA | Neutral |
| 17 | A11117G | EXON 2 | SER | GLY | Hydrophilic - Hydrophobic |
| 18 | T11138G | EXON 2 | SER | ALA | Hydrophilic - Hydrophobic |
| 19 | G11142T | EXON 2 | GLY | VAL | Conservative |
| 20 | C11145T | EXON 2 | SER | LEU | Hydrophilic - Hydrophobic |
| 21 | G11233C | EXON 2 | SER | SER | Neutral |
| 22 | T11260C | EXON 2 | CYS | CYS | Neutral |
| 23 | G11495A | EXON 2 | ASP | ASN | Hydrophilic charged - Hydrophilic neutral |

TABLE 5

| Primer Name | Primer Sequence Forward | SEQ ID NO | Primer Sequence Reverse | SEQ ID NO |
|---|---|---|---|---|
| SEEK INI_8 | CAGTGAGCTGAGACCGTG | 115 | CTGGTACCAGTGTGTCAG | 116 |
| SEEK INI_8 | CAGTGAGCTGAGACCGTG | 115 | CTGGTACCAGTGTGTCAG | 116 |
| SEEK INI_8 | CAGTGAGCTGAGACCGTG | 115 | CTGGTACCAGTGTGTCAG | 116 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK INI_6 | GACTCCTCAGAGCCTCAG | 117 | GTAGCTACTGAAGCCGCTG | 118 |
| SEEK PROM3 | CCTAGATCAAGAGGCCCAG | 119 | ACAGCAGGAGACTCGAGG | 120 |
| SEEK PROM3 | CCTAGATCAAGAGGCCCAG | 119 | ACAGCAGGAGACTCGAGG | 120 |
| SEEK PROM3 | CCTAGATCAAGAGGCCCAG | 119 | ACAGCAGGAGACTCGAGG | 120 |
| SEEK PROM3 | CCTAGATCAAGAGGCCCAG | 119 | ACAGCAGGAGACTCGAGG | 120 |
| SEEK PROM3 | CCTAGATCAAGAGGCCCAG | 119 | ACAGCAGGAGACTCGAGG | 120 |
| SEEK PROM3 | CCTAGATCAAGAGGCCCAG | 119 | ACAGCAGGAGACTCGAGG | 120 |
| SEEK PROM3 | CCTAGATCAAGAGGCCCAG | 119 | ACAGCAGGAGACTCGAGG | 120 |
| SEEK PROM3 | CCTAGATCAAGAGGCCCAG | 119 | ACAGCAGGAGACTCGAGG | 120 |
| SEEK PROM3 | CCTAGATCAAGAGGCCCAG | 119 | ACAGCAGGAGACTCGAGG | 120 |
| SEEK PROM2 | CCTCAGATGCTTCATGAATGG | 121 | GTGAAGTCAGCCGAATAGC | 122 |
| SEEK PROM2 | CCTCAGATGCTTCATGAATGG | 121 | GTGAAGTCAGCCGAATAGC | 122 |
| SEEK PROM2 | CCTCAGATGCTTCATGAATGG | 121 | GTGAAGTCAGCCGAATAGC | 122 |
| SEEK PROM2 | CCTCAGATGCTTCATGAATGG | 121 | GTGAAGTCAGCCGAATAGC | 122 |
| SEEK PROM2 | CCTCAGATGCTTCATGAATGG | 121 | GTGAAGTCAGCCGAATAGC | 122 |
| SEEK PROM2 | CCTCAGATGCTTCATGAATGG | 121 | GTGAAGTCAGCCGAATAGC | 122 |

TABLE 6

| SNP | AC006163 nt position | Corneodesmosin nt position | Location in gene | Flanking Sequence | IUB Code | SEQ ID NO |
|---|---|---|---|---|---|---|
| 1 | 6,984 bp | −115 | 5UTR | TACCACGCTCCTCCGGCCACACCAACTTCCCC/TGGGGCACCCACCCCCTCCACCTCTCCTCTCCC | Y | 123 |
| 2 | 7,068 bp | −31 | 5UTR | TGCCCAGGGAATGTCCAGCTCTGGCATAAAGGACCCA/GGGTGTCCTGAGCTGCCATCAGTCAGGAGGCCG | R | 124 |
| 3 | 7,077 bp | −22 | 5UTR | AGCTCTGGCATAAAGGACCCAGGTGTCCTC/TGAGCTGCCATCAGGAGGCCGTGCAGCCCGAGATGGGC | Y | 125 |
| 4 | 7,107 bp | 9 | 5UTR | GAGCTGCCATCAGTCAGGAGGCCGTGCAGC/TCCGAGATGGGCTCGTCTCGGGCACCGTGATGGGCGT | Y | 126 |
| 5 | 7,164 bp | 66 | Exon 1 | GCACCCTGGATGGGGCTAGGGAAGGCAGAAGGGACGGATGA/TTGGCACTGCTGCTGGCTGGTCTTCCTCCTGCCAGG | W | 127 |
| 6 | 8,884 bp | Intron 1 | Intron 1 | CTGGAGGGAACGCAGGGTAAGCATGGAGGAACCAGG T/A GAAAGAGTCATGGAGGAACCATGGGTAAGTT | W | 128 |
| 7 | 8,906 bp | Intron 1 | Intron 1 | CAGAAGGAACGCAGGGTAAGCATGGAGGAACCAT/GGGGTAAGTTGGGCCTGGGGTTTGAAGCAA | Y | 129 |
| 8 | 8,931 bp | Intron 1 | Intron 1 | GGAGGAACCATGGGGTAAGTTGGGCCTGGGGTTTG/CAGCAAAGGAAAGGAAAGATAAGGAAAGATGTGGCTC | S | 130 |
| 9 | 9,558 bp | Intron 1 | Intron 1 | CTGTCTCTTCAGGGTCCTTTCTTTTAGACCTAT/CTTGTTCCTGCCCCTTCCAGGCTGGTCTTGAACTCTGGGGCG | Y | 131 |
| 10 | 9,607 bp | Intron 1 | Intron 1 | AAAAAATTTTAATTAAAAAACAAAATAACAGAT/CGGGGTCTATGTTGCCAGGCTGGTCTTGAACTCTGGGGCG | Y | 132 |
| 11 | 9,608 bp | Intron 1 | Intron 1 | AAAAAATTTTAATTAAAAAACAAAATAACAGATG/AGGGTCTATGTTGCCAGGCTGGTCTTGAACTCTGGGGGC | R | 133 |
| 12 | 9,647 bp | Intron 1 | Intron 1 | GGGTCTATGTTGCCAGGCTGGTCTTGAACTCTGGGGCG/ACATGCAATCCTCCCACCTCAGCCTCCCAAAGTGCTGG | R | 134 |
| 13 | 9,667 bp | Intron 1 | Intron 1 | TCTTGAACTCTGGGGCGCATGCAATCCTCCCACCTCA/GGCCTCCAAGTGCTGGGATTACGGCGTGAGCCACT | R | 135 |
| 14 | 9,745 bp | Intron 1 | Intron 1 | AGCCCCTCTATATTCAATGTATTCCTTTGAGGT/CCACTCACTTTGGCACGTAATTTTCTATTTTCTGGTTG | Y | 136 |
| 15 | 9,761 bp | Intron 1 | Intron 1 | TCAATGTATTCCTTTGAGGTCCACTCACTTTGGCACG/CTAATTTTCTATTTTCTGGTTGTTTGCCACCCTT | S | 137 |
| 16 | 9,926 bp | Intron 1 | Intron 1 | CCCTGCGCTCTGCTTGGGAGAAACCCAGAAGGCCGATT/GACTGAGATAAGGCAGAAAAGGTGAGGAGAAGCA | Y | 138 |
| 17 | 9,952 bp | Intron 1 | Intron 1 | AGAGGCCGATTACTGAGATAAGGCAGAAAAGGTGAGGG/AAGGAGCCAAGCTCTTTGGCCCTTACTAACCACTG | R | 139 |
| 18 | 9,968 bp | Intron 1 | Intron 1 | ACTGAGATAAGGCAGAAAAGGTGAGGAAGCCAAGCTCT/CTTGTAAGGACCCAGGTCTTTCCTCCACAGGGACCCTG | Y | 140 |
| 19 | 10,039 bp | 137 | Exon 2 | CAGGGACCTTGGCTAAGAGCATTGGCACTTCTCCAGACCC C/TTGTAAGGACCCGTATCACCTCCCCTAAGGACCCCT | Y | 141 |
| 20 | 10,082 bp | 180 | Exon 2 | GGACCCCACGCGTATCACCTCCCTAAGCGACCCCTGCC/TTCACTGGAAGGGTGACTCCAGCGGCT | Y | 142 |
| 21 | 10,108 bp | 206 | Exon 2 | ACGACCCCTGCCTCCCAGCTGGAAGGGTGACTCCAGTAGCTACAGCGGCT/TTTCAGTAGCTACAGTGGCTCCAGCAGTTCTGGCAGCTCCAT | Y | 143 |
| 22 | 10,344 bp | 442 | Exon 2 | CCGGTTCCTCCCAGCTGGGGAGCAGCAGCTCCACTCGGG(AAG/C)ACAGCGGCTCTCATTGAGGCAGCAGCAGCAGCTT | R | 144 |
| 23 | 10,363 bp (ins) | 461 | Exon 2 | GAGGCAGCAGCTCTCACTCGGGAAGCAGCAGCAGCAGCTTCAGTGCGGCTCTCATTCGAGCAGCAGCAGCAGCTT | Ins/del | 145 |
| 24 | 10,516 bp | 614 | Exon 2 | AATACTAAACCCTTCCCAGCCTGGACAAAAGCTCTTCCTCCCTCCCAA/GACCTYTGGGGGTATCCAGCAGTGCAAAGGTCAGCTC | R | 146 |
| 25 | 10,521 bp | 619 | Exon 2 | AATACTAAACCCTTCCCAGCCTGGACAAAAGCTCTTCCTCCCAAACCTC/TTGGGGTATCCAGCAGTGCAAAGGTCAGCTCC | Y | 147 |
| 26 | 10,624 bp | 722 | Exon 2 | CGACTCTCCCTGACTCCCAGTGAGGGCCATCGTCTTGCCACTCTGTGTCCAGGAGG/ACCTGTGTCAGGGTGGACCACGGTTCTGGTGC | Y | 148 |
| 27 | 10,669 bp | 767 | Exon 2 | CCTACATCCCAGCTCCCACTCTGTCCAGGAGGTCAGAG/ACCTGTGGGCTACTTCACCAAAGAGAACCCTGTGA | R | 149 |
| 28 | 10,873 bp | 971 | Exon 2 | ACAGTTATCTGGTTCCAGGCATGACTACAGTAAGGGTAAAATCTAT/CCTGTGGGCTACTTCACCAAAGAGAACCCTGTGA | Y | 150 |
| 29 | 11,020 bp | 1118 | Exon 2 | ACCCCATCATCCCCAGCCAGTCGGCAGCTTCCTCGGCCATTGCG/ATTTCCAGCCAGTGGGACTGGTGGGGTCCAGC | R | 151 |
| 30 | 11,117 bp | 1215 | Exon 2 | CCAAGGGACCCTGCTCTCCCCAGTTCTCGAGGTCCCCAGCA/GGTTCTAGCATTTCCAGCAGCTCCGGTTCACCCTG | R | 152 |
| 31 | 11,138 bp | 1236 | Exon 2 | CTCGAGTCCCACAGCACGTCCG G/T TTCACCTACCTACCATCCCTGCGCAGTGCT | K | 153 |
| 32 | 11,142 bp | 1240 | Exon 2 | CTAGCATTTCCAGCAGCTCCGGTTCACCCTACCTACCATCCCTGCGGCAGTGCTT | K | 154 |
| 33 | 11,145 bp | 1243 | Exon 2 | CCAGCAGTTCTAGCATTTCCAGCAGCTCCGGTTC/TACCCTACCATCCCTGCGGCAGTGCTTCCAGAG | Y | 155 |
| 34 | 11,233 bp | 1331 | Exon 2 | GGCACCGGGTCCTTCAGCAGCAGCTCCAGTTCCAATCG/CAGTGGCAAAATCATCCTTCAGCCTTGTTGGCAGCAA | S | 156 |
| 35 | 11,260 bp | 1358 | Exon 2 | AGTTCCAATCGAGTGGCAAAATCATCCTTCAGCCTTGT/CGGCAGCAAGAAGTCAACTGTTGTGTGTGCAT | Y | 157 |
| 36 | 11,495 bp | 1593 | Exon 2 | TGAAGTTTTCCACCCAAGGAGGTTACTG/AACAGCTCAT(AAG)AAGTCAACTGTTGTGTGTGCAT | R | 158 |
| 37 | 11,505 bp (ins) | 1603 | 3UTR | TACCCCAAGGAGAGTTACTGACAGTCCAT(AAG)AAGTCAACTGTTGTGTGCATGCCTTGGGCACAAA | Ins/del | 159 |
| 38 | 11,575 bp | 1674 | 3UTR | GGCACAAAACAAGCACATACACTATCCCAAAAGAGTGTTCCTGCTTTCT/CACTGCCCAGGCATAGGGTTAGCTCAGTTTCCCTCCTTCCCA | K | 160 |
| 39 | 11,641 bp | 1739 | 3UTR | AGCTCAGTTCCCTCCTTCCCACTGCTTTCT/CACTACCCCTCCTCCTCTC | Y | 161 |
| 40 | 11,649 bp | 1747 | 3UTR | AAAAGAGTGGTTCTGCTTTCTCGCTTCTACTACCCT/CAAGGTTGCCAGACTCTTCTTATCACCCCTCCTCCTCTC | Y | 162 |
| 41 | 11,808 bp | 1906 | 3UTR | AGATCACCACCCCTTACAAATTCCCTACTGTGTT/GGAAAATGGTCCATTGAGTAACACCCCATCACCTTCTCAACT | K | 163 |
| 42 | 11,839 bp | 1937 | 3UTR | GAAATGGTCCATTGAGTAACACCCCATCAC/GCTTCTCAACTGGGAAACCCTGAAATGCTCTCAGAGCACC | S | 164 |
| 43 | 11,885 bp | 1963 | 3UTR | TGAAATGCTCTCAGAGCACCTCTGA T/C GCCTGAAGAAGTTATACCTTCCTC | K | 165 |
| 44 | 11,977 bp | 2075 | 3UTR | AACCATCATCTGGAAACAGTGGCCACTTTTCACTGACCTC/TTCTTCGACATCCAGTCAACCACCCAACCCAATATGC | Y | 166 |

TABLE 6-continued

| SNP | AC006163 nt position | Corneodesmosin nt position | Location in gene | Flanking Sequence | IUB Code | SEQ ID NO |
|---|---|---|---|---|---|---|
| 45 | 12,018 bp | 2116 | 3UTR | ATCTAGTCAACCCACCCAATATGCCACTGGGCTT/CTCGCTCCAATTCCACCCCACCCTCCATTACAGAGCTCACCA | Y | 167 |
| 46 | 12,136 bp | 2234 | 3UTR | GCCTCTCAAGGCCCTTATCTCAGCCCTTCCTGTGGCCAT/CTTCCCTGAGTGCCCAGATGATTCCCTGGGTGAGGGCAGACAC | Y | 168 |
| 47 | 12,149 bp | 2247 | 3UTR | CAGCCCCTTCCTGTGGCCATTTCCCTCAGTGCC/TCAGATGATTCCCTGGGTGAGGGAGACACTGGGGCACCCTC | Y | 169 |
| 48 | 12,198 bp | 2296 | 3UTR | TTCCCTGGGGTGAGGGAGACACTGGGGCACCCTCAGAGGTTGG/AAGCAGGCTCCCTGCTGTCCCTGGATCCTGGACAGA | R | 170 |
| 49 | 12,283 bp | 2381 | 3UTR | GGTGCAGAGACTTTTTGCCTTCTTGGA G/A TCCTGGGTCTCCTCTGAGAGTCTG | R | 171 |
| 50 | 12,318 bp | 2416 | 3UTR | TCTTGGAGTCCTGCTCTTCCTACGCCTCTAGAGGTCTGGTGCT/CTCCTACGCCTCTGTGTC/TCCTCATTTCCTTCGTGTCTGTCCTCA | Y | 172 |
| 51 | 12,345 bp | 2443 | 3UTR | TGGGTGGTGCTCTTCCTACGCCTCTGTGTC/TCCTCATTTCCTTCAAAAGCGGGCTGTGTTTCT | Y | 173 |
| 52 | 12,373 bp | 2471 | 3UTR | TCATTTCCTTCAAAAGCGGGCTGT G/A TTTCTCTTCTACCTTCCAGCTCCT | R | 174 |
| 53 | 12,901 bp | 2999 | 3UTR | TAGATCAAGAGCCCAGCTGTGGCAGAACAGAGCTGCCA/GGTGGTCTCTCCATTCTTCACTCCCTGCTCTGTGGGT | R | 175 |
| 54 | 13,001 bp | 3099 | 3UTR | AACATGCTCTCAGGTGAGGGCTGAGAAGGCAGAGTGCCCCA/CGTGGGAAAAGGAGTGCTTCCACTGGAAGAAGAGA | M | 176 |
| 55 | 13,020 bp | 3118 | 3UTR | GCTGAGAAGGCAGAGTGCCCCAGTGGGAAAAGGAGTGCGT/CTCCACTGGAAGAGAGAAGTGGAGTGTGTGGTG | Y | 177 |
| 56 | 13,108 bp | 3206 | 3UTR | GACTTAAGTCCTGAGACAGGCAGGGAGGAGGCTGAGGCGGAC/GGAAGTTCCGCATCCCAAGGAGGGCAGAGTGGATT | S | 178 |
| 57 | 13,117 bp | 3215 | 3UTR | TGAGACAGGCAGGGAGGAGGCTGAGGCGGACGAAGTTCCC/TGCATCCCAAGGAGGGCAGAGTGGATTGTGCTTGTCC | Y | 179 |
| 58 | 13,178 bp | 3276 | 3UTR | GGATTGTGCTTGTCCCTGTAGGAGAGCCCCACCCC/TAGGCACCTCAGAGCCTCTGCTTGGCTGCAAAGG | Y | 180 |
| 59 | 13,224 bp | 3322 | 3UTR | CTCAGAGCCTCTGCTTGGCTGCAAAGGAATTCACCCC/TTACTGTAGCACTTAACCCCATTCCTCCTATCAGGGTGG | Y | 181 |
| 60 | 13,316 bp | 3414 | 3UTR | TGAATTTAGAAACTTGTTGAAACTCCAAGTCTGAAATCAGCAA/GAAAATGTATTACATTGACCAGAAAGGATTGAATCACCCT | R | 182 |
| 61 | 13,365 bp | 3463 | 3UTR | ACAATTGACCAGAAAGGGATTGAATCACCCTTGGTC/CAGCAGTCTGGCCCTGATCTGCAGCCAATGGCAGGAATGGAGGTC | R | 183 |
| 62 | 13,562 bp | 3660 | 3UTR | AGGGCCTCTGGGCTCCATCCACTGCCAGTTGTCTGGAGA/TGGAGCTCTTCACTCCTCCAGTGGTTAAGCCAGCA | W | 184 |
| 63 | 13,605 bp | 3703 | 3UTR | CTCTTCACTCCTCCAGTGGTTAAGCCAGCAGGGCAGGT/CGGGGAGGACAGCAGCAGTAGAATCAGCCAACAGCTCAT | Y | 185 |
| 64 | 13,670 bp | 3768 | 3UTR | CATGTTTAGACCTTGGGCAGCCAGGGAAGCC/TTACTCCTGGGGCCTCCCGGAAGCCATGGAGAGAAC | Y | 186 |
| 65 | 13,859 bp | 3857 | 3UTR | GATCAAGTCCTGGCCATTTGACAGCAGCATTTAAAGGCT/CCTCCTCTACTGTTACTTGGAAATAGCCACTTCTCCCAAGGT | Y | 187 |
| 66 | 13,889 bp | 3897 | 3UTR | CTCCTCTACTGTTACTTGGAAATAGCCACT/CTCTCCCAAGGTTTCTTATACTCT | Y | 188 |
| 67 | 13,914 bp | 3922 | 3UTR | GAAATAGCCACTTTCTCCCAAGGTTTCTTATATACTCTG/ATGGCACATCTGACCACCAGTAGCAGGCAGAATGATGT | R | 189 |

TABLE 7

| SNP | AC006163 nt position | nt position* | SNP | chemistry | Frequency allele 1 | allele 2 |
|---|---|---|---|---|---|---|
| 1 | 6,984 bp | 44884 | CDSN6984 | PSQ | 69.6 | 30.4 |
| 2 | 7,068 bp | 44968 | CDSN7068 | PSQ | 60.8 | 39.2 |
| 19 | 10,039 bp | 47939 | PS SEEK IN 1 6 C565T | Sequenced | 55 | 45 |
| 21 | 10,108 bp | 48008 | CDSN C10098T | Sequenced | not available | not available |
| 22 | 10,344 bp | 48244 | CDSN G10343A | Sequenced | not available | not available |
| 23 | 10,363 bp (ins) | 48262 | CDSN 10363 AAG ins | Sequenced | not available | not available |
| 24 | 10,516 bp | 48416 | CDSNx2.2A10516G | PSQ | 47.8 | 52.2 |
| 25 | 10,521 bp | 48421 | CDSNx2.2C10521T | PSQ | 20.5 | 79.5 |
| 26 | 10,624 bp | 48524 | CDSNx2T10614C | SNaPshot | 48.9 | 51.1 |
| 27 | 10,669 bp | 48569 | CDSNx2.2G10669A | SNaPshot | 85.7 | 14.3 |
| 28 | 10,873 bp | 48773 | CDSN T10873C | SNaPshot | 32.3 | 67.7 |
| 29 | 11,020 bp | 48920 | SEEKIN1_3 G27A | PSQ | 43.8 | 56.2 |
| 30 | 11,117 bp | 49017 | SEEKIN1_3 A124G | PSQ | 98.8 | 1.2 |
| 31 | 11,138 bp | 49038 | SEEKIN1_3 T145G | PSQ | 82.8 | 17.2 |
| 32 | 11,142 bp | 49042 | SEEKIN1_3 G149T | PSQ | 100 | 0 |
| 33 | 11,145 bp | 49045 | SEEKIN1_3 C152T | PSQ | 64.3 | 35.7 |
| 34 | 11,233 bp | 49133 | SEEKIN1_3 G241C | PSQ | 47.8 | 52.2 |
| 35 | 11,260 bp | 49160 | SEEKIN1_3 T268C | PSQ | 78.9 | 21.1 |
| 36 | 11,495 bp | 49395 | SEEK1in3 G503A | SNaPshot | 68.7 | 31.3 |
| 37 | 11,505 bp (ins) | 49404–49407 | SEEK1in3.511INS | SNaPshot | 43.4 | 56.6 |
| 38 | 11,575 bp | 49479 | CDSN G11576T | SNaPshot | 32.5 | 67.5 |

TABLE 8

| | SNP-1 | SNP-2 | SNP-19 | SNP-21 | SNP-22 | SNP-23 | SNP-24 | SNP-25 | SNP-26 | SNP-27 | SNP-28 |
|---|---|---|---|---|---|---|---|---|---|---|---|
| SNP1 | 1 | 0.76 | 0.89 | 0.75 | −0.88 | −0.19 | 0.55 | 0.23 | −0.56 | 0.13 | −0.47 |
| SNP2 | | 1 | 0.81 | 0.74 | −0.8 | −0.3 | 0.45 | 0.18 | −0.42 | 0.17 | −0.27 | −0.6 |
| SNP19 | | | 1 | 0.79 | −0.91 | −0.26 | 0.56 | 0.19 | −0.54 | 0.15 | −0.41 | −0.6 |
| SNP21 | | | | 1 | −0.84 | −0.3 | 0.43 | 0.16 | −0.39 | 0.07 | −0.35 | −0.48 |
| SNP22 | | | | | 1 | 0.26 | −0.56 | −0.18 | 0.52 | −0.13 | 0.41 | 0.55 |
| SNP23 | | | | | | 1 | 0.55 | 0.23 | −0.55 | 0.17 | −0.4 | −0.47 | −0.14 |
| SNP24 | | | | | | | 1 | 0.41 | −0.99 | 0.36 | −0.71 | −1 |
| SNP25 | | | | | | | | 1 | −0.43 | −0.27 | −0.59 | −0.33 |
| SNP26 | | | | | | | | | 1 | −0.33 | 0.71 | 1 |
| SNP27 | | | | | | | | | | 1 | 0.34 | −0.33 |
| SNP28 | | | | | | | | | | | 1 | 0.65 |
| SNP29 | | | | | | | | | | | | 1 |
| SNP30 | | | | | | | | | | | | |
| SNP36 | | | | | | | | | | | | |
| SNP37 | | | | | | | | | | | | |
| SNP38 | | | | | | | | | | | | |

| | SNP-29 | SNP-30 | SNP-31 | SNP-32 | SNP-33 | SNP-34 | SNP-35 | SNP-36 | SNP-37 | SNP-37 |
|---|---|---|---|---|---|---|---|---|---|---|
| SNP1 | −0.57 | −0.1 | 0.04 | n/a | 0.46 | −0.55 | 0 | −0.92 | 0.55 | 0.55 |
| SNP2 | 0.03 | 0.16 | n/a | 0.41 | −0.48 | 0.05 | −0.8 | 0.45 | 0.29 | 0.29 |
| SNP19 | −0.09 | 0.12 | n/a | 0.46 | −0.55 | 0.08 | −0.93 | 0.55 | 0.42 | 0.42 |
| SNP21 | −0.01 | 0.05 | n/a | 0.33 | −0.39 | 0.11 | −0.8 | 0.4 | 0.34 | 0.34 |
| SNP22 | 0.08 | −0.11 | n/a | −0.45 | 0.54 | −0.06 | 0.94 | −0.53 | −0.41 | −0.41 |
| SNP23 | 0.14 | n/a | 0.52 | −0.5 | −0.26 | 0.27 | 0.54 | 0.4 | 0.4 | |
| SNP24 | −0.16 | 0.3 | n/a | 0.86 | −0.96 | −0.28 | −0.56 | 1 | 0.71 | 0.71 |
| SNP25 | 0.02 | −0.29 | n/a | 0.36 | −0.34 | −0.25 | −0.2 | 0.43 | 0.58 | 0.58 |
| SNP26 | 0.15 | −0.28 | n/a | −0.86 | 0.94 | 0.22 | 0.55 | −0.98 | −0.71 | −0.71 |
| SNP27 | 0.08 | 0.93 | n/a | 0.27 | −0.31 | 0 | −0.16 | 0.33 | −0.36 | −0.36 |
| SNP28 | 0.18 | 0.35 | n/a | −0.64 | 0.67 | 0.25 | 0.44 | −0.71 | −0.97 | −0.97 |
| SNP29 | 0.02 | −0.14 | n/a | −0.67 | 1 | −0.34 | 0.61 | −1 | −0.72 | −0.72 |
| SNP30 | 1 | 0.1 | n/a | −0.15 | 0.13 | −0.02 | 0.11 | −0.13 | −0.18 | −0.18 |
| SNP31 | | 1 | n/a | 0.3 | −0.25 | −0.01 | −0.13 | 0.27 | −0.37 | −0.37 |
| SNP32 | | | n/a | n/a | n/a | n/a | n/a | n/a | n/a | n/a |
| SNP33 | | | | 1 | −0.82 | −0.25 | −0.48 | 0.86 | 0.64 | 0.64 |
| SNP34 | | | | | 1 | 0.18 | 0.58 | −0.95 | −0.68 | −0.68 |
| SNP35 | | | | | | 1 | −0.1 | −0.23 | −0.23 | −0.23 |
| SNP36 | | | | | | | 1 | −0.55 | −0.44 | −0.44 |
| SNP37 | | | | | | | | 1 | 0.72 | 0.72 |
| SNP38 | | | | | | | | | 1 | 1 |

TABLE 9

| SNP Number | Position | SNP Type | Frequency (allele 1) | Transmissions | chi-squared | p value (bootstrap) | Number of Transmissions Allele 1 observed | Allele 1 expected | Allele 2 observed | Allele 2 expected |
|---|---|---|---|---|---|---|---|---|---|---|
| 1 | 44884 | Promotor | 0.79 | 117 | 3.99 | 0.043 | 235 | 226 | 53 | 62 |
| 2 | 44968 | Promotor | 0.69 | 98 | 1.14 | 0.213 | 157 | 152 | 67 | 72 |
| 19 | 47939 | Silent | 0.79 | 133 | 11.43 | 0.002 | 260 | 244 | 50 | 66 |
| 21 | 48008 | leu-ser | 0.74 | 125 | 10.7 | 0 | 238 | 221 | 60 | 77 |
| 22 | 48244 | ser-asn | 0.2 | 132 | 3.44 | 0.061 | 55 | 64 | 259 | 250 |
| 23 | 48262 | ins/del (ser) | 0.82 | 112 | 9.28 | 0 | 231 | 219 | 33 | 45 |
| 24 | 48416 | Silent | 0.59 | 125 | 18.03 | 0 | 203 | 180 | 99 | 122 |
| 25 | 48421 | ser-phe | 0.18 | 120 | 1.43 | 0.18 | 44 | 49 | 232 | 227 |
| 26 | 48524 | silent | 0.43 | 140 | 22.93 | 0 | 113 | 143 | 229 | 199 |
| 27 | 48569 | silent | 0.13 | 139 | 5.97 | 0.025 | 35 | 45 | 305 | 295 |
| 28 | 48773 | silent | 0.56 | 142 | 36.51 | 0 | 152 | 188 | 194 | 158 |
| 29 | 48920 | silent | 0.47 | 26 | 0.99 | 0.283 | 23 | 26 | 33 | 31 |
| 30 | 49017 | ser-gly | 0.96 | 131 | 11.16 | 0 | 291 | 299 | 21 | 13 |
| 31 | 49038 | ser-ala | 0.13 | 135 | 4.55 | 0.051 | 34 | 42 | 290 | 282 |
| 32 | 49042 | gly-val | 1 | | | | | | | |
| 33 | 49045 | ser-leu | 0.59 | 132 | 9.69 | 0 | 211 | 193 | 111 | 129 |
| 34 | 49133 | ser-leu | 0.43 | 133 | 11 | 0.002 | 115 | 135 | 203 | 183 |
| 35 | 49160 | silent | 0.33 | 102 | 0.74 | 0.381 | 77 | 81 | 169 | 165 |
| 36 | 49395 | silent | 0.22 | 140 | 6.47 | 0.02 | 61 | 74 | 281 | 268 |
| 37 | 49404 | ins/del | 0.58 | 139 | 18.32 | 0 | 223 | 197 | 113 | 139 |
| 38 | 49479 | 3' UTR | 0.44 | 144 | 34.99 | 0 | 194 | 158 | 156 | 192 |

TABLE 10a

| SNP Number | Haplotype A | B | C |
|---|---|---|---|
| 1 | 1 | 1 | 2 |
| 2 | 1 | 1 | 2 |
| 19 | 1 | 1 | 2 |
| 21 | 1 | 1 | 2 |
| 22 | 2 | 2 | 1 |
| 23 | 1 | 1 | 1 |
| 24 | 1 | 1 | 2 |
| 25 | 1 | 2 | 2 |
| 26 | 2 | 2 | 1 |
| 27 | 2 | 2 | 2 |
| 28 | 2 | 2 | 1 |
| 30 | 1 | 1 | 1 |
| 31 | 2 | 2 | 2 |
| 33 | 1 | 1 | 2 |
| 34 | 2 | 2 | 1 |
| 35 | 2 | 2 | 1 |
| 36 | 2 | 2 | 1 |
| 37 | 1 | 1 | 2 |
| 38 | 1 | 1 | 2 |

TABLE 10b

| Key | Code 1 | 2 |
|---|---|---|
| A/T | A | T |
| A/G | A | G |
| A/C | A | C |
| C/G | G | C |
| G/T | G | T |
| C/T | C | T |

SEQUENCE LISTING

<160> NUMBER OF SEQ ID NOS: 189

<210> SEQ ID NO 1
<211> LENGTH: 7700
<212> TYPE: DNA
<213> ORGANISM: Homo sapiens

<400> SEQUENCE: 1
tggagggcag atggagagac aggccaagcc acggtaggca ggagagttaa ggagccaggc    60
agctgggtcc cgtggcaaga gtggccgccc cagagtgggt ggccgtgggg cagagcgcct   120
ggttccgggt taggcaatga ggagccgggg ccaggcctgt caggtggcag gatcgttaga   180

-continued

```
gccccgtggc catgggtacc ccacactgca gccactgctg ctgctgagta ggcagatgca    240
ccgggctgat taccacgctc ctcccggcca caccaacttc ccccggggca cccacccccT    300
ccacctctcc tcctctcccc acagtgactc ctgcccaggg aatgtccagc tctggcataa    360
aggacccagg tgtcctcgag ctgccatcag tcaggaggcc gtgcagcccg agatgggctc    420
gtctcgggca ccctggatgg ggcgtgtggg tgggcacggg atgatggcac tgctgctggc    480
tggtctcctc ctgccaggta ggaggctggg ggccctggga acaggaggga ggcgggaggg    540
agactccggg agaggaccca gcgaagggga cgggcagggg ctctggaatc tgccttttga    600
gtctgggggt tgctcctcac tgtatggtcg cctcaggtaa gtttcttaaa cttcctgagc    660
cccagtttct gaaattctga agtggggtta atgacaccta cctctagtct gtgtgtctca    720
aattaaataa tgtatgtgat atgtactttg gaaattctag aggtttatat aaatggtggt    780
ggtgattttt attatgggag cactacaaga taatgattgg acatttaata gtaataatat    840 cattttaga gccttttat atgctagact ctgttttaag cacatttgga ttatatatta    900
gaacttttat tttatttttt tttgtgagat ggagtcccac tctgtctcca aggctggagt    960
gcagtggcgt aatctcggct cactgcaact tccacctctc aggttcaagc gactctcatg   1020
cctcagcctc tagagtagct gggacaacag gtgcccatca ccacacctgg ctaattttct   1080 ttttttgta tttttagtag aaacagggtt ttaccatttt ggtcaagctg gtcttgaact   1140
cctgactcaa gtgatccgct cgcctcggcc tccaaggtg ctgggattac aggcatgagc   1200
caccacaccc ggcctatatt agcacttttg atcattacaa gaacggtatg aaaagagatt   1260
tgctatttcc actctacaga tgaggacact gaggctcgga gaggttagga aactagctca   1320
aaatcatgca ttagaaggca gcaaagccaa gatttcaacc ccaggccagg caaccccTgg   1380
acctgtgttg ttgaccaccg ggtacttata gcccttgagg aatttctgcg accttcccat   1440
ggtctagtgg gtggttggtg tctgagggaa tagcgaaaga gagaggcaat gcatggtgga   1500
ttcgtgcaga ggactgaagg gaattggcac agctggggtt cggcgtggag gtgcatgcag   1560
agaatttctt tctgaggaga gaacagggac atcacagaga tggcagtct ggttgttggt    1620 ggagggatca ggatgagtgg cagtaataat tcataatata taatgcttta cactttctaa   1680
aacatctggc cgcacatgat agcttgtgcc tgtaatccca acacttcagg aggccaaggc   1740
aggtgaatcg cctgaggtca ggagttcaag accagcctgg ccaagatggt gaaaccccct   1800
ctctactaaa aatacaaaaa attagctggg tgtggtggcg gcacctgtg gtcccagcta   1860 cttgggaggc tgaggcagga gaatcgcttg caccaaggag gcagaggtta cagtgagctg   1920
agaccgtgtt attgcacttt agcctgggca acaagaaact ccatctcaca aaaaaaaaa   1980 aaaaaaaaaa aagaagaaa aaacttccag gtggatgatc tcatttagtt ttcttcatag   2040
taatgctgtg ggaaggcagg gaaaatttgg cccctctgaa tgtataaact aaagctcaga   2100
gaggttcagt aacttgctag tatgtggctc tgtttgtaac acgtgggacc tggaggggct   2160
agggaaggca gaaggaacgc aggtgaaaga gtcatggagg aaccatgggg taagttgggc   2220
ctggggtttt gagcaaagga aggaaagat aaggaaagat gtggctccac atccctgagg   2280
gaagtcaagg cagcagaagt cagatgaggg gctggacaga ggcaggtgtg ctcagagagg   2340
gaagctgatt gtggccagga gcctcggagg ttcgtggggt ttcgtcctgg ttccctgggc   2400
tgggccagcg agagcagggc tggctcaggg tgcggtgtcc tgacacactg gtaccagcag   2460
gttctgaagc aacaggtagt gaccccacat cctggccccc acccagcttt actggcatgg   2520
```

-continued

```
ccagtgctga gataggaaat agggtttcca ttcctgaccc cagcctgggc tctcacgaag    2580
aagctggtga ccaaatctta gtcctcgagt gcccttcct ttatttcagc ccctctgccc     2640
ccagctttgt cttttccag tgtctccttc tatatgtgtc tccacttctc agccctccat    2700
tgttttgcct tttgtcttct tccctctggt cccactgtct ggcccaggat ttttcccta    2760 agaatttacg cctggactcc tcagagcctc agtttcccca attctctgtc tcttcagggt    2820
cctttctttt agacctattt gttcctgccc cttctccatt ccctcttctt tttaaaaaaa    2880
attttaatta aaaacaaaa tacagatggg gtctatgttg cccaggctgg tcttgaactc    2940
tggggcgcat gcaatcctcc cacctcagcc tcccaaagtg ctgggattac ggcgtgagc    3000 cactgtgccc agccccctct tatattcaat gtattccttt gaggtcactc actttggcac    3060
gtaattttct attttctgg ttggtgtttg cccacccttc ccaaacaaag aaatgccttt    3120
attcggccac ctcaatatcc tttagagaca atagccagtt cttcctcctt tctccatccc    3180
taaactctcc ctgcgctctg cttgggagaa acccgagagg ccgattactg agataaggca    3240
gaaaggtgag ggaggaagcc aagcctcctt ggcccttact aaccactgct ttcctccaca    3300
gggaccttgg ctaagagcat tggcaccttc tcagacccct gtaaggaccc cacgcgtatc    3360
acctccccta acgacccctg cctcactggg aagggtgact ccagcggctt cagtagctac    3420
agtggctcca gcagttctgg cagctccatt tccagtgcca gaagctctgg tggtggctcc    3480
agtggtagct ccagcggatc cagcattgcc caggtggtt ctgcaggatc ttttaagcca    3540 ggaacgggt attcccaggt cagctactcc tccggatctg gctctagtct acaaggtgca    3600
tccggttcct cccagctggg gagcagcagc tctcactcgg gaagcagcgg ctctcactcg    3660
ggaagcagca gctctcattc gagcagcagc agcagctttc agttcagcag cagcagcttc    3720
caagtaggga atggctctgc tctgccaacc aatgacaact cttaccgcgg aatactaaac    3780
ccttcccagc ctggacaaag ctcttcctct tcccaaaccct ctggggtatc cagcagtggc    3840
caaagcgtca gctccaacca gcgtccctgt agttcggaca tccccgactc tccctgcagt    3900
ggagggccca tcgtctcgca ctctggcccc tacatcccca gctcccactc tgtgtcaggg    3960
ggtcagaggc ctgtggtggt ggtggtggac cagcacggtt ctggtgcccc tggagtggtt    4020
caaggtcccc cctgtagcaa tggtggcctt ccaggcaagc cctgtccccc aatcacctct    4080
gtagacaaat cctatggtgg ctacgaggtg gtgggtggct cctctgacag ttatctggtt    4140
ccaggcatga cctacagtaa gggtaaaatc tatcctgtgg gctacttcac caaagagaac    4200
cctgtgaaag gctctccagg ggtccttcc tttgcagctg gccccccat ctctgagggc    4260 aaatacttct ccagcaaccc catcatcccc agccagtcgg cagcttcctc ggccattgcg    4320
ttccagccag tggggactgg tggggtccag ctctgtggag gcggtccac gggctccaag    4380 ggaccctgct ctccctccag ttctcgagtc cccagcagtt ctagcatttc agcagctcc    4440 ggttcaccct accatccctg cggcagtgct tcccagagcc cctgctcccc accaggcacc    4500
ggctccttca gcagcagctc cagttcccaa tcgagtggca aaatcatcct tcagccttgt    4560
ggcagcaagt ccagctcttc tggtcaccct tgcatgtctg tctcctcctt gacactgact    4620 gggggcccccg atggctctcc ccatcctgat ccctccgctg gtgccaagcc ctgtggctcc    4680
agcagtgctg gaaagatccc ctgccgctcc atccgggata ctagccca agtgaagcct    4740 ctgggccccc agctagctga ccctgaagtt ttcctacccc aaggagagtt actcgacagt    4800
ccataagtca actgttgtgt gtgtgcatgc cttgggcaca aacaagcaca tacactatat    4860
cccatatggg agaaggccag tgcccaggca tagggttagc tcagtttccc tccttcccaa    4920
```

```
aagagtggtt ctgctttctc tactacccta aggttgcaga ctctctctta tcaccccttc    4980
ctccttcctc ttctcaaaat ggtagattca aagctcctct cttgattctc tcctactgtt    5040
taaattccca ttccaccaca gtgccccctca gccagatcac cacccettac aattccctct    5100 actgtgttga atggtccat tgagtaacac ccccatcacc ttctcaactg ggaaacccct    5160
gaaatgctct cagagcacct ctgacgcctg aagaagttat accttcctct tccccttttac    5220 caaataaagc aaagtcaaac catcatctgg aaacagtggc cacttttcac tgacctctct    5280
tcgacatcta gtcaacccac ccaatatgcc actgggcttt cgctcccaat tccaccccac    5340
cctccattac agagctcacc acgccctcct agatcaccgt ccccaacaca cccattgcct    5400
ctcaaggccc ttatctcagc cccttcctgt ggccatttcc ctcagtgccc agatgattcc    5460
ctgggtgagg gagacactgg ggcaccctca gaggttggag caggctccct gctgtccctg    5520
gatcctggac agatggctca gtaaactgtg gggactaggt gcagactttt tgccttcttg    5580
gagtcctggg tctcctctga gagtctgggt ggtgctcttc ctacgcctct agaggtctct    5640
gtgtccctca ttttccttca aaagcgggct gtgtttctct tctaccttcc agctcctccc    5700
acagaggagg aagacaataa atatttgttg aactgaaagc agagattgcc tggcctccca    5760
gatccttccg ccatttccct cctctctcat tgctccagga aatccattct cttcccattc    5820
ctcattcacc gtggggtccc ccttcccctt atttagggcc ctcagtgttt tctctccctc    5880
ccctcccctc ccctcccccac ccaaactcct tttcttccac cattagcatt cctcaccttc    5940
tagatgccat cctctctggg agtcatgagt ctcgatttcc tgggtttctg ggacacctgg    6000
aagcttggga aggctgggac acaacaactc caaccagatt cctgtcagct gagtaggagg    6060
ccagttgggc gttgttcctg gagctggggg tggagagagt aaaggactga gaggatggga    6120
gcggggcagg gagtgcagcc aagcagggtg actcactggc ctagatcaag aggcccagcc    6180
tgtggcagaa cagagctgcc agtggtctct ccatcttcac actccctgct ctgctggggt    6240
ccagagtgag agtgtgagca acatggctct caggtgaggg ctgagaaggc agagtgcccc    6300
agtgggaaag aggagtcgct tccactggag aagagagaga aagtggagtg tgtggtgggg    6360
tccatgcgac ttaagtcctg agacaggcag ggagaggctg aggcggacga agttcccgca    6420
tcccaaggag ggcagagtgg attgtgcttg tccctgtagg agcccacccc ccacccccag    6480
gccacctctc agagcctctg cttggctgca aaggaattca cccctactgt agcacttaac    6540
ccattccctc ctatcagggt ggtgctgtct ggtcctgaat ttagaactgt tgaaactcca    6600
agtctggaat cagcaaaaat gtattacatt gaccagaaag ggattgaatc acccttggtc    6660
cagcatctgg cccctgatct gcagccaatg gcaggaatcg aggtcctcag atgcttcatg    6720
aatgggaatt gcagggagag aaggctctct gatgtggtgt ttcctcgagt ctcctgctgt    6780
gctccaaatt aaaagcttgt gtaaaactca tgcatgtcat ccaaaaaggc ctctgggctc    6840
catccactgc cagttctgga gaggagctct tcactcctcc agtggttaag ccagcagggg    6900
caggcgggga ggacacagca gtagaatcag ccaacagctc atgtttagac cttgggcagc    6960
cagggaagcc tactcctggg gcctcccgga agccatggag agaacaaagc cattgcattt    7020
ttataataaa atttgcaaac atatttaaaa gccaacaaac tgttaatgaa tctctacatt    7080
ctcatcgccc agcttcaaca aggatcccag cttcaacaag gatcaagtcc tggccatttg    7140
acagcagcat ttaaaggccc tcctctactg ttacttggaa atagccactt tctcccaagg    7200
tttcttatac tctatggcac atctgaccac cagtagcagg cagaatgatg tcttcaaccc    7260
```

-continued

```
caacaccatc aaagatgtcc acatcctaat ccctggaacg taggaattag gttacatggc    7320
aaagggaaat taaggttcca gatgggatta aggttgctat tcggctgact tcacagagat    7380
tatcatggat tattcaggtg gtccagtgt agtcaccagg tcccttaatg tggacatggg     7440
aggcagaaga ggaagtctga gtgatacagt gtaagaaatg gctgattttg gctttggaga   7500
tggaggaagg ggaccatgag ccaaagaaca caggatgcct ctggaaggtg aaaaagcagg   7560
gaaagggatt ttcccctgag gcccccagaa agaatcacag ccctgctgac acctttattt   7620
taatccactg agacctgttt tagacttctg atctccaaaa ctgtaaagta ataaatccat    7680
gttgttgtaa gccattcggt                                               7700
```

<210> SEQ ID NO 2
<211> LENGTH: 1590
<212> TYPE: DNA
<213> ORGANISM: Homo sapiens
<220> FEATURE:
<221> NAME/KEY: CDS
<222> LOCATION: (1)..(1590)
<223> OTHER INFORMATION:
<220> FEATURE:
<221> NAME/KEY: misc_feature
<222> LOCATION: (447)..(450)
<223> OTHER INFORMATION: Ser deletion

<400> SEQUENCE: 2

```
atg ggc tcg tct cgg gca ccc tgg atg ggg cgt gtg ggt ggg cac ggg         48
Met Gly Ser Ser Arg Ala Pro Trp Met Gly Arg Val Gly Gly His Gly
1               5                   10                  15 atg wtg gca ctg ctg ctg gct ggt ctc ctc ctg cca ggg acc ttg gct         96
Met Xaa Ala Leu Leu Leu Ala Gly Leu Leu Leu Pro Gly Thr Leu Ala
            20                  25                  30 aag agc att ggc acc ttc tca gac ccy tgt aag gac ccc acg cgt atc       144
Lys Ser Ile Gly Thr Phe Ser Asp Pro Cys Lys Asp Pro Thr Arg Ile
        35                  40                  45 acc tcc cct aac gac ccc tgc ytc act ggg aag ggt gac tcc agc ggy       192
Thr Ser Pro Asn Asp Pro Cys Xaa Thr Gly Lys Gly Asp Ser Ser Gly
    50                  55                  60 ttc agt agc tac agt ggc tcc agc agt tct ggc agc tcc att tcc agt       240
Phe Ser Ser Tyr Ser Gly Ser Ser Ser Ser Gly Ser Ser Ile Ser Ser
65                  70                  75                  80 gcc aga agc tct ggt ggt ggc tcc agt ggt agc tcc agc gga tcc agc       288
Ala Arg Ser Ser Gly Gly Gly Ser Ser Gly Ser Ser Ser Gly Ser Ser
                85                  90                  95 att gcc cag ggt ggt tct gca gga tct ttt aag cca gga acg ggg tat       336
Ile Ala Gln Gly Gly Ser Ala Gly Ser Phe Lys Pro Gly Thr Gly Tyr
            100                 105                 110 tcc cag gtc agc tac tcc tcc gga tct ggc tct agt cta caa ggt gca       384
Ser Gln Val Ser Tyr Ser Ser Gly Ser Gly Ser Ser Leu Gln Gly Ala
        115                 120                 125 tcc ggt tcc tcc cag ctg ggg agc agc agc tct cac tcg gga arc agc       432
Ser Gly Ser Ser Gln Leu Gly Ser Ser Ser Ser His Ser Gly Xaa Ser
    130                 135                 140 ggc tct cac tcg gga agc agc agc tct cat tcg agc agc agc agc agc       480
Gly Ser His Ser Gly Ser Ser Ser Ser His Ser Ser Ser Ser Ser Ser
145                 150                 155                 160 ttt cag ttc agc agc agc agc ttc caa gta ggg aat ggc tct gct ctg       528
Phe Gln Phe Ser Ser Ser Ser Phe Gln Val Gly Asn Gly Ser Ala Leu
                165                 170                 175 cca acc aat gac aac tct tac cgc gga ata cta aac cct tcc cag cct       576
Pro Thr Asn Asp Asn Ser Tyr Arg Gly Ile Leu Asn Pro Ser Gln Pro
            180                 185                 190
```

```
gga caa agc tct tcc tct tcc car acc tyt ggg gta tcc agc agt ggc      624
Gly Gln Ser Ser Ser Ser Ser Gln Thr Xaa Gly Val Ser Ser Ser Gly
            195                 200                 205 caa agc gtc agc tcc aac cag cgt ccc tgt agt tcg gac atc ccc gac      672
Gln Ser Val Ser Ser Asn Gln Arg Pro Cys Ser Ser Asp Ile Pro Asp
        210                 215                 220 tct ccc tgc agt gga ggg ccc atc gtc tcg cac tcy ggc ccc tac atc      720
Ser Pro Cys Ser Gly Gly Pro Ile Val Ser His Ser Gly Pro Tyr Ile
225                 230                 235                 240 ccc agc tcc cac tct gtg tca ggg ggt cag agr cct gtg gtg gtg gtg      768
Pro Ser Ser His Ser Val Ser Gly Gly Gln Arg Pro Val Val Val Val
            245                 250                 255 gtg gac cag cac ggt tct ggt gcc cct gga gtg gtt caa ggt ccc ccc      816
Val Asp Gln His Gly Ser Gly Ala Pro Gly Val Val Gln Gly Pro Pro
        260                 265                 270 tgt agc aat ggt ggc ctt cca ggc aag ccc tgt ccc cca atc acc tct      864
Cys Ser Asn Gly Gly Leu Pro Gly Lys Pro Cys Pro Pro Ile Thr Ser
                275                 280                 285 gta gac aaa tcc tat ggt ggc tac gag gtg gtg ggt ggc tcc tct gac      912
Val Asp Lys Ser Tyr Gly Gly Tyr Glu Val Val Gly Gly Ser Ser Asp
290                 295                 300 agt tat ctg gtt cca ggc atg acc tac agt aag ggt aaa atc tay cct      960
Ser Tyr Leu Val Pro Gly Met Thr Tyr Ser Lys Gly Lys Ile Tyr Pro
305                 310                 315                 320 gtg ggc tac ttc acc aaa gag aac cct gtg aaa ggc tct cca ggg gtc     1008
Val Gly Tyr Phe Thr Lys Glu Asn Pro Val Lys Gly Ser Pro Gly Val
                325                 330                 335 cct tcc ttt gca gct ggg ccc ccc atc tct gag ggc aaa tac ttc tcc     1056
Pro Ser Phe Ala Ala Gly Pro Pro Ile Ser Glu Gly Lys Tyr Phe Ser
            340                 345                 350 agc aac ccc atc atc ccc agc cag tcg gca gct tcc tcg gcc att gcr     1104
Ser Asn Pro Ile Ile Pro Ser Gln Ser Ala Ala Ser Ser Ala Ile Ala
        355                 360                 365 ttc cag cca gtg ggg act ggt ggg gtc cag ctc tgt gga ggc ggc tcc     1152
Phe Gln Pro Val Gly Thr Gly Gly Val Gln Leu Cys Gly Gly Gly Ser
    370                 375                 380 acg ggc tcc aag gga ccc tgc tct ccc tcc agt tct cga gtc ccc agc     1200
Thr Gly Ser Lys Gly Pro Cys Ser Pro Ser Ser Ser Arg Val Pro Ser
385                 390                 395                 400 rgt tct agc att tcc agc agc kcc gkt tya ccc tac cat ccc tgc ggc     1248
Xaa Ser Ser Ile Ser Ser Ser Xaa Xaa Xaa Pro Tyr His Pro Cys Gly
                405                 410                 415 agt gct tcc cag agc ccc tgc tcc cca cca ggc acc ggc tcc ttc agc     1296
Ser Ala Ser Gln Ser Pro Cys Ser Pro Pro Gly Thr Gly Ser Phe Ser
            420                 425                 430 agc agc tcc agt tcc caa tcs agt ggc aaa atc atc ctt cag cct tgy     1344
Ser Ser Ser Ser Ser Gln Ser Ser Gly Lys Ile Ile Leu Gln Pro Cys
        435                 440                 445 ggc agc aag tcc agc tct tct ggt cac cct tgc atg tct gtc tcc tcc     1392
Gly Ser Lys Ser Ser Ser Ser Gly His Pro Cys Met Ser Val Ser Ser
    450                 455                 460 ttg aca ctg act ggg ggc ccc gat ggc tct ccc cat cct gat ccc tcc     1440
Leu Thr Leu Thr Gly Gly Pro Asp Gly Ser Pro His Pro Asp Pro Ser
465                 470                 475                 480 gct ggt gcc aag ccc tgt ggc tcc agc agt gct gga aag atc ccc tgc     1488
Ala Gly Ala Lys Pro Cys Gly Ser Ser Ser Ala Gly Lys Ile Pro Cys
                485                 490                 495 cgc tcc atc cgg gat atc cta gcc caa gtg aag cct ctg ggg ccc cag    1536
Arg Ser Ile Arg Asp Ile Leu Ala Gln Val Lys Pro Leu Gly Pro Gln
```

-continued

```
                           500              505              510
cta gct gac cct gaa gtt ttc cta ccc caa gga gag tta ctc rac agt       1584
Leu Ala Asp Pro Glu Val Phe Leu Pro Gln Gly Glu Leu Leu Xaa Ser
        515              520              525 cca taa                                                               1590
Pro
```

<210> SEQ ID NO 3
<211> LENGTH: 529
<212> TYPE: PRT
<213> ORGANISM: Homo sapiens
<220> FEATURE:
<221> NAME/KEY: SITE
<222> LOCATION: (18)..(18)
<223> OTHER INFORMATION: The 'Xaa' at location 18 stands for Met, or
      Leu.
<220> FEATURE:
<221> NAME/KEY: SITE
<222> LOCATION: (56)..(56)
<223> OTHER INFORMATION: The 'Xaa' at location 56 stands for Leu, or
      Phe.
<220> FEATURE:
<221> NAME/KEY: SITE
<222> LOCATION: (143)..(143)
<223> OTHER INFORMATION: The 'Xaa' at location 143 stands for Ser, or
      Asn.
<220> FEATURE:
<221> NAME/KEY: SITE
<222> LOCATION: (202)..(202)
<223> OTHER INFORMATION: The 'Xaa' at location 202 stands for Ser, or
      Phe.
<220> FEATURE:
<221> NAME/KEY: SITE
<222> LOCATION: (401)..(401)
<223> OTHER INFORMATION: The 'Xaa' at location 401 stands for Gly, or
      Ser.
<220> FEATURE:
<221> NAME/KEY: SITE
<222> LOCATION: (408)..(408)
<223> OTHER INFORMATION: The 'Xaa' at location 408 stands for Ala, or
      Ser.
<220> FEATURE:
<221> NAME/KEY: SITE
<222> LOCATION: (409)..(409)
<223> OTHER INFORMATION: The 'Xaa' at location 409 stands for Gly, or
      Val.
<220> FEATURE:
<221> NAME/KEY: SITE
<222> LOCATION: (410)..(410)
<223> OTHER INFORMATION: The 'Xaa' at location 410 stands for Ser, or
      Leu.
<220> FEATURE:
<221> NAME/KEY: SITE
<222> LOCATION: (527)..(527)
<223> OTHER INFORMATION: The 'Xaa' at location 527 stands for Asp, or
      Asn.

<400> SEQUENCE: 3

```
Met Gly Ser Ser Arg Ala Pro Trp Met Gly Arg Val Gly Gly His Gly
1               5                   10                  15

Met Xaa Ala Leu Leu Leu Ala Gly Leu Leu Pro Gly Thr Leu Ala
            20                  25                  30

Lys Ser Ile Gly Thr Phe Ser Asp Pro Cys Lys Asp Pro Thr Arg Ile
        35                  40                  45

Thr Ser Pro Asn Asp Pro Cys Xaa Thr Gly Lys Gly Asp Ser Ser Gly
    50                  55                  60

Phe Ser Ser Tyr Ser Gly Ser Ser Ser Gly Ser Ser Ile Ser Ser
65                  70                  75                  80

Ala Arg Ser Ser Gly Gly Gly Ser Gly Ser Ser Ser Gly Ser Ser
                85                  90                  95
```

```
Ile Ala Gln Gly Gly Ser Ala Gly Ser Phe Lys Pro Gly Thr Gly Tyr
            100                 105                 110
Ser Gln Val Ser Tyr Ser Ser Gly Ser Gly Ser Ser Leu Gln Gly Ala
            115                 120                 125
Ser Gly Ser Ser Gln Leu Gly Ser Ser Ser His Ser Gly Xaa Ser
            130                 135                 140
Gly Ser His Ser Gly Ser Ser Ser His Ser Ser Ser Ser Ser
145                 150                 155                 160
Phe Gln Phe Ser Ser Ser Phe Gln Val Gly Asn Gly Ser Ala Leu
                165                 170                 175
Pro Thr Asn Asp Asn Ser Tyr Arg Gly Ile Leu Asn Pro Ser Gln Pro
            180                 185                 190
Gly Gln Ser Ser Ser Ser Gln Thr Xaa Gly Val Ser Ser Ser Gly
            195                 200                 205
Gln Ser Val Ser Ser Asn Gln Arg Pro Cys Ser Ser Asp Ile Pro Asp
210                 215                 220
Ser Pro Cys Ser Gly Gly Pro Ile Val Ser His Ser Gly Pro Tyr Ile
225                 230                 235                 240
Pro Ser Ser His Ser Val Ser Gly Gly Gln Arg Pro Val Val Val
            245                 250                 255
Val Asp Gln His Gly Ser Gly Ala Pro Gly Val Val Gln Gly Pro Pro
            260                 265                 270
Cys Ser Asn Gly Gly Leu Pro Gly Lys Pro Cys Pro Ile Thr Ser
            275                 280                 285
Val Asp Lys Ser Tyr Gly Gly Tyr Glu Val Val Gly Gly Ser Ser Asp
            290                 295                 300
Ser Tyr Leu Val Pro Gly Met Thr Tyr Ser Lys Gly Lys Ile Tyr Pro
305                 310                 315                 320
Val Gly Tyr Phe Thr Lys Glu Asn Pro Val Lys Gly Ser Pro Gly Val
                325                 330                 335
Pro Ser Phe Ala Ala Gly Pro Pro Ile Ser Glu Gly Lys Tyr Phe Ser
            340                 345                 350
Ser Asn Pro Ile Ile Pro Ser Gln Ser Ala Ala Ser Ser Ala Ile Ala
            355                 360                 365
Phe Gln Pro Val Gly Thr Gly Gly Val Gln Leu Cys Gly Gly Gly Ser
            370                 375                 380
Thr Gly Ser Lys Gly Pro Cys Ser Pro Ser Ser Ser Arg Val Pro Ser
385                 390                 395                 400
Xaa Ser Ser Ile Ser Ser Ser Xaa Xaa Xaa Pro Tyr His Pro Cys Gly
                405                 410                 415
Ser Ala Ser Gln Ser Pro Cys Ser Pro Pro Gly Thr Gly Ser Phe Ser
            420                 425                 430
Ser Ser Ser Ser Gln Ser Ser Gly Lys Ile Ile Leu Gln Pro Cys
            435                 440                 445
Gly Ser Lys Ser Ser Ser Ser Gly His Pro Cys Met Ser Val Ser Ser
            450                 455                 460
Leu Thr Leu Thr Gly Gly Pro Asp Gly Ser Pro His Pro Asp Pro Ser
465                 470                 475                 480
Ala Gly Ala Lys Pro Cys Gly Ser Ser Ala Gly Lys Ile Pro Cys
            485                 490                 495
Arg Ser Ile Arg Asp Ile Leu Ala Gln Val Lys Pro Leu Gly Pro Gln
            500                 505                 510
```

Leu Ala Asp Pro Glu Val Phe Leu Pro Gln Gly Glu Leu Leu Xaa Ser
            515                 520                 525
Pro

<210> SEQ ID NO 4
<211> LENGTH: 1590
<212> TYPE: DNA
<213> ORGANISM: Homo sapiens

<400> SEQUENCE: 4

| | | | | | |
|---|---|---|---|---|---|
| ttatggactg | tcgagtaact | ctccttgggg | taggaaaact | tcagggtcag | ctagctgggg | 60 |
| ccccagaggc | ttcacttggg | ctaggatatc | ccggatggag | cggcagggga | tctttccagc | 120 |
| actgctggag | ccacagggct | tggcaccagc | ggagggatca | ggatggggag | agccatcggg | 180 |
| gcccccagtc | agtgtcaagg | aggagacaga | catgcaaggg | tgaccagaag | agctggactt | 240 |
| gctgccacaa | ggctgaagga | tgattttgcc | actcgattgg | gaactggagc | tgctgctgaa | 300 |
| ggagccggtg | cctggtgggg | agcaggggct | ctggaagca | ctgccgcagg | gatggtaggg | 360 |
| tgaaccggcg | ctgctggaaa | tgctagaact | gctggggact | cgagaactgg | agggagagca | 420 |
| gggtcccttg | gagcccgtgg | agccgcctcc | acagagctgg | accccaccag | tccccactgg | 480 |
| ctggaacgca | atggccgagg | aagctgccga | ctggctgggg | atgatgggt | tgctggagaa | 540 |
| gtatttgccc | tcagagatgg | ggggcccagc | tgcaaaggaa | gggaccctg | gagagccttt | 600 |
| cacaggttc | tctttggtga | agtagcccac | aggatagatt | ttaccttac | tgtaggtcat | 660 |
| gcctggaacc | agataactgt | cagaggagcc | acccaccacc | tcgtagccac | cataggatt | 720 |
| gtctacagag | gtgattgggg | gacagggctt | gcctggaagg | ccaccattgc | tacaggggg | 780 |
| accttgaacc | actccagggg | caccagaacc | gtgctggtcc | accaccacca | ccacaggcct | 840 |
| ctgaccccct | gacacagagt | gggagctggg | gatgtagggg | ccagagtgcg | agacgatggg | 900 |
| ccctccactg | cagggagagt | cggggatgtc | cgaactacag | ggacgctggt | tggagctgac | 960 |
| gcttggcca | ctgctggata | ccccagaggt | ttgggaagag | aagagctttt | gtccaggctg | 1020 |
| ggaagggttt | agtattccgc | ggtaagagtt | gtcattggtt | ggcagagcag | agccattccc | 1080 |
| tacttggaag | ctgctgctgc | tgaactgaaa | gctgctgctg | ctgctcgaat | gagagctgct | 1140 |
| gcttcccgag | tgagagccgc | tgcttcccga | gtgagagctg | ctgctcccca | gctgggagga | 1200 |
| accggatgca | ccttgtagac | tagagccaga | tccggaggag | tagctgacct | gggaataccc | 1260 |
| cgttcctggc | ttaaaagatc | ctgcagaacc | accctgggca | atgctggatc | cgctggagct | 1320 |
| accactggag | ccaccaccag | agcttctggc | actggaaatg | gagctgccag | aactgctgga | 1380 |
| gccactgtag | ctactgaagc | cgctggagtc | acccttccca | gtgaggcagg | ggtcgttagg | 1440 |
| ggaggtgata | cgcgtggggt | ccttacaggg | gtctgagaag | gtgccaatgc | tcttagccaa | 1500 |
| ggtccctggc | aggaggagac | cagccagcag | cagtgccatc | atcccgtgcc | acccacacg | 1560 |
| ccccatccag | ggtgcccgag | acgagcccat | | | | 1590 |

<210> SEQ ID NO 5
<211> LENGTH: 18
<212> TYPE: DNA
<213> ORGANISM: Artificial sequence
<220> FEATURE:
<223> OTHER INFORMATION: Primer

<400> SEQUENCE: 5
ctgggtcccg tggcaaga      18

<210> SEQ ID NO 6
<211> LENGTH: 18
<212> TYPE: DNA
<213> ORGANISM: Artificial sequence
<220> FEATURE:
<223> OTHER INFORMATION: Primer

<400> SEQUENCE: 6
gtcctctccc ggagtctc                                                 18

<210> SEQ ID NO 7
<211> LENGTH: 19
<212> TYPE: DNA
<213> ORGANISM: Artificial sequence
<220> FEATURE:
<223> OTHER INFORMATION: Primer

<400> SEQUENCE: 7
ggtgagggag gaagccaag                                                19

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
gagctgacgc tttggccac                                                19

<210> SEQ ID NO 9
<211> LENGTH: 23
<212> TYPE: DNA
<213> ORGANISM: Artificial sequence
<220> FEATURE:
<223> OTHER INFORMATION: Primer

<400> SEQUENCE: 9
gccaaccaat gacaactctt acc                                           23

<210> SEQ ID NO 10
<211> LENGTH: 18
<212> TYPE: DNA
<213> ORGANISM: Artificial sequence
<220> FEATURE:
<223> OTHER INFORMATION: Primer

<400> SEQUENCE: 10
gcctccacag agctggac                                                 18

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
ggcaaatact tctccagcaa cc                                            22

<210> SEQ ID NO 12
<211> LENGTH: 19
<212> TYPE: DNA
<213> ORGANISM: Artificial sequence
<220> FEATURE:
<223> OTHER INFORMATION: Primer -continued

```
<400> SEQUENCE: 12
ggccttctcc catatggga                                                    19

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
ccaaggagag ttactcgaca g                                                 21

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
ggcatattgg gtgggttgac                                                   20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
catctggaaa cagtggccac                                                   20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
gtcttcctcc tctgtgggag                                                   20

<210> SEQ ID NO 17
<211> LENGTH: 50
<212> TYPE: DNA
<213> ORGANISM: Homo sapiens

<400> SEQUENCE: 17
ctcccggcca caccaacttc ccccygggca cccacccct ccacctctcc                   50

<210> SEQ ID NO 18
<211> LENGTH: 50
<212> TYPE: DNA
<213> ORGANISM: Homo sapiens

<400> SEQUENCE: 18
aatgtccagc tctggcataa aggacccrgg tgtcctcgag ctgccatcag                  50

<210> SEQ ID NO 19
<211> LENGTH: 50
<212> TYPE: DNA
<213> ORGANISM: Homo sapiens
```

-continued

```
<400> SEQUENCE: 19
tctggcataa aggacccagg tgtcctygag ctgccatcag tcaggaggcc                50

<210> SEQ ID NO 20
<211> LENGTH: 50
<212> TYPE: DNA
<213> ORGANISM: Homo sapiens

<400> SEQUENCE: 20
ctgccatcag tcaggaggcc gtgcagyccg agatgggctc gtctcgggca                50

<210> SEQ ID NO 21
<211> LENGTH: 50
<212> TYPE: DNA
<213> ORGANISM: Homo sapiens

<400> SEQUENCE: 21
ggcgtgtggg tgggcacggg atgwtggcac tgctgctggc tggtctcctc                50

<210> SEQ ID NO 22
<211> LENGTH: 50
<212> TYPE: DNA
<213> ORGANISM: Homo sapiens

<400> SEQUENCE: 22
ctaagagcat tggcaccttc tcagacccyt gtaaggaccc cacgcgtatc                50

<210> SEQ ID NO 23
<211> LENGTH: 37
<212> TYPE: DNA
<213> ORGANISM: Homo sapiens

<400> SEQUENCE: 23 acctcccta acgacccctg cytcactggg aagggtg                               37

<210> SEQ ID NO 24
<211> LENGTH: 50
<212> TYPE: DNA
<213> ORGANISM: Homo sapiens

<400> SEQUENCE: 24
cagtagctac agtggctcca gcayttctgg cagctccatt tccagtgcca                50

<210> SEQ ID NO 25
<211> LENGTH: 50
<212> TYPE: DNA
<213> ORGANISM: Homo sapiens

<400> SEQUENCE: 25
gagcagcagc tctcactcgg gaarcagcgg ctctcactcg ggaagcagca                50

<210> SEQ ID NO 26
<211> LENGTH: 50
<212> TYPE: DNA
<213> ORGANISM: Homo sapiens

<400> SEQUENCE: 26
gaagcagcgg ctctcactcg ggaagcagca gctctcattc gagcagcagc                50

<210> SEQ ID NO 27
<211> LENGTH: 50
<212> TYPE: DNA
```

<400> SEQUENCE: 27
ctggacaaag ctcttcctct tcccaracct ctggggtatc cagcagtggc         50

<210> SEQ ID NO 28
<211> LENGTH: 50
<212> TYPE: DNA
<213> ORGANISM: Homo sapiens

<400> SEQUENCE: 28
ctggacaaag ctcttcctct tcccaaacct ytggggtatc cagcagtggc         50

<210> SEQ ID NO 29
<211> LENGTH: 50
<212> TYPE: DNA
<213> ORGANISM: Homo sapiens

<400> SEQUENCE: 29
ggagggccca tcgtctcgca ctcyggcccc tacatcccca gctcccactc         50

<210> SEQ ID NO 30
<211> LENGTH: 50
<212> TYPE: DNA
<213> ORGANISM: Homo sapiens

<400> SEQUENCE: 30
gctcccactc tgtgtcaggg ggtcagagrc ctgtggtggt ggtggtggac         50

<210> SEQ ID NO 31
<211> LENGTH: 50
<212> TYPE: DNA
<213> ORGANISM: Homo sapiens

<400> SEQUENCE: 31
cctacagtaa gggtaaaatc taycctgtgg gctacttcac caaagagaac         50

<210> SEQ ID NO 32
<211> LENGTH: 50
<212> TYPE: DNA
<213> ORGANISM: Homo sapiens

<400> SEQUENCE: 32
agccagtcgg cagcttcctc ggccattgcr ttccagccag tggggactgg         50

<210> SEQ ID NO 33
<211> LENGTH: 50
<212> TYPE: DNA
<213> ORGANISM: Homo sapiens

<400> SEQUENCE: 33
ctccctccag ttctcgagtc cccagcrgtt ctagcatttc cagcagctcc         50

<210> SEQ ID NO 34
<211> LENGTH: 50
<212> TYPE: DNA
<213> ORGANISM: Homo sapiens

<400> SEQUENCE: 34
cccagcagtt ctagcatttc cagcagckcc ggttcaccct accatccctg         50

<210> SEQ ID NO 35
<211> LENGTH: 50
<212> TYPE: DNA

<213> ORGANISM: Homo sapiens

<400> SEQUENCE: 35
ctagcatttc cagcagctcc gkttcaccct accatccctg cggcagtgct    50

<210> SEQ ID NO 36
<211> LENGTH: 50
<212> TYPE: DNA
<213> ORGANISM: Homo sapiens

<400> SEQUENCE: 36
ctagcatttc cagcagctcc ggttyaccct accatccctg cggcagtgct    50

<210> SEQ ID NO 37
<211> LENGTH: 50
<212> TYPE: DNA
<213> ORGANISM: Homo sapiens

<400> SEQUENCE: 37
gcagcagctc cagttcccaa tcsagtggca aaatcatcct tcagccttgt    50

<210> SEQ ID NO 38
<211> LENGTH: 50
<212> TYPE: DNA
<213> ORGANISM: Homo sapiens

<400> SEQUENCE: 38
tcgagtggca aaatcatcct tcagccttgy ggcagcaagt ccagctcttc    50

<210> SEQ ID NO 39
<211> LENGTH: 50
<212> TYPE: DNA
<213> ORGANISM: Homo sapiens

<400> SEQUENCE: 39
ttcctacccc aaggagagtt actcracagt ccataagtca actgttgtgt    50

<210> SEQ ID NO 40
<211> LENGTH: 50
<212> TYPE: DNA
<213> ORGANISM: Homo sapiens

<400> SEQUENCE: 40
gagagttact cgacagtcca taagaagtca actgttgtgt gtgtgcatgc    50

<210> SEQ ID NO 41
<211> LENGTH: 50
<212> TYPE: DNA
<213> ORGANISM: Homo sapiens

<400> SEQUENCE: 41
tacactatat cccatatggg agaagkccag tgcccaggca tagggttagc    50

<210> SEQ ID NO 42
<211> LENGTH: 50
<212> TYPE: DNA
<213> ORGANISM: Homo sapiens

<400> SEQUENCE: 42
cccaaaagag tggttctgct ttctcyacta ccctaaggtt gcagactctc    50

<210> SEQ ID NO 43
<211> LENGTH: 50

-continued

```
<212> TYPE: DNA
<213> ORGANISM: Homo sapiens

<400> SEQUENCE: 43
agtggttctg ctttctctac tacccyaagg ttgcagactc tctcttatca           50

<210> SEQ ID NO 44
<211> LENGTH: 50
<212> TYPE: DNA
<213> ORGANISM: Homo sapiens

<400> SEQUENCE: 44 cccccttacaa ttccctctac tgtgtkgaaa tggtccattg agtaacaccc          50

<210> SEQ ID NO 45
<211> LENGTH: 50
<212> TYPE: DNA
<213> ORGANISM: Homo sapiens

<400> SEQUENCE: 45
ggtccattga gtaacacccc catcascttc tcaactggga aacccctgaa           50

<210> SEQ ID NO 46
<211> LENGTH: 50
<212> TYPE: DNA
<213> ORGANISM: Homo sapiens

<400> SEQUENCE: 46
tgaaatgctc tcagagcacc tctgaygcct gaagaagtta taccttcctc           50

<210> SEQ ID NO 47
<211> LENGTH: 50
<212> TYPE: DNA
<213> ORGANISM: Homo sapiens

<400> SEQUENCE: 47
aaacagtggc cacttttcac tgacctytct tcgacatcta gtcaacccac           50

<210> SEQ ID NO 48
<211> LENGTH: 50
<212> TYPE: DNA
<213> ORGANISM: Homo sapiens

<400> SEQUENCE: 48
caacccaccc aatatgccac tgggcyttcg ctcccaattc caccccaccc           50

<210> SEQ ID NO 49
<211> LENGTH: 50
<212> TYPE: DNA
<213> ORGANISM: Homo sapiens

<400> SEQUENCE: 49
ttatctcagc cccttcctgt ggccayttcc ctcagtgccc agatgattcc           50

<210> SEQ ID NO 50
<211> LENGTH: 50
<212> TYPE: DNA
<213> ORGANISM: Homo sapiens

<400> SEQUENCE: 50
ttcctgtggc catttccctc agtgcycaga tgattccctg ggtgagggag           50

<210> SEQ ID NO 51
```

```
<211> LENGTH: 50
<212> TYPE: DNA
<213> ORGANISM: Homo sapiens

<400> SEQUENCE: 51
gacactgggg caccctcaga ggttgragca ggctccctgc tgtccctgga          50

<210> SEQ ID NO 52
<211> LENGTH: 50
<212> TYPE: DNA
<213> ORGANISM: Homo sapiens

<400> SEQUENCE: 52
ggtgcagact ttttgccttc ttggartcct gggtctcctc tgagagtctg          50

<210> SEQ ID NO 53
<211> LENGTH: 50
<212> TYPE: DNA
<213> ORGANISM: Homo sapiens

<400> SEQUENCE: 53
tcctctgaga gtctgggtgg tgctcytcct acgcctctag aggtctctgt          50

<210> SEQ ID NO 54
<211> LENGTH: 50
<212> TYPE: DNA
<213> ORGANISM: Homo sapiens

<400> SEQUENCE: 54
cctacgcctc tagaggtctc tgtgtycctc attttccttc aaaagcgggc          50

<210> SEQ ID NO 55
<211> LENGTH: 50
<212> TYPE: DNA
<213> ORGANISM: Homo sapiens

<400> SEQUENCE: 55
tcattttcct tcaaaagcgg gctgtrtttc tcttctacct tccagctcct          50

<210> SEQ ID NO 56
<211> LENGTH: 18
<212> TYPE: DNA
<213> ORGANISM: Artificial sequence
<220> FEATURE:
<223> OTHER INFORMATION: Primer

<400> SEQUENCE: 56
ctgggtcccg tggcaaga                                             18

<210> SEQ ID NO 57
<211> LENGTH: 18
<212> TYPE: DNA
<213> ORGANISM: Artificial sequence
<220> FEATURE:
<223> OTHER INFORMATION: Primer

<400> SEQUENCE: 57
gtcctctccc ggagtctc                                             18

<210> SEQ ID NO 58
<211> LENGTH: 26
<212> TYPE: DNA
<213> ORGANISM: Artificial sequence
<220> FEATURE:
<223> OTHER INFORMATION: Primer
```

```
<400> SEQUENCE: 58
ctgactgatg gcagctcgag gacagc                                    26

<210> SEQ ID NO 59
<211> LENGTH: 18
<212> TYPE: DNA
<213> ORGANISM: Artificial sequence
<220> FEATURE:
<223> OTHER INFORMATION: Primer

<400> SEQUENCE: 59 cccacccct ccacctct                                              18

<210> SEQ ID NO 60
<211> LENGTH: 22
<212> TYPE: DNA
<213> ORGANISM: Artificial sequence
<220> FEATURE:
<223> OTHER INFORMATION: Primer

<400> SEQUENCE: 60
ccgtcccctt cgctgggtcc tc                                        22

<210> SEQ ID NO 61
<211> LENGTH: 18
<212> TYPE: DNA
<213> ORGANISM: Artificial sequence
<220> FEATURE:
<223> OTHER INFORMATION: Primer

<400> SEQUENCE: 61
attaccacgc tcctcccg                                             18

<210> SEQ ID NO 62
<211> LENGTH: 30
<212> TYPE: DNA
<213> ORGANISM: Artificial sequence
<220> FEATURE:
<223> OTHER INFORMATION: Primer

<400> SEQUENCE: 62
gcaggaggag accagccagc agcagtgtca                                30

<210> SEQ ID NO 63
<211> LENGTH: 22
<212> TYPE: DNA
<213> ORGANISM: Artificial sequence
<220> FEATURE:
<223> OTHER INFORMATION: Primer

<400> SEQUENCE: 63
cagttcttcc tcctttctcc at                                        22

<210> SEQ ID NO 64
<211> LENGTH: 30
<212> TYPE: DNA
<213> ORGANISM: Artificial sequence
<220> FEATURE:
<223> OTHER INFORMATION: Primer

<400> SEQUENCE: 64 agggaggtg atacgcgtgg ggtccttcca                                 30

<210> SEQ ID NO 65
```

<211> LENGTH: 20
<212> TYPE: DNA
<213> ORGANISM: Artificial sequence
<220> FEATURE:
<223> OTHER INFORMATION: Primer

<400> SEQUENCE: 65
gaccttggct aagagcattg					20

<210> SEQ ID NO 66
<211> LENGTH: 20
<212> TYPE: DNA
<213> ORGANISM: Artificial sequence
<220> FEATURE:
<223> OTHER INFORMATION: Primer

<400> SEQUENCE: 66
cctggcttaa aagatcctgc					20

<210> SEQ ID NO 67
<211> LENGTH: 19
<212> TYPE: DNA
<213> ORGANISM: Artificial sequence
<220> FEATURE:
<223> OTHER INFORMATION: Primer

<400> SEQUENCE: 67
ggtgagggag gaagccaag					19

<210> SEQ ID NO 68
<211> LENGTH: 30
<212> TYPE: DNA
<213> ORGANISM: Artificial sequence
<220> FEATURE:
<223> OTHER INFORMATION: Primer

<400> SEQUENCE: 68
agaactgctg gagccactgt agctactgca			30

<210> SEQ ID NO 69
<211> LENGTH: 30
<212> TYPE: DNA
<213> ORGANISM: Artificial sequence
<220> FEATURE:
<223> OTHER INFORMATION: Primer

<400> SEQUENCE: 69
cagctgggga gcagcagctc tccctcggga			30

<210> SEQ ID NO 70
<211> LENGTH: 19
<212> TYPE: DNA
<213> ORGANISM: Artificial sequence
<220> FEATURE:
<223> OTHER INFORMATION: Primer

<400> SEQUENCE: 70
gagctgacgc tttggccac					19

<210> SEQ ID NO 71
<211> LENGTH: 20
<212> TYPE: DNA
<213> ORGANISM: Artificial sequence
<220> FEATURE:
<223> OTHER INFORMATION: Primer

<400> SEQUENCE: 71
agcggctctc actcgggaag                                                20

<210> SEQ ID NO 72
<211> LENGTH: 20
<212> TYPE: DNA
<213> ORGANISM: Artificial sequence
<220> FEATURE:
<223> OTHER INFORMATION: Primer

<400> SEQUENCE: 72
tgacgctttg gccactgctg                                                20

<210> SEQ ID NO 73
<211> LENGTH: 20
<212> TYPE: DNA
<213> ORGANISM: Artificial sequence
<220> FEATURE:
<223> OTHER INFORMATION: Primer

<400> SEQUENCE: 73
agcggctctc actcgggcag                                                20

<210> SEQ ID NO 74
<211> LENGTH: 29
<212> TYPE: DNA
<213> ORGANISM: Artificial sequence
<220> FEATURE:
<223> OTHER INFORMATION: Primer

<400> SEQUENCE: 74
cagcctggac aaagctcttc ctcttctca                                      29

<210> SEQ ID NO 75
<211> LENGTH: 20
<212> TYPE: DNA
<213> ORGANISM: Artificial sequence
<220> FEATURE:
<223> OTHER INFORMATION: Primer

<400> SEQUENCE: 75
ctggaaggcc accattgcta                                                20

<210> SEQ ID NO 76
<211> LENGTH: 23
<212> TYPE: DNA
<213> ORGANISM: Artificial sequence
<220> FEATURE:
<223> OTHER INFORMATION: Primer

<400> SEQUENCE: 76
gccaaccaat gacaactctt acc                                            23

<210> SEQ ID NO 77
<211> LENGTH: 18
<212> TYPE: DNA
<213> ORGANISM: Artificial sequence
<220> FEATURE:
<223> OTHER INFORMATION: Primer

<400> SEQUENCE: 77
gcctccacag agctggac                                                  18

<210> SEQ ID NO 78
<211> LENGTH: 30
<212> TYPE: DNA

<213> ORGANISM: Artificial sequence
<220> FEATURE:
<223> OTHER INFORMATION: Primer

<400> SEQUENCE: 78
ctgcagtgga gggcccatcg tctcgcacac        30

<210> SEQ ID NO 79
<211> LENGTH: 20
<212> TYPE: DNA
<213> ORGANISM: Artificial sequence
<220> FEATURE:
<223> OTHER INFORMATION: Primer

<400> SEQUENCE: 79
ctggaaggcc accattgcta        20

<210> SEQ ID NO 80
<211> LENGTH: 30
<212> TYPE: DNA
<213> ORGANISM: Artificial sequence
<220> FEATURE:
<223> OTHER INFORMATION: Primer

<400> SEQUENCE: 80
aggcatgacc tacagtaagg gtaaaatcga        30

<210> SEQ ID NO 81
<211> LENGTH: 30
<212> TYPE: DNA
<213> ORGANISM: Artificial sequence
<220> FEATURE:
<223> OTHER INFORMATION: Primer

<400> SEQUENCE: 81
cagccagtcg gcagcttcct cggccatcgc        30

<210> SEQ ID NO 82
<211> LENGTH: 18
<212> TYPE: DNA
<213> ORGANISM: Artificial sequence
<220> FEATURE:
<223> OTHER INFORMATION: Primer

<400> SEQUENCE: 82
tgaaggagcc ggtgcctg        18

<210> SEQ ID NO 83
<211> LENGTH: 30
<212> TYPE: DNA
<213> ORGANISM: Artificial sequence
<220> FEATURE:
<223> OTHER INFORMATION: Primer

<400> SEQUENCE: 83
tgctctccct ccagttctcg agtcccctgc        30

<210> SEQ ID NO 84
<211> LENGTH: 21
<212> TYPE: DNA
<213> ORGANISM: Artificial sequence
<220> FEATURE:
<223> OTHER INFORMATION: Primer

<400> SEQUENCE: 84
gtgtcaagga ggagacagac a        21

<210> SEQ ID NO 85
<211> LENGTH: 22
<212> TYPE: DNA
<213> ORGANISM: Artificial sequence
<220> FEATURE:
<223> OTHER INFORMATION: Primer

<400> SEQUENCE: 85
ggcaaatact tctccagcaa cc                                          22

<210> SEQ ID NO 86
<211> LENGTH: 19
<212> TYPE: DNA
<213> ORGANISM: Artificial sequence
<220> FEATURE:
<223> OTHER INFORMATION: Primer

<400> SEQUENCE: 86
ggccttctcc catatggga                                              19

<210> SEQ ID NO 87
<211> LENGTH: 27
<212> TYPE: DNA
<213> ORGANISM: Artificial sequence
<220> FEATURE:
<223> OTHER INFORMATION: Primer

<400> SEQUENCE: 87
gttctagcat ttccagcagc tccgatt                                     27

<210> SEQ ID NO 88
<211> LENGTH: 21
<212> TYPE: DNA
<213> ORGANISM: Artificial sequence
<220> FEATURE:
<223> OTHER INFORMATION: Primer

<400> SEQUENCE: 88
gtgtcaagga ggagacagac a                                           21

<210> SEQ ID NO 89
<211> LENGTH: 27
<212> TYPE: DNA
<213> ORGANISM: Artificial sequence
<220> FEATURE:
<223> OTHER INFORMATION: Primer

<400> SEQUENCE: 89
gtgaccagaa gagctggact tgctggc                                     27

<210> SEQ ID NO 90
<211> LENGTH: 28
<212> TYPE: DNA
<213> ORGANISM: Artificial sequence
<220> FEATURE:
<223> OTHER INFORMATION: Primer

<400> SEQUENCE: 90
ggagagttac tcgacagtcc ataagaag                                    28

<210> SEQ ID NO 91
<211> LENGTH: 26
<212> TYPE: DNA
<213> ORGANISM: Artificial sequence
<220> FEATURE:

<223> OTHER INFORMATION: Primer

<400> SEQUENCE: 91
cagtaggaga gaatcaagag aggagc 26

<210> SEQ ID NO 92
<211> LENGTH: 28
<212> TYPE: DNA
<213> ORGANISM: Artificial sequence
<220> FEATURE:
<223> OTHER INFORMATION: Primer

<400> SEQUENCE: 92
ggagagttac tcgacagtcc ataagtca 28

<210> SEQ ID NO 93
<211> LENGTH: 22
<212> TYPE: DNA
<213> ORGANISM: Artificial sequence
<220> FEATURE:
<223> OTHER INFORMATION: Primer

<400> SEQUENCE: 93
aaggagagtt actcgacagt cc 22

<210> SEQ ID NO 94
<211> LENGTH: 22
<212> TYPE: DNA
<213> ORGANISM: Artificial sequence
<220> FEATURE:
<223> OTHER INFORMATION: Primer

<400> SEQUENCE: 94
aggagagaat caagagagga gc 22

<210> SEQ ID NO 95
<211> LENGTH: 29
<212> TYPE: DNA
<213> ORGANISM: Artificial sequence
<220> FEATURE:
<223> OTHER INFORMATION: Primer

<400> SEQUENCE: 95
taagagagag tctgcaacct tagggtagc 29

<210> SEQ ID NO 96
<211> LENGTH: 26
<212> TYPE: DNA
<213> ORGANISM: Artificial sequence
<220> FEATURE:
<223> OTHER INFORMATION: Primer

<400> SEQUENCE: 96
aggttgcaga ctctctctta tcaccc 26

<210> SEQ ID NO 97
<211> LENGTH: 28
<212> TYPE: DNA
<213> ORGANISM: Artificial sequence
<220> FEATURE:
<223> OTHER INFORMATION: Primer

<400> SEQUENCE: 97
atgggggtgt tactcaatgg accatgtc 28

```
<210> SEQ ID NO 98
<211> LENGTH: 26
<212> TYPE: DNA
<213> ORGANISM: Artificial sequence
<220> FEATURE:
<223> OTHER INFORMATION: Primer

<400> SEQUENCE: 98
aagtggccac tgtttccaga tgatgg                                          26

<210> SEQ ID NO 99
<211> LENGTH: 20
<212> TYPE: DNA
<213> ORGANISM: Artificial sequence
<220> FEATURE:
<223> OTHER INFORMATION: Primer

<400> SEQUENCE: 99
ccatcatctg gaaacagtgg                                                 20

<210> SEQ ID NO 100
<211> LENGTH: 20
<212> TYPE: DNA
<213> ORGANISM: Artificial sequence
<220> FEATURE:
<223> OTHER INFORMATION: Primer

<400> SEQUENCE: 100
cgtggtgagc tctgtaatgg                                                 20

<210> SEQ ID NO 101
<211> LENGTH: 22
<212> TYPE: DNA
<213> ORGANISM: Artificial sequence
<220> FEATURE:
<223> OTHER INFORMATION: Primer

<400> SEQUENCE: 101
accatcatct ggaaacagtg gc                                              22

<210> SEQ ID NO 102
<211> LENGTH: 22
<212> TYPE: DNA
<213> ORGANISM: Artificial sequence
<220> FEATURE:
<223> OTHER INFORMATION: Primer

<400> SEQUENCE: 102
tgagctctgt aatggagggt gg                                              22

<210> SEQ ID NO 103
<211> LENGTH: 27
<212> TYPE: DNA
<213> ORGANISM: Artificial sequence
<220> FEATURE:
<223> OTHER INFORMATION: Primer

<400> SEQUENCE: 103
ccttatctca gccccttcct gtggcct                                         27

<210> SEQ ID NO 104
<211> LENGTH: 24
<212> TYPE: DNA
<213> ORGANISM: Artificial sequence
<220> FEATURE:
<223> OTHER INFORMATION: Primer
```

```
<400> SEQUENCE: 104
atctgtccag gatccaggga cagc                                      24

<210> SEQ ID NO 105
<211> LENGTH: 22
<212> TYPE: DNA
<213> ORGANISM: Artificial sequence
<220> FEATURE:
<223> OTHER INFORMATION: Primer

<400> SEQUENCE: 105
aacacaccca ttgcctctca ag                                        22

<210> SEQ ID NO 106
<211> LENGTH: 22
<212> TYPE: DNA
<213> ORGANISM: Artificial sequence
<220> FEATURE:
<223> OTHER INFORMATION: Primer

<400> SEQUENCE: 106
ccacagttta ctgagccatc tg                                        22

<210> SEQ ID NO 107
<211> LENGTH: 25
<212> TYPE: DNA
<213> ORGANISM: Artificial sequence
<220> FEATURE:
<223> OTHER INFORMATION: Primer

<400> SEQUENCE: 107
ccttatctca gccccttcct gtggc                                     25

<210> SEQ ID NO 108
<211> LENGTH: 28
<212> TYPE: DNA
<213> ORGANISM: Artificial sequence
<220> FEATURE:
<223> OTHER INFORMATION: Primer

<400> SEQUENCE: 108
aggatccagg gacagcaggg agcctggt                                  28

<210> SEQ ID NO 109
<211> LENGTH: 22
<212> TYPE: DNA
<213> ORGANISM: Artificial sequence
<220> FEATURE:
<223> OTHER INFORMATION: Primer

<400> SEQUENCE: 109
ggacagatgg ctcagtaaac tg                                        22

<210> SEQ ID NO 110
<211> LENGTH: 20
<212> TYPE: DNA
<213> ORGANISM: Artificial sequence
<220> FEATURE:
<223> OTHER INFORMATION: Primer

<400> SEQUENCE: 110
agggacacag agacctctag                                           20

<210> SEQ ID NO 111
<211> LENGTH: 30
```

```
<212> TYPE: DNA
<213> ORGANISM: Artificial sequence
<220> FEATURE:
<223> OTHER INFORMATION: Primer

<400> SEQUENCE: 111
ctcttcctac gcctctagag gtctctgggt                                        30

<210> SEQ ID NO 112
<211> LENGTH: 25
<212> TYPE: DNA
<213> ORGANISM: Artificial sequence
<220> FEATURE:
<223> OTHER INFORMATION: Primer

<400> SEQUENCE: 112
gcaatgagag aggagggaaa tggcg                                             25

<210> SEQ ID NO 113
<211> LENGTH: 29
<212> TYPE: DNA
<213> ORGANISM: Artificial sequence
<220> FEATURE:
<223> OTHER INFORMATION: Primer

<400> SEQUENCE: 113
gtccctcatt ttccttcaaa agcgggcag                                         29

<210> SEQ ID NO 114
<211> LENGTH: 25
<212> TYPE: DNA
<213> ORGANISM: Artificial sequence
<220> FEATURE:
<223> OTHER INFORMATION: Primer

<400> SEQUENCE: 114
gggaagagaa tggatttcct ggagc                                             25

<210> SEQ ID NO 115
<211> LENGTH: 18
<212> TYPE: DNA
<213> ORGANISM: Artificial sequence
<220> FEATURE:
<223> OTHER INFORMATION: Primer

<400> SEQUENCE: 115
cagtgagctg agaccgtg                                                     18

<210> SEQ ID NO 116
<211> LENGTH: 18
<212> TYPE: DNA
<213> ORGANISM: Artificial sequence
<220> FEATURE:
<223> OTHER INFORMATION: Primer

<400> SEQUENCE: 116
ctggtaccag tgtgtcag                                                     18

<210> SEQ ID NO 117
<211> LENGTH: 18
<212> TYPE: DNA
<213> ORGANISM: Artificial sequence
<220> FEATURE:
<223> OTHER INFORMATION: Primer

<400> SEQUENCE: 117
```

```
gactcctcag agcctcag                                              18
```

<210> SEQ ID NO 118
<211> LENGTH: 19
<212> TYPE: DNA
<213> ORGANISM: Artificial sequence
<220> FEATURE:
<223> OTHER INFORMATION: Primer

<400> SEQUENCE: 118

```
gtagctactg aagccgctg                                             19
```

<210> SEQ ID NO 119
<211> LENGTH: 19
<212> TYPE: DNA
<213> ORGANISM: Artificial sequence
<220> FEATURE:
<223> OTHER INFORMATION: Primer

<400> SEQUENCE: 119

```
cctagatcaa gaggcccag                                             19
```

<210> SEQ ID NO 120
<211> LENGTH: 18
<212> TYPE: DNA
<213> ORGANISM: Artificial sequence
<220> FEATURE:
<223> OTHER INFORMATION: Primer

<400> SEQUENCE: 120

```
acagcaggag actcgagg                                              18
```

<210> SEQ ID NO 121
<211> LENGTH: 21
<212> TYPE: DNA
<213> ORGANISM: Artificial sequence
<220> FEATURE:
<223> OTHER INFORMATION: Primer

<400> SEQUENCE: 121

```
cctcagatgc ttcatgaatg g                                          21
```

<210> SEQ ID NO 122
<211> LENGTH: 19
<212> TYPE: DNA
<213> ORGANISM: Artificial sequence
<220> FEATURE:
<223> OTHER INFORMATION: Primer

<400> SEQUENCE: 122

```
gtgaagtcag ccgaatagc                                             19
```

<210> SEQ ID NO 123
<211> LENGTH: 69
<212> TYPE: DNA
<213> ORGANISM: Homo sapiens

<400> SEQUENCE: 123

```
taccacgctc ctcccggcca caccaacttc cccygggggca cccaccccct ccacctctcc    60
tcctctccc                                                            69
```

<210> SEQ ID NO 124
<211> LENGTH: 70
<212> TYPE: DNA
<213> ORGANISM: Homo sapiens

```
<400> SEQUENCE: 124
tgcccaggga atgtccagct ctggcataaa ggacccrggt gtcctcgagc tgccatcagt    60
caggaggccg                                                           70

<210> SEQ ID NO 125
<211> LENGTH: 71
<212> TYPE: DNA
<213> ORGANISM: Homo sapiens

<400> SEQUENCE: 125
agctctggca taaaggaccc aggtgtccty gagctgccat cagtcaggag gccgtgcagc    60
ccgagatggg c                                                         71

<210> SEQ ID NO 126
<211> LENGTH: 68
<212> TYPE: DNA
<213> ORGANISM: Homo sapiens

<400> SEQUENCE: 126
gagctgccat cagtcaggag gccgtgcagy ccgagatggg ctcgtctcgg cacccctgga    60
tggggcgt                                                             68

<210> SEQ ID NO 127
<211> LENGTH: 71
<212> TYPE: DNA
<213> ORGANISM: Homo sapiens

<400> SEQUENCE: 127
gcaccctgga tggggcgtgt gggtgggcac gggatgwtgg cactgctgct ggctggtctc    60
ctcctgccag g                                                         71

<210> SEQ ID NO 128
<211> LENGTH: 67
<212> TYPE: DNA
<213> ORGANISM: Homo sapiens

<400> SEQUENCE: 128
ctggaggggc tagggaaggc agaaggaacg caggwgaaag agtcatggag gaaccatggg    60
gtaagtt                                                              67

<210> SEQ ID NO 129
<211> LENGTH: 68
<212> TYPE: DNA
<213> ORGANISM: Homo sapiens

<400> SEQUENCE: 129
cagaaggaac gcaggtgaaa gagtcatgga ggaaccaygg ggtaagttgg gcctggggtt    60
ttgagcaa                                                             68

<210> SEQ ID NO 130
<211> LENGTH: 71
<212> TYPE: DNA
<213> ORGANISM: Homo sapiens

<400> SEQUENCE: 130
ggaggaacca tggggtaagt tgggcctggg gttttsagca aaggaaagaa agataaggaa    60
agatgtggct c                                                         71
```

<210> SEQ ID NO 131
<211> LENGTH: 67
<212> TYPE: DNA
<213> ORGANISM: Homo sapiens

<400> SEQUENCE: 131
ctgtctcttc agggtccttt cttttagacc tayttgttcc tgcccttct ccattccctc      60 ttctttt                                                               67

<210> SEQ ID NO 132
<211> LENGTH: 74
<212> TYPE: DNA
<213> ORGANISM: Homo sapiens

<400> SEQUENCE: 132
aaaaaaattt taattaaaaa acaaaataca gaygggtct atgttgccca ggctggtctt      60
gaactctggg gcgc                                                       74

<210> SEQ ID NO 133
<211> LENGTH: 74
<212> TYPE: DNA
<213> ORGANISM: Homo sapiens

<400> SEQUENCE: 133
aaaaaaattt taattaaaaa acaaaataca gatrgggtct atgttgccca ggctggtctt     60
gaactctggg gcgc                                                       74

<210> SEQ ID NO 134
<211> LENGTH: 76
<212> TYPE: DNA
<213> ORGANISM: Homo sapiens

<400> SEQUENCE: 134
gggtctatgt tgcccaggct ggtcttgaac tctggggcrc atgcaatcct cccacctcag     60
cctcccaaag tgctgg                                                     76

<210> SEQ ID NO 135
<211> LENGTH: 74
<212> TYPE: DNA
<213> ORGANISM: Homo sapiens

<400> SEQUENCE: 135
tcttgaactc tggggcgcat gcaatcctcc cacctcrgcc tcccaaagtg ctgggattac     60
cggcgtgagc cact                                                       74

<210> SEQ ID NO 136
<211> LENGTH: 73
<212> TYPE: DNA
<213> ORGANISM: Homo sapiens

<400> SEQUENCE: 136 agcccctct tatattcaat gtattccttt gaggycactc actttggcac gtaattttct      60
atttttctgg ttg                                                        73

<210> SEQ ID NO 137
<211> LENGTH: 74
<212> TYPE: DNA
<213> ORGANISM: Homo sapiens

<400> SEQUENCE: 137

-continued tcaatgtatt cctttgaggt cactcactt ggcacstaat tttctatttt tctggttggt    60
gtttgcccac cctt    74

<210> SEQ ID NO 138
<211> LENGTH: 73
<212> TYPE: DNA
<213> ORGANISM: Homo sapiens

<400> SEQUENCE: 138
ccctgcgctc tgcttgggag aaacccgaga ggccgatkac tgagataagg cagaaaggtg    60
agggaggaag cca    73

<210> SEQ ID NO 139
<211> LENGTH: 73
<212> TYPE: DNA
<213> ORGANISM: Homo sapiens

<400> SEQUENCE: 139
agaggccgat tactgagata aggcagaaag gtgaggragg aagccaagcc tctttggccc    60
ttactaacca ctg    73

<210> SEQ ID NO 140
<211> LENGTH: 83
<212> TYPE: DNA
<213> ORGANISM: Homo sapiens

<400> SEQUENCE: 140
actgagataa ggcagaaagg tgagggagga agccaagcct cyttggccct tactaaccac    60
tgctttcctc cacagggacc ttg    83

<210> SEQ ID NO 141
<211> LENGTH: 81
<212> TYPE: DNA
<213> ORGANISM: Homo sapiens

<400> SEQUENCE: 141
cagggacctt ggctaagagc attggcacct tctcagaccc ytgtaaggac cccacgcgta    60
tcacctcccc taacgacccc t    81

<210> SEQ ID NO 142
<211> LENGTH: 65
<212> TYPE: DNA
<213> ORGANISM: Homo sapiens

<400> SEQUENCE: 142
ggaccccacg cgtatcacct ccctaacga cccctgcytc actgggaagg gtgactccag    60
cggct    65

<210> SEQ ID NO 143
<211> LENGTH: 79
<212> TYPE: DNA
<213> ORGANISM: Homo sapiens

<400> SEQUENCE: 143
acgacccctg cctcactggg aagggtgact ccagcggytt cagtagctac agtggctcca    60
gcagttctgg cagctccat    79

<210> SEQ ID NO 144

```
<211> LENGTH: 80
<212> TYPE: DNA
<213> ORGANISM: Homo sapiens

<400> SEQUENCE: 144
ccggttcctc ccagctgggg agcagcagct ctcactcggg aarcagcggc tctcactcgg      60
gaagcagcag ctctcattcg                                                  80

<210> SEQ ID NO 145
<211> LENGTH: 79
<212> TYPE: DNA
<213> ORGANISM: Homo sapiens

<400> SEQUENCE: 145
ggagcagcag ctctcactcg ggaagcagcg gctctcactc gggaagcagc agctctcatt      60
cgagcagcag cagcagctt                                                   79

<210> SEQ ID NO 146
<211> LENGTH: 85
<212> TYPE: DNA
<213> ORGANISM: Homo sapiens

<400> SEQUENCE: 146
aatactaaac ccttcccagc ctggacaaag ctcttcctct tcccaracct ytggggtatc      60
cagcagtggc caaagcgtca gctcc                                            85

<210> SEQ ID NO 147
<211> LENGTH: 85
<212> TYPE: DNA
<213> ORGANISM: Homo sapiens

<400> SEQUENCE: 147
aatactaaac ccttcccagc ctggacaaag ctcttcctct tcccaaacct ytggggtatc      60
cagcagtggc caaagcgtca gctcc                                            85

<210> SEQ ID NO 148
<211> LENGTH: 72
<212> TYPE: DNA
<213> ORGANISM: Homo sapiens

<400> SEQUENCE: 148
cgactctccc tgcagtggag ggcccatcgt ctcgcactcy ggcccctaca tccccagctc      60
ccactctgtg tc                                                          72

<210> SEQ ID NO 149
<211> LENGTH: 79
<212> TYPE: DNA
<213> ORGANISM: Homo sapiens

<400> SEQUENCE: 149
cctacatccc cagctcccac tctgtgtcag ggggtcagag rcctgtggtg gtggtggtgg      60
accagcacgg ttctggtgc                                                   79

<210> SEQ ID NO 150
<211> LENGTH: 81
<212> TYPE: DNA
<213> ORGANISM: Homo sapiens

<400> SEQUENCE: 150
acagttatct ggttccaggc atgacctaca gtaagggtaa aatctaycct gtgggctact      60
```

```
tcaccaaaga gaaccctgtg a                                           81

<210> SEQ ID NO 151
<211> LENGTH: 75
<212> TYPE: DNA
<213> ORGANISM: Homo sapiens

<400> SEQUENCE: 151
accccatcat ccccagccag tcggcagctt cctcggccat tgcrttccag ccagtgggga   60
ctggtggggt ccagc                                                  75

<210> SEQ ID NO 152
<211> LENGTH: 76
<212> TYPE: DNA
<213> ORGANISM: Homo sapiens

<400> SEQUENCE: 152
ccaagggacc ctgctctccc tccagttctc gagtccccag crgttctagc atttccagca   60
gctccggttc acccta                                                 76

<210> SEQ ID NO 153
<211> LENGTH: 69
<212> TYPE: DNA
<213> ORGANISM: Homo sapiens

<400> SEQUENCE: 153
ctcgagtccc cagcagttct agcatttcca gcagckccgg ttcaccctac catccctgcg   60
gcagtgctt                                                         69

<210> SEQ ID NO 154
<211> LENGTH: 50
<212> TYPE: DNA
<213> ORGANISM: Homo sapiens

<400> SEQUENCE: 154
ctagcatttc cagcagctcc gkttcaccct accatccctg cggcagtgct              50

<210> SEQ ID NO 155
<211> LENGTH: 67
<212> TYPE: DNA
<213> ORGANISM: Homo sapiens

<400> SEQUENCE: 155
ccagcagttc tagcatttcc agcagctccg gttyaccta ccatccctgc ggcagtgctt    60
cccagag                                                           67

<210> SEQ ID NO 156
<211> LENGTH: 74
<212> TYPE: DNA
<213> ORGANISM: Homo sapiens

<400> SEQUENCE: 156
ggcaccggct ccttcagcag cagctccagt tcccaatcsa gtggcaaaat catccttcag   60
ccttgtggca gcaa                                                   74

<210> SEQ ID NO 157
<211> LENGTH: 72
<212> TYPE: DNA
<213> ORGANISM: Homo sapiens
```

```
<400> SEQUENCE: 157
agttcccaat cgagtggcaa aatcatcctt cagccttgyg gcagcaagtc cagctcttct    60
ggtcaccctt gc                                                       72

<210> SEQ ID NO 158
<211> LENGTH: 68
<212> TYPE: DNA
<213> ORGANISM: Homo sapiens

<400> SEQUENCE: 158
tgaagttttc ctaccccaag gagagttact cracagtcca taagaagtca actgttgtgt    60
gtgtgcat                                                            68

<210> SEQ ID NO 159
<211> LENGTH: 71
<212> TYPE: DNA
<213> ORGANISM: Homo sapiens

<400> SEQUENCE: 159
taccccaagg agagttactc gacagtccat aagaagtcaa ctgttgtgtg tgtgcatgcc    60
ttgggcacaa a                                                        71

<210> SEQ ID NO 160
<211> LENGTH: 85
<212> TYPE: DNA
<213> ORGANISM: Homo sapiens

<400> SEQUENCE: 160
ggcacaaaca agcacataca ctatatccca tatgggagaa gkccagtgcc caggcatagg    60
gttagctcag tttccctcct tccca                                         85

<210> SEQ ID NO 161
<211> LENGTH: 77
<212> TYPE: DNA
<213> ORGANISM: Homo sapiens

<400> SEQUENCE: 161
agctcagttt ccctccttcc caaaagagtg gttctgcttt ctcyactacc ctaaggttgc    60
agactctctc ttatcac                                                  77

<210> SEQ ID NO 162
<211> LENGTH: 72
<212> TYPE: DNA
<213> ORGANISM: Homo sapiens

<400> SEQUENCE: 162
aaaagagtgg ttctgctttc tcyactaccc yaaggttgca gactctctct tatccccct    60 tcctccttcc tc                                                       72

<210> SEQ ID NO 163
<211> LENGTH: 76
<212> TYPE: DNA
<213> ORGANISM: Homo sapiens

<400> SEQUENCE: 163
agatcaccac cccttacaat tccctctact gtgtkgaaat ggtccattga gtaaccccc     60 catcaccttc tcaact                                                   76
```

<210> SEQ ID NO 164
<211> LENGTH: 71
<212> TYPE: DNA
<213> ORGANISM: Homo sapiens

<400> SEQUENCE: 164
gaaatggtcc attgagtaac accccatca scttctcaac tgggaaaccc ctgaaatgct    60
ctcagagcac c                                                        71

<210> SEQ ID NO 165
<211> LENGTH: 50
<212> TYPE: DNA
<213> ORGANISM: Homo sapiens

<400> SEQUENCE: 165
tgaaatgctc tcagagcacc tctgaygcct gaagaagtta taccttcctc              50

<210> SEQ ID NO 166
<211> LENGTH: 72
<212> TYPE: DNA
<213> ORGANISM: Homo sapiens

<400> SEQUENCE: 166
aaccatcatc tggaaacagt ggccactttt cactgaccty tcttcgacat ctagtcaacc    60
cacccaatat gc                                                       72

<210> SEQ ID NO 167
<211> LENGTH: 76
<212> TYPE: DNA
<213> ORGANISM: Homo sapiens

<400> SEQUENCE: 167
atctagtcaa cccacccaat atgccactgg gctytcgctc ccaattccac cccaccctcc    60
attacagagc tcacca                                                   76

<210> SEQ ID NO 168
<211> LENGTH: 81
<212> TYPE: DNA
<213> ORGANISM: Homo sapiens

<400> SEQUENCE: 168
gcctctcaag gcccttatct cagccccttc ctgtggccay ttccctcagt gcccagatga    60
ttccctgggt gagggagaca c                                             81

<210> SEQ ID NO 169
<211> LENGTH: 73
<212> TYPE: DNA
<213> ORGANISM: Homo sapiens

<400> SEQUENCE: 169
cagccccttc ctgtggccat ttccctcagt gcycagatga ttccctgggt gagggagaca    60
ctggggcacc ctc                                                      73

<210> SEQ ID NO 170
<211> LENGTH: 77
<212> TYPE: DNA
<213> ORGANISM: Homo sapiens

<400> SEQUENCE: 170
ttccctgggt gagggagaca ctggggcacc ctcagaggtt gragcaggct ccctgctgtc    60

-continued

| | |
|---|---|
| cctggatcct ggacaga | 77 |

<210> SEQ ID NO 171
<211> LENGTH: 50
<212> TYPE: DNA
<213> ORGANISM: Homo sapiens

<400> SEQUENCE: 171

| | |
|---|---|
| ggtgcagact ttttgccttc ttggartcct gggtctcctc tgagagtctg | 50 |

<210> SEQ ID NO 172
<211> LENGTH: 75
<212> TYPE: DNA
<213> ORGANISM: Homo sapiens

<400> SEQUENCE: 172

| | |
|---|---|
| tcttggagtc ctgggtctcc tctgagagtc tgggtggtgc tcytcctacg cctctagagg | 60 |
| tctctgtgtc cctca | 75 |

<210> SEQ ID NO 173
<211> LENGTH: 73
<212> TYPE: DNA
<213> ORGANISM: Homo sapiens

<400> SEQUENCE: 173

| | |
|---|---|
| tgggtggtgc tcttcctacg cctctagagg tctctgtgty cctcattttc cttcaaaagc | 60 |
| gggctgtgtt tct | 73 |

<210> SEQ ID NO 174
<211> LENGTH: 50
<212> TYPE: DNA
<213> ORGANISM: Homo sapiens

<400> SEQUENCE: 174

| | |
|---|---|
| tcattttcct tcaaaagcgg gctgtrtttc tcttctacct tccagctcct | 50 |

<210> SEQ ID NO 175
<211> LENGTH: 79
<212> TYPE: DNA
<213> ORGANISM: Homo sapiens

<400> SEQUENCE: 175

| | |
|---|---|
| tagatcaaga ggcccagcct gtggcagaac agagctgccr gtggtctctc catcttcaca | 60 |
| ctccctgctc tgctggggt | 79 |

<210> SEQ ID NO 176
<211> LENGTH: 79
<212> TYPE: DNA
<213> ORGANISM: Homo sapiens

<400> SEQUENCE: 176

| | |
|---|---|
| aacatggctc tcaggtgagg gctgagaagg cagagtgccc cmgtgggaaa gaggagtcgc | 60 |
| ttccactgga gaagagaga | 79 |

<210> SEQ ID NO 177
<211> LENGTH: 78
<212> TYPE: DNA
<213> ORGANISM: Homo sapiens

<400> SEQUENCE: 177

| | |
|---|---|
| gctgagaagg cagagtgccc cagtgggaaa gaggagtcgc ytccactgga gaagagagag | 60 | aaagtggagt gtgtggtg					78

<210> SEQ ID NO 178
<211> LENGTH: 76
<212> TYPE: DNA
<213> ORGANISM: Homo sapiens

<400> SEQUENCE: 178
gacttaagtc ctgagacagg cagggagagg ctgaggcgga sgaagttccc gcatcccaag		60 gagggcagag tggatt					76

<210> SEQ ID NO 179
<211> LENGTH: 75
<212> TYPE: DNA
<213> ORGANISM: Homo sapiens

<400> SEQUENCE: 179
tgagacaggc agggagaggc tgaggcggac gaagttccyg catcccaagg agggcagagt		60 ggattgtgct tgtcc					75

<210> SEQ ID NO 180
<211> LENGTH: 76
<212> TYPE: DNA
<213> ORGANISM: Homo sapiens

<400> SEQUENCE: 180
ggattgtgct tgtccctgta ggagccccac cccccacccy aggccacctc tcagagcctc		60 tgcttggctg caaagg					76

<210> SEQ ID NO 181
<211> LENGTH: 75
<212> TYPE: DNA
<213> ORGANISM: Homo sapiens

<400> SEQUENCE: 181
ctcagagcct ctgcttggct gcaaaggaat tcacccytac tgtagcactt aacccattcc		60 ctcctatcag ggtgg					75

<210> SEQ ID NO 182
<211> LENGTH: 80
<212> TYPE: DNA
<213> ORGANISM: Homo sapiens

<400> SEQUENCE: 182
tgaatttaga actgttgaaa ctccaagtct ggaatcagca raaatgtatt acattgacca		60 gaaagggatt gaatcaccct					80

<210> SEQ ID NO 183
<211> LENGTH: 80
<212> TYPE: DNA
<213> ORGANISM: Homo sapiens

<400> SEQUENCE: 183
acattgacca gaaagggatt gaatcaccct tggtccagcr tctggcccct gatctgcagc		60 caatgccagg aatcgaggtc					80

<210> SEQ ID NO 184
<211> LENGTH: 70
<212> TYPE: DNA

```
<213> ORGANISM: Homo sapiens

<400> SEQUENCE: 184
aggcctctgg gctccatcca ctgccagttc tggagwggag ctcttcactc ctccagtggt    60
taagccagca                                                           70

<210> SEQ ID NO 185
<211> LENGTH: 76
<212> TYPE: DNA
<213> ORGANISM: Homo sapiens

<400> SEQUENCE: 185
ctcttcactc ctccagtggt taagccagca ggggcaggyg gggaggacac agcagtagaa    60
tcagccaaca gctcat                                                    76

<210> SEQ ID NO 186
<211> LENGTH: 66
<212> TYPE: DNA
<213> ORGANISM: Homo sapiens

<400> SEQUENCE: 186
catgtttaga ccttgggcag ccagggaagc ytactcctgg ggcctcccgg aagccatgga    60
gagaac                                                               66

<210> SEQ ID NO 187
<211> LENGTH: 81
<212> TYPE: DNA
<213> ORGANISM: Homo sapiens

<400> SEQUENCE: 187
gatcaagtcc tggccatttg acagcagcat ttaaaggcyc tcctctactg ttacttggaa    60
atagccactt tctcccaagg t                                              81

<210> SEQ ID NO 188
<211> LENGTH: 54
<212> TYPE: DNA
<213> ORGANISM: Homo sapiens

<400> SEQUENCE: 188
ctcctctact gttacttgga aatagccacy ttctcccaag gtttcttata ctct          54

<210> SEQ ID NO 189
<211> LENGTH: 74
<212> TYPE: DNA
<213> ORGANISM: Homo sapiens

<400> SEQUENCE: 189
gaaatagcca ctttctccca aggtttctta tactctrtgg cacatctgac caccagtagc    60
aggcagaatg atgt                                                      74
```

This invention claimed is:

1. A recombinant or isolated polynucleotide comprising the corneodesmosin gene of (SEQ ID NO:1), wherein said corneodesmosin gene comprises a nucleotide substitution at position 3382 of SEQ ID NO:1.

2. A vector comprising the polynucleotide according to any one of claim 1.

3. An isolated host cell comprising the polynucleotide as claimed in claim 1; or an isolated host cell comprising a vector wherein said vector comprising the polynucleotide as claimed in claim 1.

4. A recombinant or isolated polynucletide wherein said nucleic acid sequence has full complementarity to the polynucleotide as claimed in claim 1.

* * * * *